(12) United States Patent
Brown et al.

(10) Patent No.: US 8,626,521 B2
(45) Date of Patent: Jan. 7, 2014

(54) PUBLIC HEALTH SURVEILLANCE SYSTEM

(75) Inventors: Stephen J. Brown, Woodside, CA (US);
Julie C. Cherry, Milpitas, CA (US);
Geoffrey J. Clapp, Los Altos, CA (US);
Gowthaman Gunabushanam,
Hyderabad (IN)

(73) Assignee: Robert Bosch Healthcare Systems, Inc., Palo Alto, CA (US)

( * ) Notice: Subject to any disclaimer, the term of this patent is extended or adjusted under 35 U.S.C. 154(b) by 2821 days.

(21) Appl. No.: 10/279,749

(22) Filed: Oct. 23, 2002

(65) Prior Publication Data

US 2003/0163351 A1 Aug. 28, 2003

Related U.S. Application Data

(63) Continuation-in-part of application No. 10/233,296, filed on Aug. 30, 2002, now Pat. No. 7,970,620, which is a continuation-in-part of application No. 09/237,194, filed on Jan. 26, 1999, now abandoned, which is a continuation of application No. 08/481,925, filed on Jun. 7, 1995, now Pat. No. 5,899,855, which is a continuation of application No. 08/233,397, filed on Apr. 26, 1994, now abandoned, which is a continuation-in-part of application No. 07/977,323, filed on Nov. 17, 1992, now Pat. No. 5,307,263.

(51) Int. Cl.
*G06Q 10/00* (2012.01)
*G06Q 50/00* (2012.01)

(52) U.S. Cl.
USPC .................................................. 705/2; 705/3

(58) Field of Classification Search
USPC .......................................................... 705/2–3
See application file for complete search history.

(56) References Cited

U.S. PATENT DOCUMENTS

| | | | |
|---|---|---|---|
| 3,808,502 A | 4/1974 | Babilius | |
| 3,910,257 A | 10/1975 | Fletcher et al. | |
| 4,051,522 A | 9/1977 | Healy et al. | 358/86 |
| 4,110,918 A | 9/1978 | James et al. | |
| 4,130,881 A | 12/1978 | Haessler et al. | 364/900 |
| 4,151,407 A | 4/1979 | McBride et al. | 250/199 |
| 4,173,971 A | 11/1979 | Karz | |
| 4,253,521 A | 3/1981 | Savage | 166/123 |
| 4,296,756 A | 10/1981 | Dunning et al. | |
| 4,347,568 A | 8/1982 | Giguere et al. | 364/300 |
| 4,347,851 A | 9/1982 | Jundanian | 128/668 |
| 4,360,345 A | 11/1982 | Hon | 434/262 |

(Continued)

FOREIGN PATENT DOCUMENTS

| EP | 251520 | 1/1988 | G06F 15/42 |
|---|---|---|---|
| EP | 0251520 | 1/1988 | |

(Continued)

OTHER PUBLICATIONS

F. Flachsbart, Clinical Problem-Solving: Recurrent Pulmonary Emboli. The New England Journal of Medicine. Apr. 20, 1995, vol. 332: 1104-1105.*

(Continued)

*Primary Examiner* — Sheetal R Rangrej
(74) *Attorney, Agent, or Firm* — Maginot, Moore & Beck

(57) ABSTRACT

A networked system for identifying whether an individual or a plurality of individuals has been exposed to a disease-causing infectious agent associated with a bioterrorism event.

35 Claims, 24 Drawing Sheets

(56) References Cited

U.S. PATENT DOCUMENTS

| | | | |
|---|---|---|---|
| 4,428,733 A | 1/1984 | Kumar-Misir | |
| 4,546,436 A | 10/1985 | Schneider et al. | 364/415 |
| 4,576,578 A | 3/1986 | Parker et al. | 434/307 |
| 4,625,733 A | 12/1986 | Saynajakangas | |
| 4,706,207 A | 11/1987 | Hennessy et al. | |
| 4,712,562 A | 12/1987 | Ohayon et al. | |
| 4,729,381 A | 3/1988 | Harada et al. | 128/671 |
| 4,730,253 A | 3/1988 | Gordon | |
| 4,731,726 A | 3/1988 | Allen, III | |
| 4,749,354 A | 6/1988 | Kerman | |
| 4,751,642 A | 6/1988 | Silva et al. | |
| 4,757,022 A | 7/1988 | Shults et al. | |
| 4,768,229 A | 8/1988 | Benjamin et al. | 380/20 |
| 4,779,199 A | 10/1988 | Yoneda et al. | 364/413.03 |
| 4,796,639 A | 1/1989 | Snow et al. | 127/719 |
| 4,799,199 A | 1/1989 | Scales, III et al. | 365/230 |
| 4,803,625 A * | 2/1989 | Fu et al. | 600/483 |
| 4,835,372 A | 5/1989 | Gombrich et al. | |
| 4,838,275 A * | 6/1989 | Lee | 600/483 |
| 4,858,354 A | 8/1989 | Gettler | 40/324 |
| 4,858,617 A | 8/1989 | Sanders | |
| 4,897,869 A | 1/1990 | Takahashi | 379/100 |
| 4,899,839 A | 2/1990 | Dessertine et al. | 177/25.19 |
| 4,907,973 A | 3/1990 | Hon | 434/262 |
| 4,916,441 A | 4/1990 | Gombrich | |
| 4,933,873 A | 6/1990 | Kaufman et al. | 363/513.5 |
| 4,950,246 A | 8/1990 | Muller | 604/154 |
| 4,995,402 A | 2/1991 | Smith et al. | |
| 5,007,429 A | 4/1991 | Treatch et al. | 128/677 |
| 5,016,172 A | 5/1991 | Dessertine | 364/413.02 |
| 5,019,974 A | 5/1991 | Beckers | |
| 5,024,225 A | 6/1991 | Fang | 128/630 |
| 5,025,374 A | 6/1991 | Roizen et al. | 364/413.02 |
| 5,033,474 A | 7/1991 | Varelis et al. | |
| 5,034,807 A | 7/1991 | Von Kohorn | 358/84 |
| 5,036,852 A | 8/1991 | Leishman | |
| 5,050,612 A | 9/1991 | Matsumura | |
| 5,056,059 A | 10/1991 | Tivig et al. | 364/900 |
| 5,065,315 A | 11/1991 | Garcia | 364/413.01 |
| 5,068,536 A | 11/1991 | Rosenthal | 250/341 |
| 5,077,476 A | 12/1991 | Rosenthal | |
| 5,095,798 A | 3/1992 | Okada et al. | 84/609 |
| 5,109,974 A | 5/1992 | Beer et al. | 198/346.1 |
| 5,111,817 A | 5/1992 | Clark et al. | 128/633 |
| 5,120,230 A | 6/1992 | Clark et al. | 434/307 |
| 5,128,752 A | 7/1992 | Von Kohorn | 358/84 |
| 5,134,391 A | 7/1992 | Okada | 340/799 |
| 5,137,028 A | 8/1992 | Nishimura | |
| 5,142,358 A | 8/1992 | Jason | 358/93 |
| 5,142,484 A | 8/1992 | Kaufman et al. | |
| 5,176,502 A | 1/1993 | Sanderson et al. | 417/18 |
| 5,182,707 A | 1/1993 | Cooper et al. | 364/413.11 |
| 5,204,670 A | 4/1993 | Stinton | 340/825.54 |
| 5,216,597 A | 6/1993 | Beckers | |
| 5,222,020 A | 6/1993 | Takeda | 364/413.03 |
| 5,226,431 A | 7/1993 | Bible et al. | |
| 5,227,874 A | 7/1993 | Von Kohorn | 358/84 |
| 5,249,044 A | 9/1993 | Von Kohorn | 358/86 |
| 5,262,943 A | 11/1993 | Thibado et al. | 364/413.01 |
| 5,277,197 A | 1/1994 | Church et al. | |
| 5,299,121 A | 3/1994 | Brill et al. | 364/413.01 |
| 5,307,263 A | 4/1994 | Brown | |
| 5,316,008 A | 5/1994 | Suga et al. | |
| 5,329,459 A | 7/1994 | Kaufman et al. | 364/479 |
| 5,329,608 A | 7/1994 | Bocchieri et al. | 395/2.52 |
| 5,331,549 A | 7/1994 | Crawford, Jr. | |
| 5,331,555 A | 7/1994 | Hashimoto et al. | |
| 5,336,245 A | 8/1994 | Adams et al. | |
| 5,339,821 A | 8/1994 | Fujimoto | |
| 5,341,291 A | 8/1994 | Roizen et al. | 364/413.02 |
| 5,344,324 A | 9/1994 | O'Donnell et al. | 434/258 |
| 5,357,427 A | 10/1994 | Langen et al. | |
| 5,359,509 A | 10/1994 | Little et al. | |
| 5,366,896 A | 11/1994 | Margrey et al. | 436/48 |
| 5,377,100 A | 12/1994 | Pope et al. | |
| 5,377,258 A | 12/1994 | Bro | |
| 5,381,138 A | 1/1995 | Stair et al. | |
| 5,390,238 A | 2/1995 | Kirk et al. | |
| 5,399,821 A | 3/1995 | Inagaki et al. | 200/341 |
| 5,410,471 A | 4/1995 | Alyfuku et al. | 364/413.02 |
| 5,434,611 A | 7/1995 | Tamura | |
| 5,441,047 A * | 8/1995 | David et al. | 600/483 |
| 5,454,721 A | 10/1995 | Kuch | 434/127 |
| 5,454,722 A | 10/1995 | Holland et al. | 434/271 |
| 5,456,606 A | 10/1995 | McIntyre | 434/236 |
| 5,465,082 A | 11/1995 | Chaco | |
| 5,467,269 A | 11/1995 | Flaten | 364/401 |
| 5,471,039 A | 11/1995 | Irwin, Jr. et al. | |
| 5,483,276 A | 1/1996 | Brooks et al. | 348/2 |
| 5,488,423 A | 1/1996 | Walkingshaw et al. | 348/460 |
| 5,501,231 A | 3/1996 | Kaish | 128/725 |
| 5,502,636 A | 3/1996 | Clarke | 364/401 |
| 5,504,519 A | 4/1996 | Remillard | 348/7 |
| 5,517,405 A | 5/1996 | McAndrew et al. | 364/401 |
| 5,524,637 A | 6/1996 | Erickson | |
| 5,527,239 A | 6/1996 | Abbondanza | |
| 5,542,420 A | 8/1996 | Goldman et al. | 128/630 |
| 5,544,649 A | 8/1996 | David et al. | 128/630 |
| 5,549,117 A | 8/1996 | Tacklind et al. | |
| 5,550,575 A | 8/1996 | West et al. | 348/5.5 |
| 5,553,609 A | 9/1996 | Chen et al. | 128/630 |
| 5,558,638 A | 9/1996 | Evers et al. | |
| 5,569,212 A | 10/1996 | Brown | 604/207 |
| 5,572,421 A | 11/1996 | Altman et al. | 395/203 |
| 5,574,828 A | 11/1996 | Hayward et al. | 395/50 |
| 5,576,952 A | 11/1996 | Stutman et al. | |
| 5,583,758 A | 12/1996 | McIlroy et al. | 395/202 |
| 5,594,637 A | 1/1997 | Eisenberg et al. | 395/202 |
| 5,596,994 A | 1/1997 | Bro | |
| 5,597,307 A | 1/1997 | Redford et al. | 434/118 |
| 5,601,435 A | 2/1997 | Quy | |
| 5,619,991 A | 4/1997 | Sloane | 128/630 |
| 5,624,265 A | 4/1997 | Redford et al. | 434/307 |
| 5,628,309 A | 5/1997 | Brown | 128/632 |
| 5,631,844 A | 5/1997 | Margrey et al. | 364/496 |
| 5,633,910 A | 5/1997 | Cohen | 379/38 |
| 5,642,731 A | 7/1997 | Kehr | 128/630 |
| 5,642,936 A | 7/1997 | Evans | 128/630 |
| 5,659,793 A | 8/1997 | Escobar et al. | |
| 5,664,228 A | 9/1997 | Mital | |
| 5,670,711 A | 9/1997 | Detournay et al. | 73/84 |
| 5,675,635 A | 10/1997 | Vos et al. | 379/113 |
| 5,678,562 A | 10/1997 | Sellers | 128/710 |
| 5,678,571 A | 10/1997 | Brown | |
| 5,680,590 A | 10/1997 | Parti | 395/500 |
| 5,687,322 A | 11/1997 | Deaton et al. | 395/214 |
| 5,687,717 A | 11/1997 | Halpern et al. | 128/630 |
| 5,704,366 A | 1/1998 | Tacklind et al. | |
| 5,704,902 A | 1/1998 | Vandenbelt et al. | 601/72 |
| 5,711,297 A | 1/1998 | Iliff | 128/630 |
| 5,715,451 A | 2/1998 | Marlin | 395/615 |
| 5,717,913 A | 2/1998 | Driscoll | 395/605 |
| 5,720,733 A | 2/1998 | Brown | 604/207 |
| 5,722,418 A | 3/1998 | Bro | |
| 5,727,153 A | 3/1998 | Powell | 395/214 |
| 5,732,709 A | 3/1998 | Tacklind et al. | |
| 5,752,234 A | 5/1998 | Withers | 705/2 |
| 5,760,771 A | 6/1998 | Blonder et al. | 345/336 |
| 5,772,585 A | 6/1998 | Lavin et al. | 600/300 |
| 5,782,814 A | 7/1998 | Brown et al. | 604/207 |
| 5,785,650 A | 7/1998 | Akasaka et al. | 600/300 |
| 5,791,342 A | 8/1998 | Woodard | 128/630 |
| 5,792,117 A | 8/1998 | Brown | 604/207 |
| 5,793,969 A | 8/1998 | Kamentsky et al. | 395/200.43 |
| 5,796,393 A | 8/1998 | MacNaughton et al. | 345/329 |
| 5,802,494 A | 9/1998 | Kuno | 705/2 |
| 5,810,747 A | 9/1998 | Brudny et al. | 600/595 |
| 5,812,983 A | 9/1998 | Kumagai | |
| 5,819,735 A | 10/1998 | Mansfield et al. | 128/630 |
| 5,822,544 A | 10/1998 | Chaco et al. | 395/202 |
| 5,822,715 A | 10/1998 | Worthington et al. | |
| 5,825,283 A | 10/1998 | Camhi | 340/438 |
| 5,827,180 A | 10/1998 | Goodman | 600/300 |
| 5,828,943 A | 10/1998 | Brown | |

(56) References Cited

U.S. PATENT DOCUMENTS

| | | | |
|---|---|---|---|
| 5,832,448 A | 11/1998 | Brown | |
| 5,835,896 A | 11/1998 | Fisher et al. | 705/37 |
| 5,842,976 A | 12/1998 | Williamson | 600/300 |
| 5,868,669 A | 2/1999 | Iliff | |
| 5,875,432 A | 2/1999 | Sehr | 705/12 |
| 5,879,163 A | 3/1999 | Brown et al. | |
| 5,887,133 A | 3/1999 | Brown et al. | |
| 5,893,077 A | 4/1999 | Griffin | 705/34 |
| 5,893,098 A | 4/1999 | Peters et al. | |
| 5,897,493 A | 4/1999 | Brown | |
| 5,899,855 A | 5/1999 | Brown | |
| 5,911,687 A | 6/1999 | Sato et al. | 600/300 |
| 5,913,310 A | 6/1999 | Brown | |
| 5,918,603 A | 7/1999 | Brown | |
| 5,920,477 A | 7/1999 | Hoffberg et al. | 364/148 |
| 5,933,136 A | 8/1999 | Brown | |
| 5,940,801 A | 8/1999 | Brown | |
| 5,950,632 A | 9/1999 | Reber et al. | |
| 5,951,300 A | 9/1999 | Brown | |
| 5,956,501 A | 9/1999 | Brown | |
| 5,960,403 A | 9/1999 | Brown | |
| 5,961,446 A | 10/1999 | Beller et al. | 600/300 |
| 5,983,217 A | 11/1999 | Khosravi-Sichani et al. | 707/3 |
| 5,985,559 A | 11/1999 | Brown | |
| 5,987,471 A | 11/1999 | Bodine et al. | 707/103 |
| 5,995,969 A | 11/1999 | Lee et al. | 707/103 |
| 5,997,476 A | 12/1999 | Brown | |
| 6,001,065 A | 12/1999 | DeVito | |
| 6,022,315 A | 2/2000 | Iliff | |
| 6,022,615 A | 2/2000 | Rettenbacher | 428/317.9 |
| 6,029,138 A | 2/2000 | Khorasani et al. | 705/2 |
| 6,032,119 A | 2/2000 | Brown et al. | |
| 6,046,761 A | 4/2000 | Echerer | 348/13 |
| 6,049,794 A | 4/2000 | Jacobs et al. | 706/45 |
| 6,050,940 A | 4/2000 | Braun | |
| 6,055,314 A | 4/2000 | Spies et al. | 380/21 |
| 6,055,487 A | 4/2000 | Margery et al. | 702/84 |
| 6,055,506 A | 4/2000 | Frasca, Jr. | 705/3 |
| 6,057,758 A | 5/2000 | Dempsey et al. | 340/539 |
| 6,101,478 A | 8/2000 | Brown | |
| 6,110,148 A | 8/2000 | Brown et al. | 604/207 |
| 6,138,145 A | 10/2000 | Kawanaka | 709/204 |
| 6,144,837 A | 11/2000 | Quy | |
| 6,151,586 A | 11/2000 | Brown | |
| 6,161,095 A | 12/2000 | Brown | |
| 6,167,362 A | 12/2000 | Brown et al. | |
| 6,168,563 B1 | 1/2001 | Brown | |
| 6,177,940 B1 | 1/2001 | Bond et al. | |
| 6,186,145 B1 | 2/2001 | Brown | |
| 6,189,029 B1 * | 2/2001 | Fuerst | 709/217 |
| 6,196,970 B1 | 3/2001 | Brown | |
| 6,210,272 B1 | 4/2001 | Brown | |
| 6,233,539 B1 | 5/2001 | Brown | |
| 6,240,393 B1 | 5/2001 | Brown | |
| 6,246,992 B1 | 6/2001 | Brown | |
| 6,248,065 B1 | 6/2001 | Brown | |
| 6,260,022 B1 | 7/2001 | Brown | |
| 6,270,455 B1 | 8/2001 | Brown | |
| 6,330,426 B2 | 12/2001 | Brown et al. | |
| 6,334,778 B1 | 1/2002 | Brown | |
| 6,368,273 B1 | 4/2002 | Brown | |
| 6,375,469 B1 | 4/2002 | Brown | |
| 6,381,577 B1 | 4/2002 | Brown | |
| 6,849,045 B2 | 2/2005 | Iliff | |
| 6,968,375 B1 | 11/2005 | Brown | |
| 7,167,818 B2 | 1/2007 | Brown | |
| 7,168,818 B1 | 1/2007 | Schnell | |
| 7,252,636 B2 | 8/2007 | Brown | |
| 7,305,348 B1 | 12/2007 | Brown | |

FOREIGN PATENT DOCUMENTS

| | | | |
|---|---|---|---|
| EP | 320749 | 6/1989 | G06F 159/00 |
| EP | 0320749 | 6/1989 | |
| EP | 370599 | 5/1990 | A61J 7/00 |
| EP | 0353046 | 10/1990 | |
| EP | 461910 | 12/1991 | |
| EP | 508912 | 10/1992 | A63H 3/28 |
| EP | 526166 | 2/1993 | G06F 15/42 |
| EP | 676709 | 10/1995 | |
| EP | 676709 A2 | 10/1995 | |
| EP | 680727 | 11/1995 | A61B 5/00 |
| EP | 761160 | 3/1997 | A61B 5/00 |
| GB | 2218831 | 11/1989 | |
| JP | 62-226278 | 10/1987 | |
| WO | WO93/02622 | 2/1993 | A61B 5/16 |
| WO | WO-93-02622 | 2/1993 | |
| WO | WO94/02222 | 2/1994 | |
| WO | WO94/16774 | 8/1994 | A63B 21/00 |
| WO | WO95/09386 | 4/1995 | G04B 47/00 |
| WO | WO95/20199 | 7/1995 | G06F 19/00 |
| WO | WO-95-20199 | 7/1995 | |
| WO | WO-95-29447 | 11/1995 | |
| WO | WO96/25877 | 8/1996 | A61B 5/0404 |
| WO | WO97/08605 | 3/1997 | |
| WO | WO-97-08605 | 3/1997 | |
| WO | WO97/12544 | 4/1997 | A61B 5/00 |
| WO | WO98/16895 | 4/1998 | G06F 159/00 |

OTHER PUBLICATIONS

Clarke, Keith C., McLafferty, Sara L., Tempalski, Barbara J. on Epidemiology and Geographic Information Systems: A Review and Discussion of Future Directions. Emerging Infectious Diseases. Apr.-Jun. 1996, vol. 2: No. 2.*

"+5V Powered Isolated RS-232 Drivers/Receivers," Maxim Integrated Products, publication date unknown.

"CD-ROM Mavericks:Proprietary TV-Based Players," Byte Guide to CD-ROM, publication date unknown, pp. 100-105.

"Introducing the Next Generation of About Your Diabetes," US Pharmacopeial Convention and American Diabetes Association, 4pgs, 1993.

Anonymous, "Health Hero Network, Inc. Receives First-Ever FDA Clearance for Connecting Medical Devices to Internet," PR Newswire, Dec. 2, 1999, 3 pgs., Dec. 2, 1999.

Bower, "Brain Clues to Energy-Efficient Learning," Science News, v141, p. 215(1).

Bruce, "Health Hero Network CEO, CNNfn," Digital Jam, Dec. 1, 1999, 3pgs. Dec. 1, 1999.

Bruce, et al, "The Effects of Sympathetic Nervous System Activation and Psychological Stress," Diabetologia, 35(9), 1992, 835-843, 1992.

Finston, "Parent + Teacher = Healthy Child," Diabetes Forecast, v47, n9, p. 26(5).

Fox, "Not My Type: Type B Behavior, Type 1 Diabetes Plus Stress Equals Blood Sugar Blues," Health, v20, n3, p. 22(1) (Abstract).

Giuffrida, Antonio, et al., "Should we pay the patient? Review of Financial incentives to enhance patient compliance," Biomedical Journal, vol. 315, pp. 703-707, 1997, Sep. 20, 1997.

Kauffmann, Francine, et al., "Epidemiological Study of the Genetics and Environment of Asthma, Bronchial Hyperresponsiveness and Atopy", Am. J. Respir. Crit. Care Med., vol. 156, pp. S123-S129, 1997.

Marsh, David G., "Approaches Toward the Genetic Analysis of Complex Traits Asthma and Atopy", Am J Respir Crit Care Med, vol. 156, pp. S-133-S138, 1997.

Martinez, Fernando D., "Complexities of the Genetics of Asthma", Am J Respir Crit Care Med, vol. 156, pp. S117-S122, 1997.

Mazzola, "Video Diabetes: A Teaching Tool for Children with Insulin-Dependent Diabetes," Proceedings—7th Annual Symposium on Computer Applications in Medical Care, Washington DC.

McCullagh, PJ et al., "Computerized paradigms for eliciting the contingent negative variation event-related potential," Proceedings of the Annual International Conference of the Engineering in Medicine & Biology Society, IEEE, Conf. 14, p. 2481-2483, Oct. 1992.

Schement, "An Intelligent Controller for Neurophysiological Experiments," Proceedings of the Annual Symposium on Computer Based Medical Systems, Durham, Jun. 14-17, 1992, p. 528, line 1—p. 529, line 21, Jul. 1992.

(56) References Cited

OTHER PUBLICATIONS

Meissner et al, "Building an Integrated Clinical and Research Network," Proceedings of the SPIE, vol. 2618, p. 92-99, Oct. 23-24, 1995.
Moore, "New applications break through storage boundaries," Computer Technology Review, Oct. 1999, vol. 19, No. 10, p. 1, Oct. 1999.
Reis, Howard, "Telemedicine: Transmitting Expertise to the Point of Care," Proceedings: Toward an Electronic Patient Record, pp. 248-256, 1997.
Schork, Nicholas J., "Genetics of complex disease", Am. J. Respir. Crit. Care Med., vol. 156, pp. S103-S109, 1997.
Shandle, Jack, "Who Will Dominate the Desktop in the 90's?" Electronics, Feb. 1990, pp. 48-50, Feb. 1990.
Voelker, Rebecca, "Shoe Leather Therapy is Gaining on TB", JAMA vol. 275, 743, Mar. 13, 1996.
Bai, "Design of home healthcare network," IEEE 1997 pp. 1657-1658.
Jianwu, "Using Human factors engineering as the basis for developing medical human-computer systems," IEEE 1996, pp. 1202-1207.
Kim, "A multimedia information system for home health-care support" IEEE 1997 pp. 1657-1658.
Heritage Dictionary pa.
American Heritage Dictionary pe.
Definition of Client Server from PCMAG COM.
The Merriam Webster Online Dictionary display.
The Merriam Webster Online Dictionary graphic.
The Merriam Webster Online Dictionary pictorial.
The Merriam Webster Online Dictionary symbol.
The Merriam Webster Online Dictionary symbolic.
The Merriam Webster Online Dictionary Video.
Websters Dictionary II com.
Websters Dictionary II con.
Websters Dictionary II i.
Websters Dictionary II m.
Nov. 1978 Licklider Applications of information Networks Proceedings of the IEEE vol. 66 No. 11.
Jan. 1980 Haynes Geriatrics How to Detect manage Low Patient Compliance in Chronic Illness.
Nov. 1980 Haynes Hypertension Can simple Clinical measurements detect patient noncompliance.
1986 Physicians Guide Using the Health Buddy System.
1986 Thompson and Vandenberg, Clinical Biochemistry (1986) 19:255-261.
Oct. 19, 1986 Thompson in Vivo Probes.
Jun. 2, 1987 U.S. Appl. 07/096,998 Lee Amendment.
1988 Hughes Bedside Terminals Clinicom MD.
Aug. 10, 1988 U.S. Appl. 06/879,900 Fu Amendment.
1989 Velho et. Al., Biomed. Biochim. Acta (1989) 48(11/12):957:964.
May 1989 Paperny Adolescent Pregnancy Prevention by Health Education Computer Games Computer Assisted Instruction.
Oct. 12, 1989 Diabcare Flyer Boehringer Mannheim HH101661-HH101668.
1990 Matthews et al BMJ Analysis of serial measurement in medical research.
1991 Diabcare User Manual HH007288-HH007331.
Jul. 23, 1991 Dept of Health and Human Services the Physician Guide from the K864318 510K.
1992 Durant Medicine and Science in Sports and Exercise 24(2)265-271.
Nov. 17, 1992 07977323 Transmittal Letter.
1993 Camit S Manual v3.00.
May 1994 Szolovits Guardian Angel Patient Centered Health Information Systems.
Jul. 1994 Genesereth Software Agents.
Aug. 10, 1995 Lai Abstraction Models at System Level for Networked Interactive Multimedia Scripting.
Sep. 1, 1995 Lunt The Smart Cards Are Here.
Oct. 30, 1995 Mortorala introduces PCMCIA28.8 Modem.
Nov. 1995 Hoffman General Purpose Telemetry for Analog Biomedical Signals.
1996 Williams Motivational Predictors of Weight Loss.
Jul. 12, 1996 Iliff U.S. Appl. No. 60/021,614.
Sep. 24, 2001 U.S. Appl. No. 09/300,856 Amendment.
Apr. 21, 2003 U.S. Appl. No. 09/422,046 Amendment with Affidavit.
Jun. 13, 2005 U.S. Appl. No. 11/150,145 Amendment.
Mar. 29, 2006 U.S. Appl. No. 11/150,145 OA.
Jun. 19, 2006 U.S. Appl. No. 09/237,194 Office Actions Response.
Jun. 26, 2006 U.S. Appl. No. 11/150,145 Amendment.
Aug. 17, 2006 Abbott Amended Complaint.
Aug. 17, 2006 Abbott v Dexcom 06-514.
Aug. 17, 2006 Request for Re-examination 5899855 90008234.
Sep. 21, 2006 U.S. Appl. No. 09/237,194 Declation of Stephen Brown with Attached Exhibits Y and Z thereof.
Sep. 22, 2006 U.S. Appl. No. 11/150,145 OA.
Sep. 27, 2006 U.S. Appl. No. 09/422,046 Office Actions Response.
Oct. 27, 2006 U.S. Appl. No. 11/150,145 Amendment.
Jan. 4, 2007 U.S. Appl. No. 11/150,145 Amendment.
May 9, 2007 Leapfrog v Fisher Price.
Oct. 29, 2007 Request for Re-examination 5899855 90008909.
Nov. 9, 2007 Request for Re-examination 7223236 90010053.
Nov. 15, 2007 Request for Re-examination 7223236 90010053.
Jan. 25, 2008 Dept of Health and Human Services The Physicians Guide Become publicly Available.
Jun. 20, 2008 U.S. Appl. No. 09/422,046 OA.
Jun. 20, 2008 Alere First Supplemental Response to Plaintiff Interrogatories.
Aug. 1, 2008 Excerpts from the Prosecution History for US Patent 5899855.
Aug. 1, 2008 Inter Party Re-Exam 7223236 95000386.
Aug. 1, 2008 Request for Re-examination 5601435 90009237.
Aug. 1, 2008 Request for Re-examination 5879163 90009238.
Aug. 1, 2008 Request for Re-examination 6151586 90009240.
Aug. 1, 2008 Request for Re-examination 6161095 90009239.
Aug. 1, 2008 Request for Re-examination 7223236 95000386.
Sep. 23, 2008 U.S. Appl. No. 90/009,281 Request for Re-Examination 6368273.
Dec. 4, 2008 Request for Re-Examination 5899855 90009352.
Dec. 10, 2008 Alere Second Supplemental Response to Plaintiff Interrogatories.
Dec. 10, 2008 Alere Second Supplemental Response to Plaintiff Interrogatories Exhibit 1.
Dec. 10, 2008 Alere Second Supplemental Response to Plaintiff Interrogatories Exhibit 2.
Dec. 10 , 2008 Alere Second Supplemental Response to Plaintiff Interrogatories Exhibit 3.
Dec. 10, 2008 Alere Second Supplemental Response to Plaintiff Interrogatories Exhibit 4.
Dec. 10, 2008 Alere Second Supplemental Response to Plaintiff Interrogatories Exhibit 5.
Dec. 10, 2008 Alere Second Supplemental Response to Plaintiff Interrogatories Exhibit 6.
Dec. 10, 2008 Alere Second Supplemental Response to Plaintiff Interrogatories Exhibit 7.
Dec. 10 2008 Alere Second Supplemental Response to Plaintiff Interrogatories Exhibit 8.
Dec. 10, 2008 Alere Second Supplemental Response to Plaintiff Interrogatories Exhibit 8A.
Dec. 10, 2008 Alere Second Supplemental Response to Plaintiff Interrogatories Exhibit 9.
Dec. 10, 2008 Alere Second Supplemental Response to Plaintiff Interrogatories Exhibit B.

* cited by examiner

SCRIPT ENTRY SCREEN

SCRIPT NAME: PUBLIC HEALTH 1

| QUERIES | CHOICE 1 | CHOICE 2 | CHOICE 3 | CHOICE 4 |
|---|---|---|---|---|
| DOES THE PATIENT HAVE... CHOSE THE FIRST THAT APPLIES | FEVER | ACUTE GE (NVD) | ACUTE WEAKNESS/ FACIAL PARALYSIS | NONE OF THE ABOVE |
| IS THE FEVER BETWEEN... | 38-38.9 | 39-39.9 | GREATER THAN 40 | AFEBRILE, SELF REPORTED |
| DOES THE PATIENT HAVE... CHOSE THE FIRST THAT APPLIES | A RASH | ALTERED MENTAL STATUS | COUGH/ SHORTNESS OF BREATH | NONE OF THE ABOVE |
| WHAT KIND OF RASH DOES THE PATIENT HAVE? | VESICULAR (BLISTERS) | PETECHIAE | ESCHAR | OTHER |

SELECT DEVICE TYPE (S)

☒ THERMOMETER  ☐ LAB DIAGNOSTICS  ☐ OTHER

CONNECTION TIME: 03:00 ▽   CREATE SCRIPT   CANCEL

*FIG. 5*

```
NUMBER 9000001 (LF)
LED 1 (LF)
ZAP (LF)
CLS (LF)
DISPLAY PLEASE ENTER IN ID CODE, INSERT SMART CARD,
    OR CONNECT MONITORING DEVICE (LF)
WAIT (LF)
CLS (LF)
DISPLAY ANSWER QUESTIONS NOW?
    PRESS ANY BUTTON TO START (LF)
WAIT (LF)
CLS (LF)
DISPLAY DOES THE PATIENT HAVE
      (CHOSE THE FIRST THAT APPLIES)
      FEVER   ACUTE GE    ACUTE WEAKNESS/   NONE OF
              (NVD)       FACIAL PARALYSIS  THE ABOVE (LF)
INPUT 0000 (LF)
CLS (LF)
DISPLAY IS THE FEVER BETWEEN
      38-38 9   39-39 9    GREATER     AFEBRILE,
                           THAN 40     SELF REPORTED (LF)
INPUT 0000 (LF)
CLS (LF)
DISPLAY DOES THE PATIENT HAVE
      CHOSE THE FIRST THAT APPLIES
      A RASH    ALTERED    COUGH/      NONE OF
                MENTAL     SHORTNESS   THE ABOVE
                STATUS     OF BREATH (LF)
```

FIG 6A

```
INPUT 0000 (LF)
CLS (LF)
DISPLAY WHAT KIND OF RASH DOES THE PATIENT HAVE?
      VESICULAR   PETECHIAE   ESCHAR   OTHER
      (BLISTERS) (LF)
INPUT 0000 (LF)
CLS (LF)
DISPLAY CONNECT THERMOMETER AND PRESS
      ANY BUTTON WHEN FINISHED (LF)
INPUT 0000 (LF)
CLS (LF)
DISPLAY COLLECTING MEASUREMENTS (LF)
COLLECT THERMOMETER (LF)
CLS (LF)
DISPLAY CONNECT APPARATUS TO PHONE JACK
      AND PRESS ANY BUTTON WHEN FINISHED (LF)
WAIT (LF)
LED 0 (LF)
CLS (LF)
DELAY 03 00 (LF)
DISPLAY CONNECTING TO SERVER (LF)
CONNECT (LF)
(EOF)
```

FIG 6B

```
                57
                  SCRIPT ASSIGNMENT SCREEN
              AVAILABLE SCRIPTS        CARE FACILITY
      106                      108
          [X]  PUBLIC HEALTH 1      [X]  EMSD 60120

[ ]  POSITIVE LABS 9      [ ]  COUNTY 9423

[ ]  ISSUED ALERT 22      [ ]  STATE OF CA

[ADD SCRIPT]   [ASSIGN SCRIPT]   [DELETE SCRIPT]
      110              112              114
```

FIG. 7

```
          ┌─────────────────────────────────┐
          │ DOES THE PATIENT HAVE           │
          │ (CHOSE THE FIRST THAT APPLIES)  │
    26    │ FEVER  ACUTE GE  WEAKNESS  NONE │ 64
          │           (N/V/D)               │
          └─────────────────────────────────┘

PCR FOR ANTHRAX SURVEILLANCE STATUS REPORT

FACILITY ID: 90210013 ▽    DATE OF MEASUREMENT: SEPT 14, 2002 ▽

42

RESPONSES FOR PATIENT # 6 OF 7

1. IS THE POSITIVE TEST COMPATIBLE WITH THE CLINICAL SETTING? — YES
2. TYPE OF ANTHRAX: MENINGITIS
3. DOES THE PATIENT WORK IN A MAIL FACILITY? — NO
4. DOES THE PATIENT'S OCCUPATION REQUIRE HIM/HER TO COME IN CLOSE CONTACT WITH ANIMALS? — YES
5. IS ANYONE ELSE IN THE PATIENT'S WORKPLACE/ HOUSEHOLD HAVING SIMILAR SYMPTOMS? — NO

116

OVERVIEW REPORT

TOTAL NUMBER OF SUSPECTED CASES = 12
NUMBER OF PCR CONFIRMED CASES = 7
RELATED FACILITIES 90210007, 09, 12, 14, 19
TOTAL NUMBER OF CASES = 31

1. YES = 7/7  NO = 0/7
2. SKIN=2 | P=1 | MENG = 2 | MORE THAN 1 = 3
3. NO=1 | YES = 6
4. Y= 1 | NO = 6
5. YES = 2 | NO = 2 | NOT KNOWN = 3

*FIG. 10B*

ANALYSIS ENGINE 54C REPORT ID= ANA-2002-9-25-0723

DATE & TIME OF REQUISITION = 25 SEPTEMBER 2002; 20.35 HRS (EST)
DATE & TIME OF GENERATION = 25 SEPTEMBER 2002; 20.39 HRS(EST)
ANALYST ID = ANA-3050019
HEALTH DEPARTMENT ID = DEP-0305
HEALTHCARE FACILITY ID = HCF-30530-103

SEQUENCE:
>>> LAB TEST ID= LAB-5510 REPORTED 'POSITIVE' FROM LAB FACILITY
    ID = LFC-30530-022 AT 14.00 HRS
>>> PROTOCOL ID = LAB-5510-POS ACTIVATED
>>> SCRIPT ID = LAB-5510-POS SENT TO LAB FACILITY ID = LFC-30530-
    022 AT 14.05 HRS.
>>> SCRIPT ID = TRG-5510-POS SENT TO TRIAGE POINT AT
    HEALTHCARE FACILITY ID = HCF-30530-103 AT 14.06 HRS. NEW
    SCRIPT INCORPORATED INTO TRIAGE POINT AT 14.06 HRS.
>>> SCRIPT ID = DOC-5510-POS SENT TO CLINICIAN ID = DOC-30530-103-
    1007 AT 14.06 HRS.
>>> SCRIPT ID = ALT-5510-POS SENT TO ALL FACILITIES IN COUNTY
    WITH CORRELATION COEFFICIENT > 0 AT 14.16 HRS.
>>> RESPONSES RECEIVED FOR SCRIPT ID = LAB-5510-POS FROM LAB
    FACILITY ID = LFC-30530-022 AT 15.30 HRS
>>> RESPONSES RECEIVED FOR SCRIPT ID = DOC-5510-POS FROM
    CLINICIAN ID = DOC-30530-103-1007 AT 16.06 HRS
>>> FOLLOWED DIRECTIVE = 22, PROTOCOL ID = LAB-5510-POS:
    INFORMED ANALYST ID = ANA-3050019 AT 16.07 HRS
>>> SEARCH ENGINE ACTIVATED. SEARCH ID = SER-2002-9-25-0723
    REQUESTED AT 16.45 HRS.
>>> MAPPING ENGINE ACTIVATED. RAW MAP ID = MAP-2002-9-25-0723
    REQUESTED AT 16.45 HRS.
>>> NEW SCRIPT ID = NEW-1600-107 CREATED BY ANALYST ID = ANA-
    3050019 AT 17.47 HRS. SCRIPT ID = NEW-1600-107 SENT TO ALL
    FACILITIES OF COUNTY ID = 0305
>>> 23% RESPONSES RECEIVED FROM COUNTY ID = 0305 FOR SCRIPT ID
    = NEW-1600-107 AS OF 20.35 HRS

LAB REPORT:
LAB TEST = PCR FOR YERSINIA PESTIS
REPORT = 'POSITIVE'
LAB FACILITY = ALPHAVILLE MEDICAL CENTER-ALPHAVILLE – CA

RESPONSES FROM LAB FACILITY:
NATURE OF SPECIMEN: EXUDATE FROM INGUINAL ULCER
AGE OF PATIENT: 30-40
SEX: MALE
OCCUPATION OF PATIENT: AGRICULTURE
ANY OTHER SPECIMENS TAKEN FOR ANALYSIS: YES
BLOOD: YES
SPUTUM: NO
IS BLOOD CULTURE POSITIVE: REPORT NOT YET AVAILABLE
ANY OTHER PATIENT TESTED IN RECENT PAST? NO

*FIG. 17A*

RESPONSES FROM TRIAGE FACILITY
ANY PATIENTS WITH INGUINAL/AXILLARY BUBOES IN LAST 7 DAYS: YES
HOW MANY: 2
ANY PATIENTS WITH SEPTICEMIC FEATURES? NO
ANY PATIENTS WITH SEVERE PNEUMONIA-LIKE FEATURES: YES
ANY DEATHS FROM PNEUMONIA IN LAST 7 DAYS: NO
PLEASE APPLY PLAGUE QUESTIONAIRRE SCRIPT FOR PATIENTS
    PRESENTING WITH ANY OF THE FOLLOWING COMPLAINTS:
    INGUINAL & AXILLARY BUBOES, SEVERE SEPTICEMIA & SHOCK,
    FULMINANT PNEUMONIA: OK
PLEASE APPLY EXTENDED RESPIRATORY SCRIPT ON ALL PATIENTS
    WITH ACUTE UPPER RESPIRATORY INFECTIONS: OK

RESPONSES FROM CLINICIAN
NATURE OF LESION: INGUINAL BUBO
OCCUPATION OF PATIENT: AGRICULTURE
DIFFERENTIAL DIAGNOSIS SUSPECTED: NO, IT IS A CLASSICAL CASE.
HISTORY OF EXPOSURE TO WILD ANIMALS: NO
RECENT HISTORY OF TRAVEL/ CAMPING IN THE FOREST: NO
DOES PATIENT KNOW ANYONE WHO DEVELOPED FEATURES OF
    PLAGUE RECENTLY- BUBONIC/ PNEUMONIC/ SEPTICEMIC: NO
HOW MANY PEOPLE MAY HAVE BEEN IN CLOSE CONTACT WITH
    PATIENT IN LAST 14 DAYS: 0 TO 5
ATTEMPT MADE TO TRACE CONTACTS AND OFFER PROPHYLAXIS: YES
ANY CONTACT REFUSED PROPHYLAXIS: NO
ANY CONTACT DEVELOPED ILLNESS CONSEQUENTLY: NO
ANY OTHER PATIENT WITH SEPTICEMIC/ SEVERE PNEUMONIA/ BUBOES
    SEEN BY YOU, OR IS KNOWN TO HAVE OCCURRED IN YOUR
    FACILITY: YES
WHICH TYPE: SEVERE PNEUMONIA
HAS PLAGUE BEEN DEFINITELY EXCLUDED IN THIS PATIENT: YES
HOW: ALTERNATIVE DIAGNOSIS, LAB CONFIRMED
WHICH ONE: LEGIONELLA
ANY DEATHS IN YOUR FACILITY IN THE RECENT PAST THAT MAY BE
    ATTRIBUTED TO PLAGUE: NO
IF YOU ENCOUNTER ANY PATIENT WITH PLAGUE LIKE FEATURES,
    PLEASE FILL IN PLAGUE SUSPECT CASE QUESTIONAIRRE AND
    ORDER LAB TEST: PCR FOR PLAGUE URGENTLY: OK
FOR MORE INFORMATION ON PLAGUE, CALL 1-800-SYS-0000: OK

*FIG. 17B*

SEARCH ENGINE REPORT
SUMMARY SEARCH 1: PLAGUE LIKE FEATURES
SEARCH FOR ALTERED SENSORIUM PROGRESSING TO DEATH: CAUSE
UNKNOWN- IN COUNTY ALPHA: 0 RESULTS
SEARCH FOR INGUINAL/ AXILLARY BUBOES YIELDED: 1 RESULT
SEARCH FOR SEVERE PNEUMONIA PROGRESSING TO DEATH-
UNKNOWN CAUSE- IN COUNTY ALPHA: 0 RESULTS
STATUS: ACTIVELY RUN IN BACKGROUND. ALERT IF ANY POSITIVES

SUMMARY SEARCH 2: ACUTE UPPER RESPIRATORY INFECTION:
RANKING OF ALPHAVILLE MED.CENTER VIS-A-VIS ENTIRE COUNTY: 44
OF 89
RANKING OF CLUSTER OF ALPH. MED. CENTRE VIS-A-VIS REST OF
COUNTY: 5 OF 11 CLUSTERS
RANKING OF COUNTY ALPHA VIS-À-VIS STATE: 21 OF 35 COUNTIES.

MAPPING ENGINE REPORT
RAW MAP CREATED AT 16.50 HRS.
BUFFERED MAPS NOT REQUISITIONED BY ANALYST.
REASON GIVEN: ONLY ONE CASE.
STATUS: ACTIVELY RUN IN BACKGROUND. ALERT IF ANY POSITIVES

NEW SCRIPT PARAMETERS
GEOGRAPHICAL COVERAGE: ENTIRE COUNTY ALPHA
TYPE OF REPORTING LOCATIONS: ALL
TIME SINCE SCRIPTS DISPATCHED: 2:48 HRS
RESPONSE RATE: 23%
ANY CASE OF DEATHS DUE TO UNKNOWN CAUSE IN THE LAST 2
WEEKS: NO=95, YES= 0
ANY POSITIVE MICROBIOLOGY TEST FOR YERSINIA PESTIS: NO=94,
YES=1
FACILITY ID REPORTING POSITIVE: ALPHAVILLE MED. CENTER.
ANY PATIENTS WITH PLAGUE IN THE DIFFERENTIALS: NO=94, YES=1
FACILITY ID REPORTING POSITIVE: ALPHAVILLE MED. CENTER.

PROTOCOL PARAMETERS
ALTERATIONS LAST MADE ON 14|JULY 2002 AT 1103 HRS.

AVAILABLE OPTIONS (PLEASE CHOSE ONE):
   1. STATUS QUO
   2. WAIT TILL RESPONSES RATE REACHES ___%
   3. REFER TO REGIONAL HEALTH AUTHORITY
   4. TERMINATE ALL FURTHER ANALYSES
   5. REMIND ME AGAIN IN ___ HOURS. FOLLOW UP FOR ___ WEEKS

*FIG. 17C*

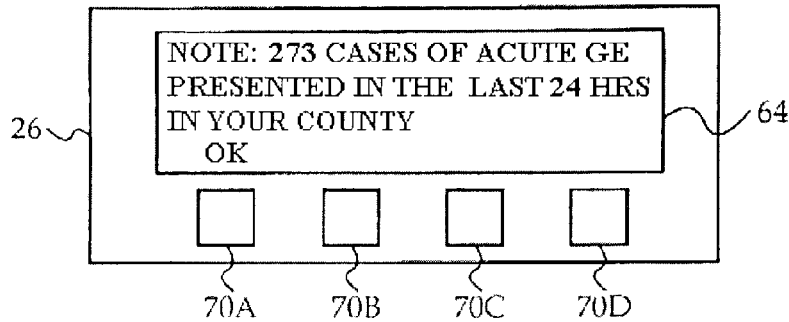
FIG. 19
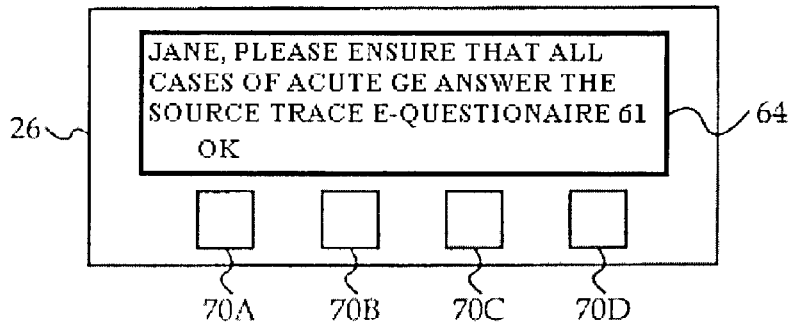
FIG. 20
FIG. 21

PUBLIC HEALTH SURVEILLANCE SYSTEM

PRIORITY CLAIM

This application is a Continuation-In-Part of U.S. Ser. No. 10/233,296 filed Aug. 30, 2002, currently pending, which is a Continuation-In-Part of U.S. Ser. No. 09/237,194 filed Jan. 26, 1999, currently pending, which is a Continuation of U.S. Ser. No. 08/481,925 filed Jun. 7, 1995, now U.S. Pat. No. 5,899,855, which is a Continuation of U.S. Ser. No. 08/233,397 filed Apr. 16, 1994, now abandoned, which is a Continuation-In-Part of U.S. Ser. No. 07/977,323 filed Nov. 17, 1992, now U.S. Pat. No. 5,307,263.

FIELD OF THE INVENTION

This invention relates generally to remote health monitoring systems, as applied to the field of public health surveillance. In particular, it relates to a multi-user remote health monitoring system that is capable of reliably identifying healthcare providers and collecting data from frontline healthcare providers, laboratory and hospital information systems, and individual patients in a number of ways, with a view to aid in the field of public health. The system can also be used to query both healthcare providers, and the patients regarding specifics pertaining to the health of the patients, and for patient tracking, monitoring, and the collection of patient data.

BACKGROUND OF THE INVENTION

Critical gaps exist in our nation's ability to anticipate, detect and respond to epidemics that may be 'natural' or that which may be attributed to bioterrorism due to ineffective disease surveillance and fragmented information systems. Federal, state, and local agencies urgently need (i) surveillance capabilities to accelerate time-to-detection and monitor preparedness at the local level, and (ii) integrated information solutions that enable rapid statistical analyses and facilitate investigations.

Surveillance systems should monitor the health of the population in real time and on a continuous basis. Many disease agents offer only a brief window between exposure and the onset of symptoms. In addition, many agents, like anthrax, cannot be successfully treated once the condition has become advanced but can be treated if caught early. Thus, the window of time during which effective intervention is possible can be very narrow. In order to facilitate rapid responses, surveillance systems must be capable of monitoring information on an ongoing basis. In order to intervene successfully to treat existing infections and prevent the onset of new ones, health surveillance systems should provide a continuous, real-time (or as near real-time as possible), and accurate overview of a population's health. Monitoring, and following up individuals who present themselves at healthcare facilities in both the emergency and the routine setting, and monitoring the results of laboratory and radiological investigations, routine hospital census information and autopsy reports of unexplained deaths would help accomplish this in real life.

Information systems that integrate data collected over multiple healthcare facilities and large populations enable dedicated public health analyst(s) at the Health Departments to attach significance to seemingly disparate events, and subsequently recognize the occurrence of a biological event far earlier than if it were done on an individual basis at an individual healthcare facility.

Current infectious disease reporting systems typically wait until the diagnosis of a specific disease before the care provider reports to the public health department. Crucial time is also lost from when a test is reported as positive to its report reaching the physician who ordered it. Many possible bioterrorism agents do not present with specific symptoms in the early stages of the disease and therefore are difficult to identify. This means that care providers have to wait until the disease has progressed to advanced stages before they report to the local health department. Given the contagious nature of many targeted diseases and the potential threat of cross contamination from biological agents, the early identification of biological attacks is imperative. The ability to quarantine or decontaminate exposed populations thereby preventing further dissemination of harmful agents will be greatly facilitated by the use of active surveillance and monitoring.

Last year, there were approximately 100 million emergency room visits in the United States. Therefore, each of the approximately 4,200 emergency rooms received on average of 66 visits per day, with some larger emergency departments at academic medical centers and major trauma centers experiencing greater than 150 visits per day. If the scope of surveillance is expanded to include physicians' offices, walk-in clinics, laboratory and radiological data, and hospital information systems the requirements for the successful collection of information on each patient's symptoms, become particularly challenging.

Many emergency care facilities currently participate in rudimentary active surveillance programs. These programs typically involve paper-based surveys that are faxed to a central county location for manual tabulation. In addition to their time consuming nature, paper-based surveys greatly reduce the ability to query discrete data elements, limit the ability to change the data elements collected in response to a new event, and are much more open to errors due to manual recording, tabulation and data entry.

For an active surveillance system to succeed, it must have the following characteristics: real time data collection, low burden of data entry and maintenance on healthcare providers, ability to dynamically respond to new information, ability to collect data from a wide range of settings (ERs, clinics, physicians' offices, laboratories, hospital information systems etc.), ability to aggregate data across jurisdictions and regions, ability to collect incrementally more information about high-risk patients, two way communication capabilities to provide immediate feedback and education to frontline healthcare providers. The invention described below enables public health officials do this in an inexpensive and convenient manner. In addition, the system may be used to automate components of standard hospital procedures/protocols, and save precious time to detection in case of the unfortunate occurrence of such an event.

SUMMARY OF THE INVENTION

The invention presents a networked system for remotely identifying, querying and monitoring the health related parameters of a plurality of individuals who present at healthcare facilities, and their respective healthcare providers, and for communicating information to same individuals, and public health workers for the purpose of disease surveillance. The system includes a server, and a workstation for entering into the server query sets to be answered by the individuals. The server is preferably a World Wide Web server and the workstation is preferably a personal computer or network terminal connected to the web server via a secure Internet connection. The system also includes a remotely programmable apparatus for identifying and interacting with the individuals. The remotely programmable apparatus is connected to the server via a communication network, preferably a secure Internet connection. The remotely programmable apparatus interacts with the individuals in accordance with script programs received from the server.

The server includes a script generator for generating script programs from the query sets, which are entered through the workstation. The script programs are executable by the remotely programmable apparatus to communicate the query sets to the individuals, to receive responses to the query sets, and to transmit the responses from the remotely programmable apparatus to the server. The server also includes a database connected to the script generator for storing the script program, and the responses to the queries. The database also stores a list of individuals or individual types, and for each individual or individual type, has a pointer to at least one script program. The server also has a report generator, an analytical engine that can retrieve stored responses and other information from the database, follow up on specific bits of information that fulfills certain criteria as determined by the operator, organize and numerically manipulate the dataset for the purpose of analysis, and represent the information contained therein in a pictorial form, such as a map, graph, chart, etc. Besides this, the analytical engine would also be capable of exporting the data after its conversion into widely used standardized formats such HL7 (Health Level Seven), LOINC (Logical Observation Identifiers, Names and Codes), SNOMED (Systematized Nomenclature of Human and Veterinary Medicine). The server also has script assignment means connected to the database, which assigns to an individual at least one script program, according to the script assignment information. The workstation allows a public health worker or a healthcare provider to enter in the script assignment information.

The remotely programmable apparatus has a communication device, such as a modem, for receiving the script programs from the server and for transmitting the responses to the server. The remotely programmable apparatus also has a user interface for communicating the query sets to the individuals and for receiving the responses to the query sets. In the preferred embodiment, the user interface includes a display for displaying the query sets and user input buttons for entering the responses to the query sets.

The remotely programmable apparatus also includes a memory for storing the script programs and the responses to the query sets. The remotely programmable apparatus further includes a microprocessor connected to the communication device, the user interface, and the memory. The microprocessor executes the script programs to identify the individual, communicate the query sets to the individual, receive the responses to the query sets, and transmit the responses to the server through the communication network.

In one embodiment, the system also includes at least one monitoring device for producing measurements of a health condition or parameter of a patient and for transmitting the measurements to the apparatus. The monitoring device can also be used to help the remotely programmable apparatus identify the individual operator. The remotely programmable apparatus includes a device interface connected to the microprocessor for receiving the measurements and information from the monitoring device. The measurements are stored in the memory and transmitted to the server along with the operator's identity and the responses to the query sets. The server also preferably includes a report generator connected to the database for generating a report of the measurements and responses. The report is displayed on the workstation.

In another embodiment, the system includes a monitoring application that is capable of acquiring data (responses and measurements) from either the remote apparatus or the database and use this data to select another script to be sent to one or more monitoring devices, not necessarily the one from which it received the said data, according to criteria that have been established in advance by the public health workers and/or healthcare providers.

As the present invention has multi-user capabilities, it must identify each individual or individual type in order to select the correct script program. In one embodiment, the individual can enter his or her unique identification code into the remotely programmable apparatus. The code is sent to the server and used to determine which script program to send back to the apparatus.

In another embodiment, the system uses a data card, which contains information about an individual's identity. The remotely programmable apparatus includes a data card reader in which the data card can be placed and read. A personal identification number (PIN) can also be used in conjunction with the data card in order confirm an individual's identity. In this embodiment, the present invention resembles an ATM machine.

The system of the present invention can also identify an individual by intercepting data from a separate information system. Data sent from a server of the separate information system to a printer can pass through the remotely programmable apparatus, which can identify the individual and send the data to the server of the present invention. Data passing through the remotely programmable apparatus can also trigger a script program, which can display queries for the individual to answer, or send information to the printer to be printed. An example of this embodiment has the remotely programmable apparatus located in series between an information system server and an information system printer. Alternatively, this data can also include that entered on the keyboard, that which is stored in the RAM, or that which is stored in a given set of files or a folder information system server. In any case, the data is captured by a software program and analyzed using the same set of rules as that above, to trigger a script on the apparatus.

In addition, the system would also have the capability of collecting data from a range of sources, such as Interactive Voice Response Systems, Internet based forms, wireless devices and the invention enabled monitoring appliances, and integrating the above data into the database, after conversion into the standardized format.

Finally, the data analysis methods, criteria for data segregation, and techniques and methods to automate several of the functions of the operator, in order to achieve quicker response times, reduced administration costs and reduction in the possibility of errors are described.

BRIEF DESCRIPTION OF THE DRAWINGS

FIG. 5 is a script entry screen according to the preferred embodiment of the invention.

FIG. 6A is a listing of a sample script program according to the preferred embodiment of the invention.

FIG. 6B is a continuation of the listing of FIG. 6A.

FIG. 7 is a script assignment screen according to the preferred embodiment of the invention.

FIG. 8 is a sample prompt appearing on a display of the apparatus of FIG. 3.

FIG. 10B is a sample healthcare facility report displayed on the workstation of the system of FIG. 1.

FIG. 17A is a sample analytical engine report created from the components of the embodiment in FIG. 15.

FIG. 17B is a continuation of FIG. 17A.

FIG. 17C is a continuation of FIG. 17B.

FIG. 19 is a first sample message, appearing on the display of the apparatus of FIG. 3.

FIG. 20 is a second sample message, appearing on the display of the apparatus of FIG. 3.

FIG. 21 is a script entry screen according to the third embodiment of the invention.

DETAILED DESCRIPTION OF THE PREFERRED EMBODIMENT

Figure 1:
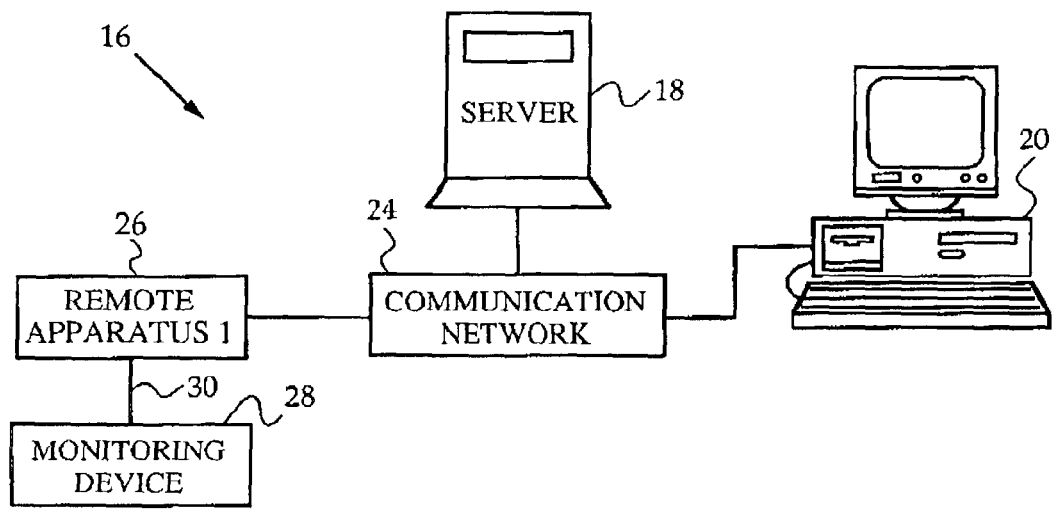
FIG. 1 is a block diagram of a networked system according to a preferred embodiment of the invention.

The preferred and alternative embodiments of the present invention are described in detail below with reference to the following drawings.

In view of the above, it is an object of the present invention to provide a simple and inexpensive system for identifying and remotely monitoring a plurality of patients who present at healthcare facilities, and information regarding their health status. It is another object of the present invention to provide a remote monitoring system, which incurs a minimal hardware cost. It is another object of the present invention to communicate information to a plurality of frontline healthcare providers such as physicians, triage nurses at emergency rooms, laboratory workers, radiologists, hospital information system entry operators, patients, and individuals who have been exposed to a disease causing agent. It is another object of the invention to provide a system which allows flexible and dynamic querying, and monitoring of a plurality of patients and/or individuals who have been exposed to disease causing agents. Another object of the present invention is to allow automatic identification of an individual operator or patient by the use of a data card, a remote monitoring device, or a separate information system. It is another object of the present invention to assign scripts to individuals and healthcare facilities automatically. It is a further object of the present invention to allow the collection and tracking of patient data, including the clinical history, physical examination findings, laboratory and radiological findings, and diagnoses from a plurality of patients, and from a plurality of healthcare facilities for statistical analysis. It is another object of the present invention to provide an interactive response system, which accepts and uses input from separate information systems, such as a hospital's general purpose, or laboratory information system. It is another object of the present invention to provide individualized healthcare provider and patient interaction, in case where a patient and/or individual exposed to a disease agent needs to be monitored, at a public terminal without increasing administration costs. It is another object of the present invention to automate components of the healthcare facility's patient, and disease management protocols, with a view to decrease administration costs and response, and follow-up times. It is a final object of the system to provide tools to public health workers and healthcare providers to analyze, and subsequently respond to the data acquired by the system.

These and other objects and advantages will become more apparent after consideration of the ensuing description and the accompanying drawings.

The invention presents a system and method for the identification of, and the timely collection of data relating to public health from healthcare facilities for the purpose of surveillance, and for communicating information to frontline healthcare professionals. In a preferred embodiment of the invention, the individuals (operators) are healthcare professionals at Emergency Departments of healthcare facilities and the system is used to collect data relating to the chief complaints of all the patients presenting in this setting. In another embodiment of the invention, the operator is a laboratory worker at a microbiology, pathology, forensic, medico-legal, biochemistry, immunology or molecular biology laboratory, or a data entry operator at the healthcare facility's laboratory, the radiology information system and/or the healthcare facility's reception or billing section. In this embodiment, the information collected also includes the specific laboratory parameters and radiological findings of the patient.

Public Health Analysts can use the data thus collected for monitoring the health status of the community at any given point of time, in detecting epidemics early, in following up patients who have presented within a certain timeframe with a given set of complaints, in planning for contingencies, and for research purposes. The invention may be further used in tracing the source of the epidemic, through used of an electronic questionnaire, to be administered to all the patients, and/or his or her attendants in either the in-patient or the ambulatory setting. The invention may also be given to patients and their contacts that have been exposed to a disease-causing agent as a convenient means for their monitoring in the ambulatory setting. Further, the invention may be used in conjunction with laboratory diagnostic equipment, and routine inputted information at the laboratory and radiological information systems such as PACS (Picture Archiving and Communication Systems) and/or any other hospital and health care facility information system for sentinel surveillance. In this case, positive laboratory tests, and results that are predefined to be of potential significance in the realm of public health are used to trigger a series of queries, which may, in addition be dynamically updated, to be answered by the healthcare professional.

In the present invention, an operator is designated to mean a frontline healthcare professional such as the triage nurse at the Emergency Department of a healthcare facility, a physician treating patients in either the elective or emergency setting, a laboratory worker at either the healthcare facility's laboratory or that of a dedicated microbiology, pathology, biochemistry, forensic, immunology or molecular laboratory, and personnel at medico-legal and pathological autopsy units. Besides the above, an alternative embodiment of the invention may be implemented at the healthcare facility's receptions, billing sections, laboratory, and radiological information systems. Also, it is to be understood that the invention is not limited to remotely serving questionnaires to healthcare professionals, patients, or follow up. The invention may also be implemented as an automated messaging system for communicating information and alerts to healthcare personnel and patients, as will be discussed in an alternative embodiment below.

A preferred embodiment of the invention is illustrated in FIGS. 1-12. Referring to FIG. 1, a networked system 16 includes a server 18 and a workstation 20 connected to server 18 through a communication network 24. The server 18 is preferably a World Wide Web server and the communication network 24 is preferably the Internet. It will be apparent to one skilled in the art that the server 18 may comprise a single stand-alone computer or multiple computers distributed throughout a network. The workstation 20 is preferably a personal computer, remote terminal, or web TV unit connected to the server 18 via the Internet. The workstation 20 functions as the workstation for entering in the server 18 messages and queries to be communicated to individuals.

The system 16 also includes a remotely programmable apparatus 26 for communicating with healthcare providers and patients. The apparatus 26 is designed to interact with a plurality of individuals in accordance with script programs received from the server 18. The apparatus 26 is in communication with the server 18 through the communication network 24, preferably the Internet. Alternatively, the apparatus 26 may be placed in communication with the server 18 via wireless communication networks, cellular networks, telephone networks, or any other network which allows apparatus 26 to exchange data with the server 18. For clarity of illustration, only one apparatus 26 is shown in FIG. 1. It is to be understood that the system 16 may include any number of apparatuses, with each apparatus used to retrieve responses from any number of individual operators, in this case, triage nurses, physicians, laboratory personnel, patients and their contacts. In the preferred embodiment, each healthcare facility's Emergency Department, and laboratories are provided with a monitoring device 28 in communication with the remote apparatus 26 via connecting cables 30.

Figure 2:
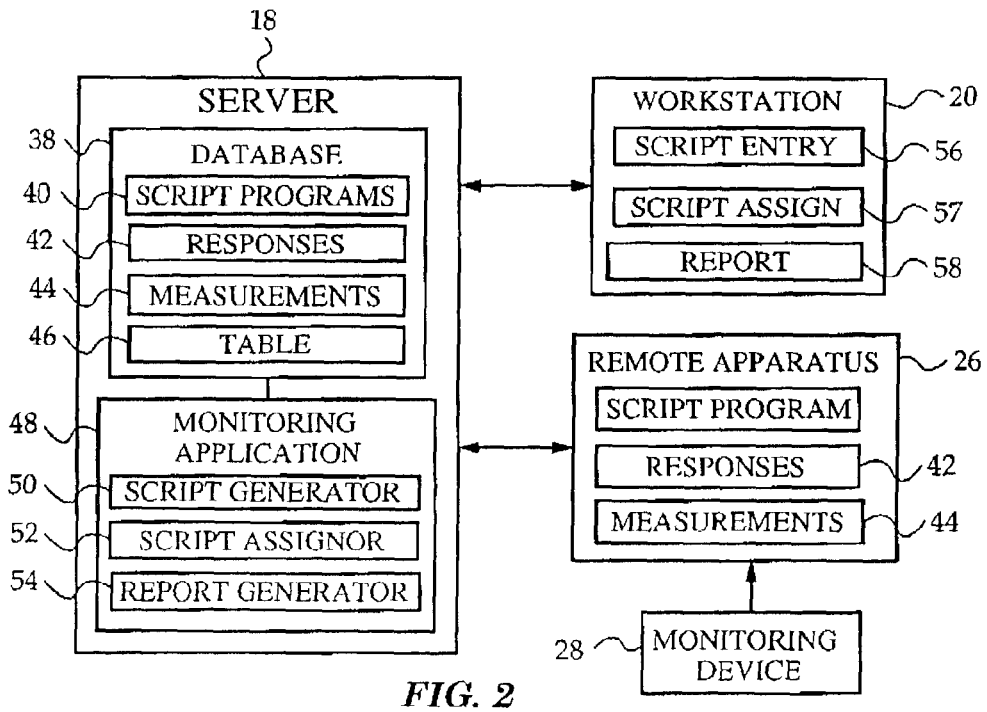
FIG. 2 is a block diagram illustrating the interaction of the components of the system of FIG. 1.

FIG. 2 shows the server 18, the workstation 20, and the apparatus 26 in detail. The server 18 includes a database 38 for storing script programs 40. The script programs 40 are executed by the apparatus 26 to communicate queries and messages to the operator, receive responses 42 to the queries, collect monitoring device measurements 44, and transmit the responses 42 and the measurements 44 to the server 18. The database 38 is designed to store responses 42 and measurements 44. The database 38 further includes a look-up table 46. The table 46 contains a list of healthcare facilities, and the data sources within the healthcare facilities that provide data inputs into the surveillance system, and for each facility, data entry point and operator within the system, a unique operator identification code and a respective pointer to the script program is assigned. Each apparatus 26 is designed to execute assigned script programs 40 which it receives from the server 18. As each apparatus 26 may be used by a number of operators at any given facility, the apparatus 26 can execute any number of script programs 40.

Figure 3:
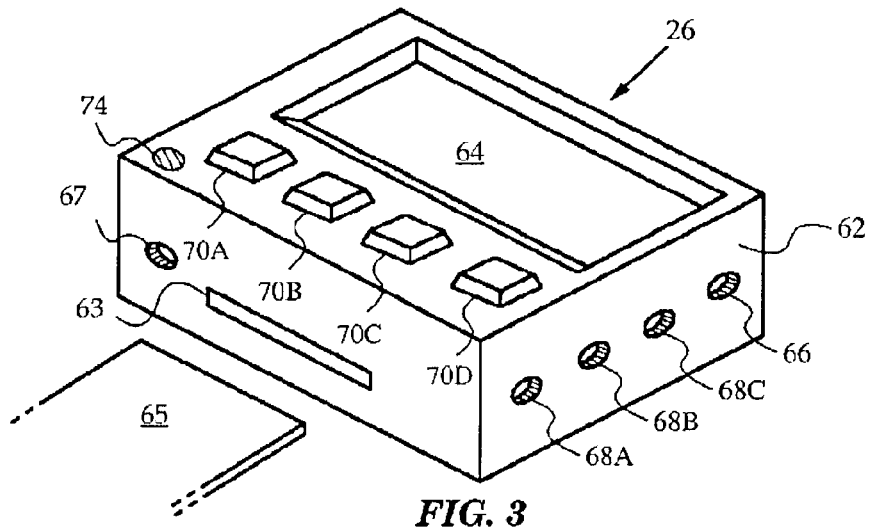
FIG. 3 is a perspective view of a remotely programmable apparatus of the system of FIG. 1.
Figure 4:
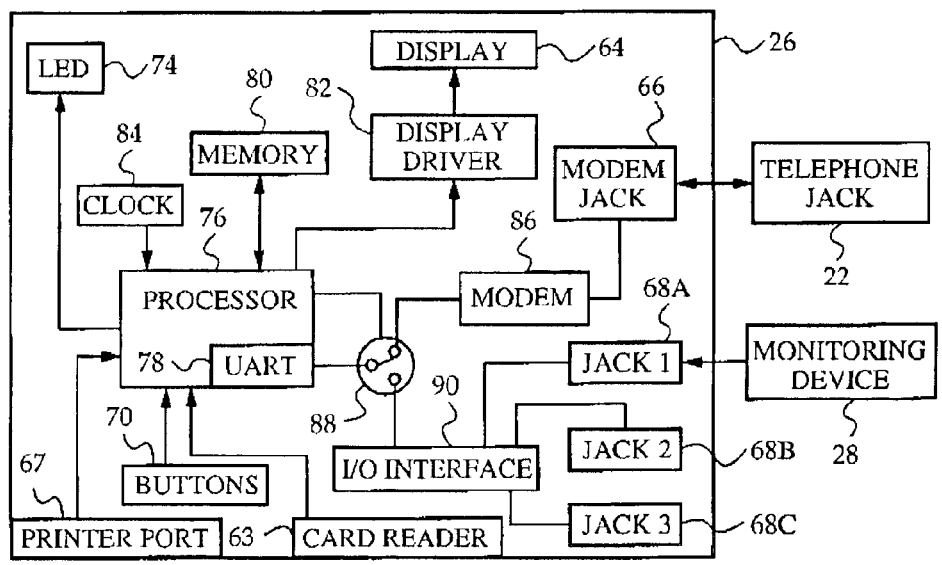
FIG. 4 is a block diagram illustrating the components of the apparatus of FIG. 3.

FIGS. 3-4 show the structure of each apparatus 26 according to the preferred embodiment. Referring to FIG. 3, the apparatus 26 includes a housing 62. The housing 62 is sufficiently compact to enable the apparatus 26 to be placed unobtrusively on the triage center counter, or beside the laboratory instrument. The apparatus 26 also includes a display 64 for displaying queries and prompts to the operator. In the preferred embodiment, the display 64 is a liquid crystal display (LCD).

In another embodiment, the housing 62 may be so designed to include not only the apparatus 26, but also the monitoring device 28 within.

Four user input buttons 70A, 70B, 70C, and 70D are located adjacent to the display 64. User input buttons 70A, 70B, 70C, and 70D are for entering in the apparatus 26 responses to the queries and prompts. In the preferred embodiment, user input buttons 70A, 70B, 70C, and 70D are momentary contact push buttons. In alternative embodiments, the user input buttons 70A, 70B, 70C, and 70D may be replaced by switches, keys, a touch sensitive display screen, or any other data input device.

Three monitoring device jacks 68A, 68B, and 68C are located on a surface of housing 62. Device jacks 68A, 68B, and 68C are for connecting the apparatus 26 to a number of monitoring devices 28, such as digital thermometers, sphygmomanometers, Automated PCR equipment, microbiological culture CO2 detectors, automated chemical and toxicological analyzers, etc through respective connection cables (not shown). The apparatus 26 also includes a modem jack 66 for connecting the apparatus 26 to a telephone jack through a standard connection cord (not shown). The apparatus 26 further includes a visual indicator, such as a light emitting diode (LED) 74. The LED 74 is for visually notifying the operator that he or she has unanswered queries stored in the apparatus 26. The apparatus 26 also contains a data card reader 63. The data card reader 63 is capable of reading a data card 65 containing information about an operator and the healthcare facility. In the present invention, the data card 65 contains the identity of the operator, the healthcare facility, and the respective authentication codes. The data card 65 is placed in the data card reader 63, thus allowing the apparatus 26 to identify the operator and assign the script program 40. The apparatus 26 also has a printer port 67, allowing the apparatus 26 to be directly connected to a printer. Queries 94, responses 42, device measurements 44, and other pertinent information stored on the apparatus 26 can be printed directly.

FIG. 4 is a schematic block diagram illustrating the components of the apparatus 26 in detail. The apparatus 26 includes a microprocessor 76, and a memory 80 connected to the microprocessor 76. The memory 80 is preferably a non-volatile memory, such as a serial EEPROM. The memory 80 stores script programs 40 received from the server 18, measurements 44 received from the monitoring device 28, responses to queries, and an operator or data source type's unique identification code. The microprocessor 76 also includes built-in read only memory (ROM, which stores firmware) for controlling the operation of the apparatus 26. The firmware includes a script interpreter used by the microprocessor 76 to execute script programs 40. The script interpreter interprets script commands, which are executed by the microprocessor 76.

The script commands allow apparatus 26 to identify the operator through user buttons 70A, 70B, 70C, and 70D, the monitoring device 28, the data card 65, or the printer port 67. They also allow the apparatus 26 to display the query sets to the operator, receive responses 42 to the query sets, receive measurements 44 from the monitoring device 28, and transmit responses to the server 18. Specific techniques for interpreting and executing script commands in this manner are well known in the art.

The microprocessor 76 is preferably connected to the memory 80 using a standard two-wire I$^2$C interface. The microprocessor 76 is also connected to user input buttons 70A, 70B, 70C, and 70D, data card reader 63, printer port 67, LED 74, a clock 84, and a display driver 82. The clock 84 indicates the current date and time to the microprocessor 76. For clarity of illustration, the clock 84 is shown as a separate component, but is preferably built into microprocessor 76. The display driver 82 operates under the control of the microprocessor 76 to display information on the display 64. The microprocessor 76 is preferably a PIC 16C65 processor that includes a universal asynchronous receiver transmitter (UART) 78. The UART 78 is for communicating with a modem 86 and a device interface 90. A CMOS switch 88 under the control of the microprocessor 76 alternately connects modem 86 and interface 90 to UART 78.

The modem 86 is connected to a telephone jack 22 through the modem jack 66. The modem 86 is for exchanging data with the server 18 through the communication network 24. The data includes script programs 40 which are received from the server 18 as well as responses 42 to queries, device measurements 44, script identification codes, the operator's and healthcare facility's unique identification code, and authentication codes that the modem 86 transmits to the server 18. The modem 86 is preferably a complete 56 K modem commercially available from Cermetek, although any suitable modem may be used.

The device interface 90 is connected to the device jacks 68A, 68B, and 68C. The device interface 90 is for interfacing with a number of monitoring devices, such as blood glucose meters, blood pressure cuffs, or pulse rate monitors, and laboratory diagnostic equipment through the device jacks. The device interface 90 operates under the control of the microprocessor 76 to collect measurements 44 from the monitoring devices and to output the measurements to the microprocessor 76 for storage in the memory 80. In the preferred embodiment, the device interface 90 is a standard RS232 interface. For simplicity of illustration, only one device interface is shown in FIG. 4. However, in alternative embodiments, the apparatus 26 may include multiple device interfaces to accommodate monitoring devices 28 which have different connection standards.

Alternatively, modem 86 may be a WAP (wireless application protocol) enabled wireless modem that exchanges data with the server 18 through the wireless communication network 24, such as cellular phone networks, mobile pagers, and two-way radios. The communication network 24 can also include satellite phone networks, WLL (Wireless Local Loop) networks to access public switched telephone networks (PSTN) using radio signals as a substitute for hardwire connections, Virtual Private Networks, Bluetooth enabled networks, intra hospital local area paging networks and any other wireless network that allows secure encrypted data transmission. The device interface 90 and the device jacks 68A, 68B and 68C are replaced by suitable wireless protocol enabled the interface 90 and device jacks 68A, 68B and 68C. An advantage of this would be that it will allow the apparatus 26 and the monitoring device 28 to transmit and receive data from sources that are not stationed at a single location, such as First Responder Units, emergency medical technicians, patient transport units, and from underprivileged regions and those regions that are remote and inaccessible. In addition to this, the apparatus 26 and the housing 62, can be miniaturized to allow clinicians and allied healthcare providers to carry it on their person. This would greatly add to the functionality that may be built additionally into the system, besides adding to convenience of usage, and subsequent compliance.

Alternatively, the modem 86 may be a high speed cable modem, the device jacks 68A, 68B and 68C may be serial USB ports, and the communication network 24 a Local Area Network connected to the Internet. This embodiment will allow much faster data transmission, and that which is in real time. In addition, this embodiment decreases the expenses that may be incurred in the installation of the system in healthcare and laboratory facilities that have pre-established network systems.

Referring again to FIG. 2, the server 18 includes a monitoring application 48. The monitoring application 48 is a controlling software application executed by the server 18 to perform the various functions described below. The application 48 includes a script generator 50, a script assignor 52, and a report generator 54. The script generator 50 is designed to generate script programs 40 from script information entered through workstation 20. The script information is entered through a script entry screen 56. In the preferred embodiment, the script entry screen 56 is implemented as a web page on the server 18. The workstation 20 includes a web browser for accessing the web page to enter the script information.

In another embodiment, in addition to the above, design components common to apparatus 26 and the monitoring device 28 may be integrated, allowing a reduction in hardware and manufacturing costs. These include memory 80, clock 84, display 64, processor 76, buttons 70, interface 90, etc. In addition, components such as 68A are rendered redundant. Alternatively select components of apparatus 26 that are not already present in monitoring device 28 are integrated into processor 76, and integrated chip of monitoring device 28 in an embodiment hereafter referred to as monitoring device 28A. Monitoring device 28A enables monitoring device 28 to be used in the same manner as before, with the additional capability and functions of the apparatus 26. Thus, Monitoring device 28A enables in monitoring device 28 the additional capability to store, receive and execute script programs 40, collect responses 42 and measurements 44 in a manner similar to that described for apparatus 26. Advantages of the above alternative embodiments would be in terms of convenience of usage and saving of space, hardware requirements and costs.

FIG. 5 illustrates the script entry screen 56 as it appears on the workstation 20. The screen 56 includes a script name field 92 for specifying the name of the script program 40 to be generated. The screen 56 also includes entry fields 94 for entering query sets to be answered by an operator. Each entry field 94 has corresponding response choice fields 96 for entering response choices for the query. The screen 56 further includes check boxes 98 for selecting desired monitoring device 28, such as a thermometer, sphygmomanometer, Laboratory Diagnostic Equipment which may include an Automated PCR Device, a toxin and chemical sampling device, radiation dose measuring device (such as a Geiger Counter), from which to collect measurements 44.

The screen 56 additionally includes a connection time field 100 for specifying a prescribed connection time at which the apparatus 26 executing the script is to establish a subsequent communication link to the server 18. The connection time is preferably selected to be the time at which communication rates are the lowest, such as 3:00 AM. The apparatus 26 in different Healthcare facilities may be programmed to establish connection at different times of the day, in order to reduce the hardware requirements of communication network 24 and the server 18. During this connection time, the apparatus 26 transmits to the server 18 all responses 42 and device measurements 44 it has received during the day. During this same connection time, the apparatus 26 also receives from server 18 all script programs 40 it will need for the following day or until the next prescribed connection time. This store and forward feature of the apparatus 26 reduces communication expenses. However, if the number of patients being seen at a particular healthcare facility is large, or if an alert has been sounded about a particular epidemic and surveillance needs to be more active, or if the stored data exceeds a particular set value, or if the data received from the monitoring device 28 has been characterized as being of considerable import, or if the operator of the device determines so, or for any other reason, more than one connection can be made during the day in order to download necessary script programs 40. For instance, in case of an acute disaster in a nearby location, connection times may be set to update information on a two-hourly, or even on an hourly basis. The screen 56 also includes a CREATE SCRIPT button 102 for instructing the script generator 50 to generate the script program 40 from the information entered in the screen 56. The screen 56 further includes a CANCEL button 104 for canceling the information entered in screen 56. After consideration of the above description, it will be apparent to one skilled in the art that the server 18 may be programmed to establish a connection with the remote apparatus 26, and allow for the transmission of the script, and of information, if need be the case.

In the preferred embodiment, each script program 40 created by the script generator 50 conforms to the standard file format used on UNIX systems. In the standard file format, each command is listed in the upper case and followed by a colon. Every line in the script program 40 is terminated by a linefeed character {LF}, and only one command is placed on each line. The last character in script program 40 is a UNIX end of file character {EOF}.

Table 1 shows an exemplary listing of script commands used in the preferred embodiment of the invention.

TABLE 1

| SCRIPT COMMANDS Command Description | |
|---|---|
| CLS: {LF} | Clear the display. |
| ZAP: {LF} | Erase from memory the last set of query responses recorded. |
| LED: b {LF} | Turn the LED on or off, where b is a binary digit of 0 or 1. An argument of 1 turns on the LED, and an argument of 0 turns off the LED. |
| DISPLAY: {chars} {LF} | Display the text following the DISPLAY command. |

TABLE 1-continued

| SCRIPT COMMANDS Command Description | |
|---|---|
| INPUT: mmmm {LF} | Record a button press. The m's represent a button mask pattern for each of the four input buttons. Each m contains an "X" for disallowed buttons or an "O" for allowed buttons. For example, INPUT: OXOX {LF} allows the user to press either button #1 or #3. |
| WAIT: {LF} | Wait for any one button to be pressed, then continue executing the script program. |
| COLLECT: device {LF} | Collect measurements from the monitoring device specified in the COLLECT command. The user is preferably prompted to connect the specified monitoring device to the apparatus and press a button to continue. |
| NUMBER: aaaa {LF} | Assign a script identification code to the script program. The script identification code from the most recently executed NUMBER statement is subsequently transmitted to the server along with the query responses and device measurements. The script identification code identifies to the server which script program was most recently executed by the remote apparatus. |
| DELAY: t {LF} | Wait until time t specified in the DELAY command, usually the prescribed connection time. |
| CONNECT: {LF} | Perform a connection routine to establish a communication link to the server, transmit the operator, healthcare facility or data source type identification code, query responses, device measurements, and script identification code to the server, and receive and store a new script program. When the server instructs the apparatus to disconnect, the script interpreter is restarted, allowing the new script program to execute. |

The script commands illustrated in Table 1 are representative of the preferred embodiment and are not intended to limit the scope of the invention. After consideration of the ensuing description, it will be apparent to one skilled in the art that many other suitable scripting languages and sets of script commands may be used to implement the invention.

The script generator 50 preferably stores a script program template, which it uses to create each script program 40. To generate the script program 40, the script generator 50 inserts into the template the script information entered in the screen 56. For example, FIGS. 6A-6B illustrate sample script program 40 created by script generator 50 from the script information shown in FIG. 5.

The script program 40 includes identification commands to determine the identity of the operator and the healthcare facility, and data source type from user buttons 70A, 70B, 70C, and 70D, monitoring device 68A, 68B, and 68C, the card chip reader 64, the printer port 67, and display commands to display the queries and response choices entered in fields 94 and 96, respectively. The script program 40 also includes input commands to receive the responses 42 to the queries. The script program 40 further includes a collect command to collect device measurements 44 from monitoring device 28 specified in check boxes 98. It will be obvious to one skilled in the art that the script program 40 may be alternatively written such that it is always in the COLLECT mode from one or more of the monitoring apparatus 28. The script program 40 may also be written such that it establishes connection to the server 18, or it executes a new script if the collected parameter from the monitoring device 28 fulfills certain predetermined criteria. The advantage of this would be that whenever a certain test of high significance from the public health viewpoint is returned as positive, such as a positive toxicological analysis for an agent of chemical warfare, the device notifies the public health officials automatically, and without waiting for the routine next connection to be established. The script program 40 also includes commands to establish a subsequent communication link to the server 18 at the connection time specified in the field 100. The steps included in script program 40 are also shown in the flow chart of FIGS. 12A-12B and will be discussed in the operation section below.

Referring again to FIG. 2, script assignor 52 is for assigning script programs 40 to the healthcare facilities. Script programs 40 are assigned in accordance with script assignment information entered through workstation 20. The script assignment information is entered through a script assignment screen 57, which is preferably implemented as a web page on server 18. FIG. 7 illustrates a sample script assignment screen 57 as it appears on workstation 20. Screen 57 includes check boxes 106 for selecting script program 40 to be assigned and check boxes 108 for selecting the healthcare facility types, and data source types to which script program 40 is to be assigned. The healthcare facility, and data source to which a script is assigned may be one that has reported cases of a particular syndrome, or all the healthcare facilities within a particular locality, or a laboratory that has obtained a positive test result of significance, or all the patients who have been exposed to a certain disease causing agent. It would also be possible to assign scripts to groups of individuals by allowing the script assignor program to retrieve from the database a list of all those individuals and healthcare facilities that fulfill certain criteria. Screen 57 also includes an ASSIGN SCRIPT button 112 for entering the assignments. When the button 112 is pressed, the script assignor 52 creates and stores for each healthcare facility or data source type selected in check boxes 108 a respective pointer to the script program 40 selected in check boxes 106. Each pointer is stored in the specific healthcare facility's or the data source's look-up table 46 of the database 38. The script assignment screen 57 further includes an ADD SCRIPT button 110 for accessing the script entry screen 56 and a DELETE SCRIPT button 114 for deleting the script program 40.

Figure 10A:
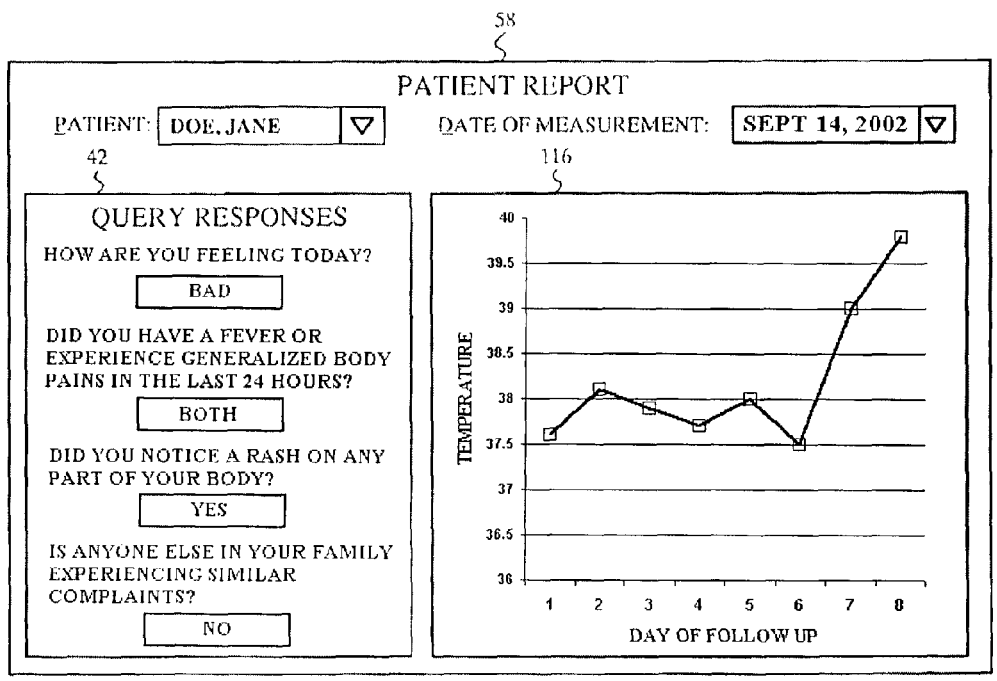
FIG. 10A is a sample patient report displayed on the workstation of the system of FIG. 1.

Referring again to FIG. 2, the report generator 54 is designed to generate a surveillance report 58 from the responses and device measurements received in the server 18. The surveillance report 58 is displayed on the workstation 20. FIG. 10A shows a sample surveillance report 58 produced by the report generator 54 for a selected patient on follow up. The surveillance report 58 includes a graph 116 of device measurements 44, as well as a listing of responses 42 received from the individual patient. FIG. 10B is similar to FIG. 10A save that it shows summarized data for the entire healthcare facility.

Figure 11A:
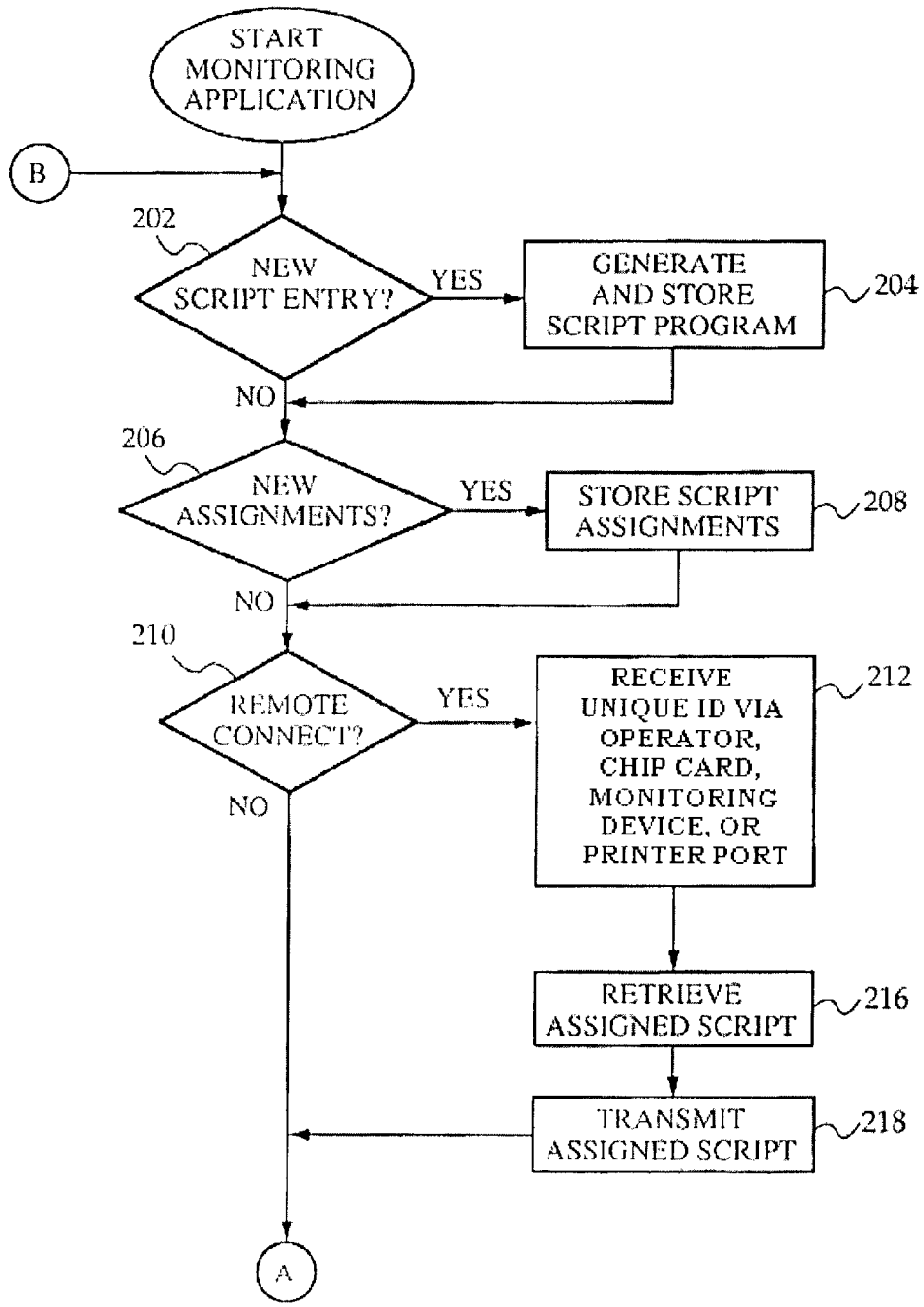
FIG. 11A is a flow chart illustrating the steps included in a monitoring application executed by the server of FIG. 1 according to the preferred embodiment of the invention.
Figure 11B:
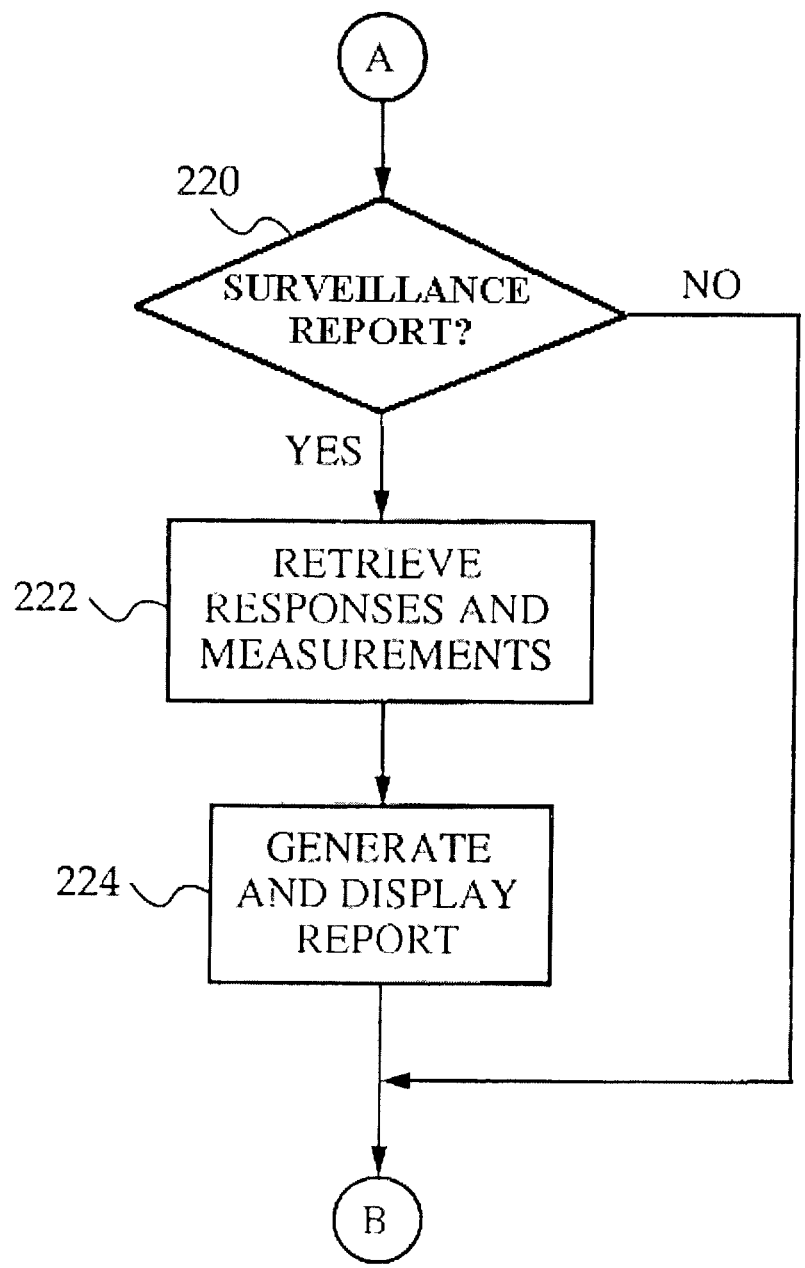
FIG. 11B is a continuation of the flow chart of FIG. 11A.

The operation of the preferred embodiment is illustrated in FIGS. 11A and 11B. FIG. 11A is a flow chart illustrating steps included in the monitoring application executed by the server 18. FIG. 11B is a continuation of the flow chart of FIG. 11A. In step 202, the server 18 determines if new script information has been entered through the script entry screen 56. If new script information has not been entered, the server 18 proceeds to step 206. If new script information has been entered, the server 18 proceeds to step 204.

As shown in FIG. 5, the script information includes queries 94, and for each query 94, corresponding responses choices 96. The script information also includes one or more selected monitoring device types from which to collect the device measurements 44. The script information further includes a prescribed connection time for each apparatus to establish a subsequent communication link to the server 18. A public health analyst generally enters the script information in the server 18. Of course, any person desiring to communicate with the operators may also be granted access to server 18 to create and assign the script programs 40. Further, it is to be understood that the system may include any number of workstations 20 for entering script generation and script assignment information in the server 18.

In step 204, the script generator 50 generates the script program 40 from the information entered in the screen 56. The script program 40 is stored in the database 38. Steps 202 and 204 are preferably repeated to generate multiple script programs, e.g. a script program for the fever with rash group of patients, a script program for the patients with shortness of breath, a script program for queries when a certain cerebrospinal fluid specimen is positive for gram positive rods, etc. Each script program 40 corresponds to a respective one of the sets of queries 94 entered through the script entry screen 56. Following step 204, the server 18 proceeds to step 206.

In step 206, the server 18 determines if new script assignment information has been entered through the assignment screen 57. If new script assignment information has not been entered, the server 18 proceeds to step 210. If new script assignment information has been entered, the server 18 proceeds to step 208. As shown in FIG. 7, the script programs 40 can be assigned by individual healthcare facility or data source, by a group of healthcare facilities, individuals, data sources that fulfill certain criteria, such as by location, previously reported findings, etc, by selecting the script program 40 through the check boxes 106, selecting the individual or group of healthcare facility or data source types to whom selected the script program 40 is to be assigned through the check boxes 108, and pressing the ASSIGN SCRIPT button 12. When the button 112 is pressed, the script assignor 52 creates for each healthcare facility selected in check boxes 108 a respective pointer to script program 40 selected in check boxes 106. In step 208, each pointer is stored in the look-up table 46 of the database 38. Following step 208, server 18 proceeds to step 210. In step 210, server 18 determines if apparatus 26 is remotely connected to server 18. If not, server 18 proceeds directly to step 220, as shown in FIG. 11B. If the apparatus 26 is connected, the server 18 receives from the apparatus 26 the operator's and healthcare facility's unique identification code in step 212. This step can be achieved in a number of ways. The operator can answer specific queries on display 64 of apparatus 26, which allows identification of the operator, the data input setting and the healthcare facility. The above information can also be obtained via the monitoring device 28. The monitoring device 28 can contain the data input setting and the facility's unique identification code, and can send it to the apparatus 26. The apparatus 26 is also capable of recognizing the type of monitoring device 28, for example laboratory diagnostics equipment, to determine the nature of the source, for example the arterial blood gas analysis machine of a laboratory.

The data card reader 63 is a third way in which the apparatus 26 can recognize an operator, the input setting and healthcare facility. The data card 65 contains information about the operator's and healthcare facility's identity, and data input setting information, which can be read by the data card reader 63 of the apparatus 26. This information is then sent to the server 18, where it is used to determine which script program 40 is sent back to the apparatus 26 to which the operator is to respond.

A fourth way in which the apparatus 26 can identify an operator and the data input setting is through the printer port 67, as illustrated in FIG. 20. Operator's data from the server 106 of another information system can be sent to the printer 108 via the apparatus 26. that sends the intercepted data to the server 18 of the remote monitoring system of the present invention, which can then send appropriate script program 40 to the apparatus 26. A more detailed description of the data interception embodiment of the present invention is described below.

A fifth way by which identification may be achieved is by means of the Caller Identification function implemented at the server 18. The server 18 may be programmed to identify the apparatus 26 by identifying the telephone number of the line which the apparatus 26 uses to make a connection with the server 18.

In step 216, the server 18 uses the operator's identification code to retrieve from the table 46 the pointer to script program 40 assigned to the operator, the healthcare facility, and the data input setting. Server 18 then retrieves assigned script program 40 from the database 38. In step 218, the server 18 transmits assigned script program 40 to the healthcare facility's apparatus 26 through the communication network 24. Following step 218, the server 18 proceeds to step 220, as shown in FIG. 11B.

In step 220, the server 18 determines if a report request has been received from the workstation 20. If no report request has been received, the server 18 returns to step 202. If a report request has been received for a selected data source, the server 18 retrieves from the database 38, measurements 44 and query responses 42 last received from the source, as shown in step 222. In step 224, the server 18 generates and displays the generated report 58 on the workstation 20. As shown in FIG. 10A, the report 58 includes device measurements 44 and query responses 42 last received from the data source. Following step 224, the server returns to step 202.

Figure 12A:
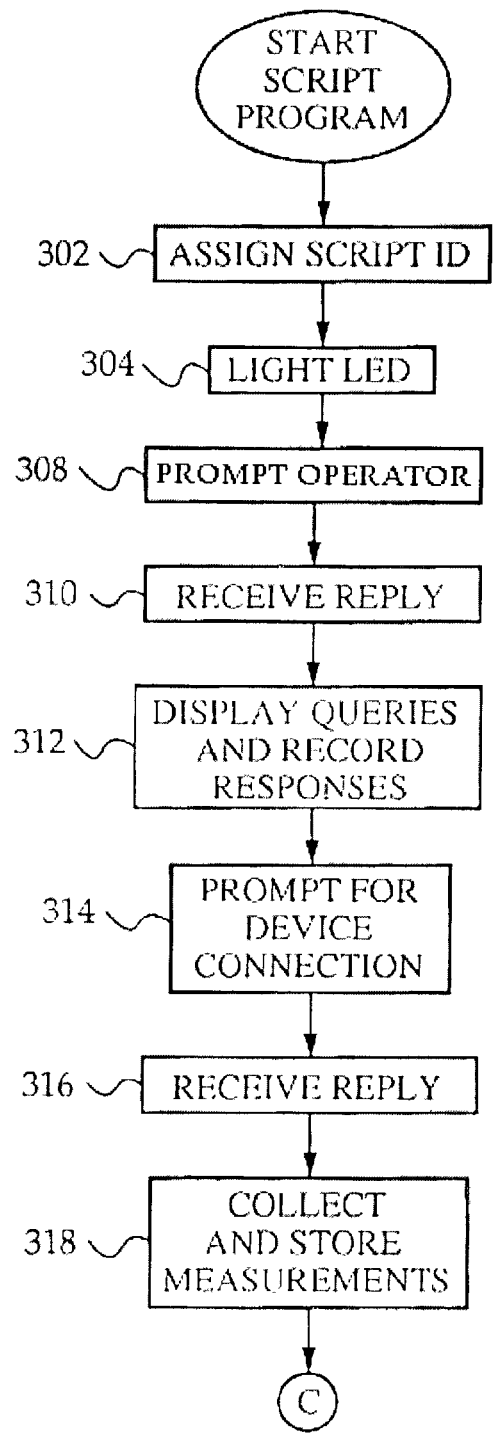
FIG. 12A is a flow chart illustrating the steps included in the script program of FIGS. 6A-6B.
Figure 12B:
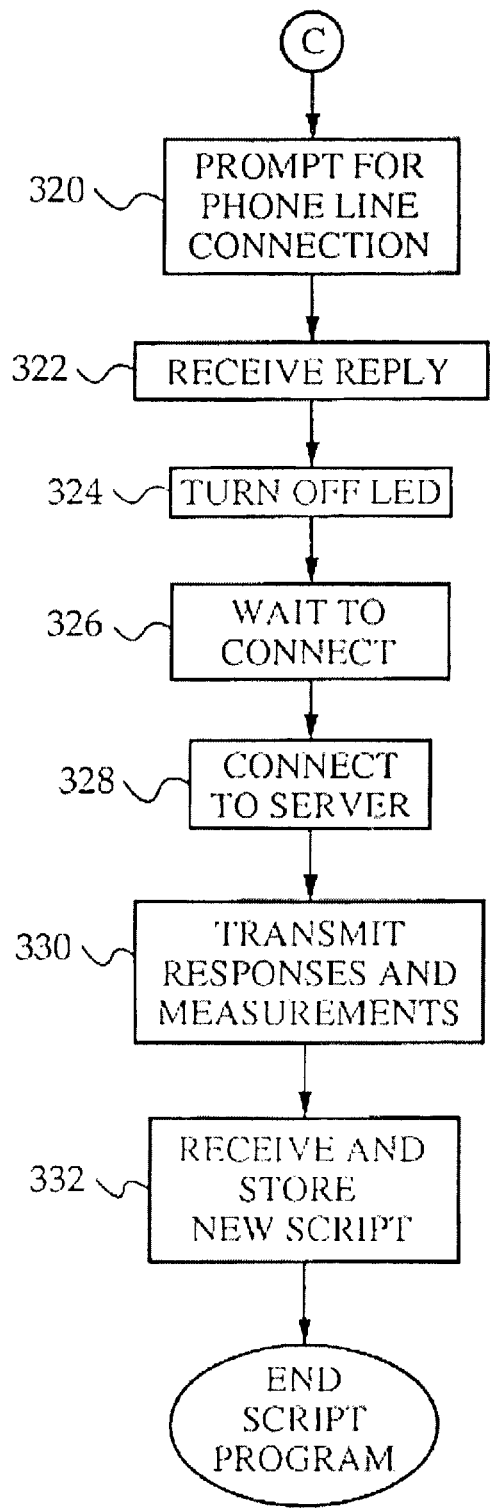
FIG. 12B is a continuation of the flow chart of FIG. 12A.

FIGS. 12A-12B illustrates the steps included in the script program 40 executed by the apparatus 26. Before the script program 40 is received, the apparatus 26 receives the operator's, healthcare facility's and data source's unique identification code, and is programmed with the script interpreter used by the microprocessor 76 to execute the script program 40. The initial programming may be achieved during the connection to the server 18. Following initial programming, the apparatus 26 receives from the server 18 the script program 40 assigned to the data source associated with the apparatus 26. The script program 40 is received by the modem 86 through a first communication link and stored in the memory 80.

Figure 14A:
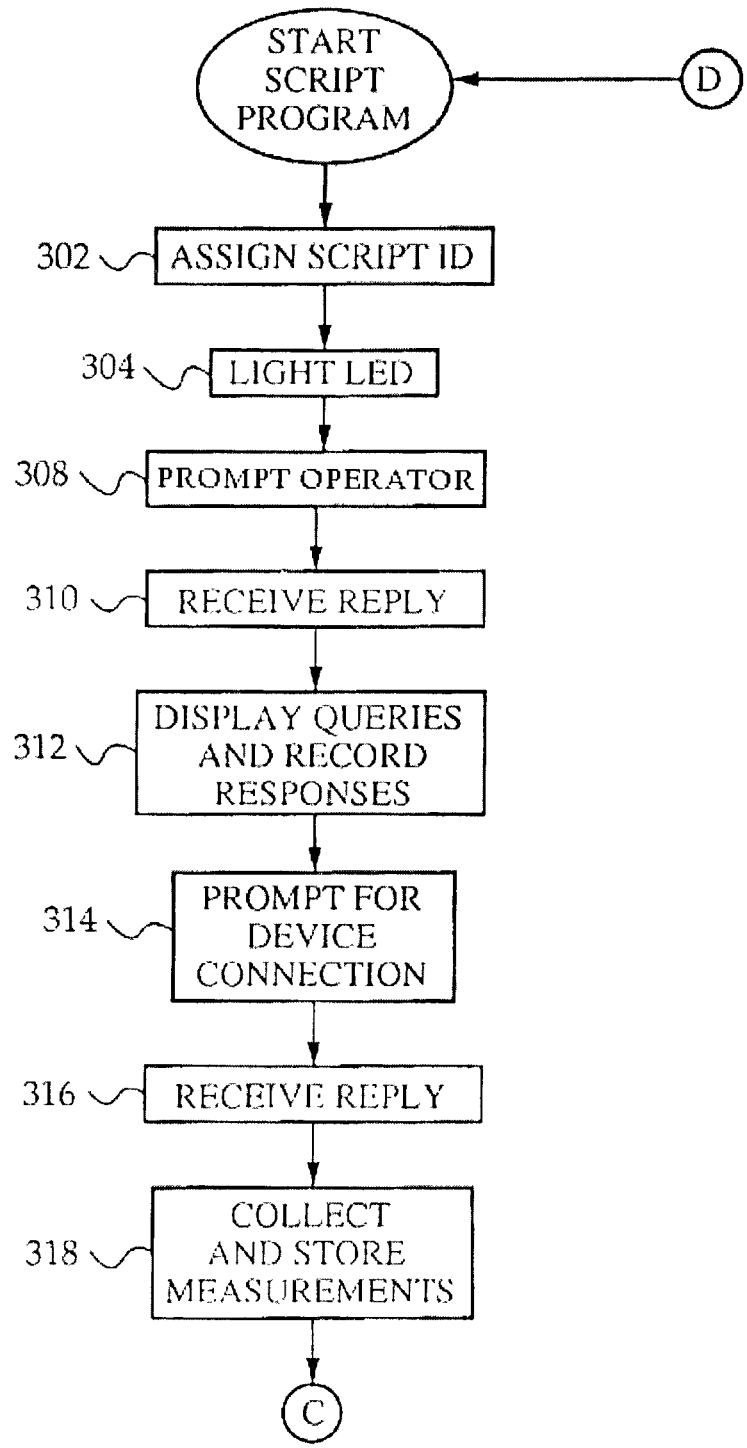
FIG. 14A is a flow chart illustrating the steps included in the script program used in the alternative embodiment of the invention.

FIG. 14A illustrates the starting of the script program. In step 302, the microprocessor 76 assigns a script identification code to script program 40 and stores the script identification code in memory 80. In step 304, the microprocessor 76 lights LED 74 to notify the operator that he or she has unanswered queries stored in apparatus 26. The LED 74 preferably remains lit until the operator answers the queries.

In step 308, the microprocessor 76 prompts the operator by displaying on display 64 "ANSWER QUERIES NOW? PRESS ANY BUTTON TO START". In step 310, microprocessor 76 waits until a reply to the prompt is received from the operator. When a reply is received, the microprocessor 76 proceeds to step 312. In step 312, the microprocessor 76 executes successive display and input commands to display the queries and response choices on display 64 and to receive responses 42 to the queries.

FIG. 8 illustrates a sample query and its corresponding response choices as they appear on display 64. The response choices are positioned on display 64 such that each response choice is located proximate to a respective one of input buttons 70A, 70B, 70C, and 70D. In the preferred embodiment, each response choice is displayed immediately above respective the input button 70. The operator presses input button 70A, 70B, 70C, or 70D corresponding to his or her response. The microprocessor 76 stores each response in the memory 80.

Figure 9:
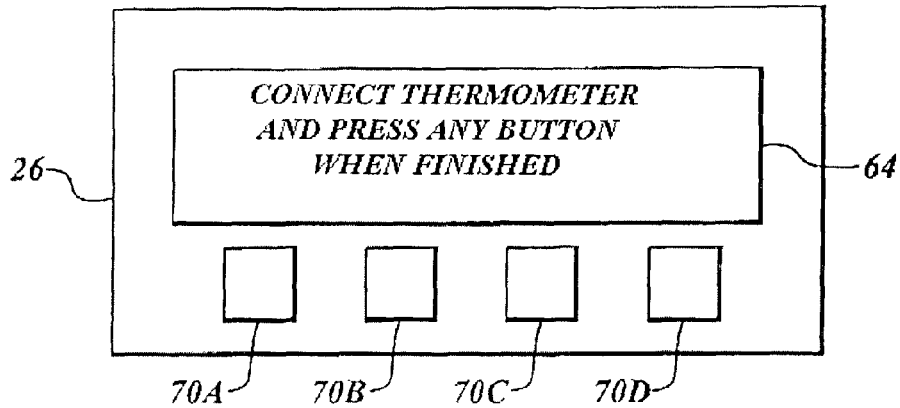
FIG. 9 is a sample query displayed on a workstation of the system of FIG. 3.

Returning to FIG. 14A, steps 314, 316, and 318, the microprocessor 76 executes commands to collect device measurements 44 from selected monitoring device 28 if it is directed to do so by the script program 40. The script program 40 specifies selected monitoring device 28 from which to collect measurements 44. In step 314, the microprocessor 76 prompts the operator to connect selected monitoring device 28, for example a blood glucose meter, or a clinical laboratory parameter-measuring instrument to one of device jacks 68A, 68B, and 68C. This step is rendered redundant in case monitoring device 28 is always connected to apparatus 26. A sample prompt is shown in FIG. 9. The operator presses input button 70A, 70B, 70C, or 70D corresponding to his or her response. The microprocessor 76 stores each response in the memory 80. In step 316, microprocessor 76 waits until a reply to the prompt is received from the operator. When a reply is received, the microprocessor 76 proceeds to step 318. The microprocessor 76 also connects the UART 78 to interface 90 through the CMOS switch 88. In step 318, the microprocessor 76 collects device measurements 44 from monitoring device 28 through the interface 90. Measurements 44 are stored in the memory 80.

In the preferred embodiment, the apparatus 26 is always plugged into the telephone jack 22. If not, however, the microprocessor 76 prompts the operator to connect the apparatus 26 to the telephone jack 22 so that the apparatus 26 may connect to the server 18 at the prescribed connection time, as depicted in step 320 of FIG. 12B. In step 322, the microprocessor 76 waits until a reply to the prompt is received from the operator. When a reply is received, the microprocessor 76 turns off the LED 74 in step 324. In step 326, the microprocessor 76 waits until it is time to connect to the server 18. The microprocessor 76 compares the connection time specified in the script program 40 to the current time output by the clock 84. When it is time to connect, the microprocessor 76 connects the UART 78 to the modem 86 through the CMOS switch 88.

In step 328, the microprocessor 76 establishes a subsequent communication link between the apparatus 26 and the server 18 through the modem 86 and the communication network 24. If the connection fails for any reason, the microprocessor 76 repeats step 328 to get a successful connection. In step 330, the microprocessor 76 transmits device measurements 44, query responses 42, script identification code, and the identification code of the operator, healthcare facility and data setting stored in the memory 80 to the server 18 through the subsequent communication link. In step 332, the microprocessor 76 receives through the modem 86 new script program 40 from the server 18. The new script program 40 is stored in the memory 80 for subsequent execution by the microprocessor 76. Following step 332, script program 40 ends.

In the above description, apparatus 26 connects to server 18 each time a new operator identification is entered.

Figure 13:
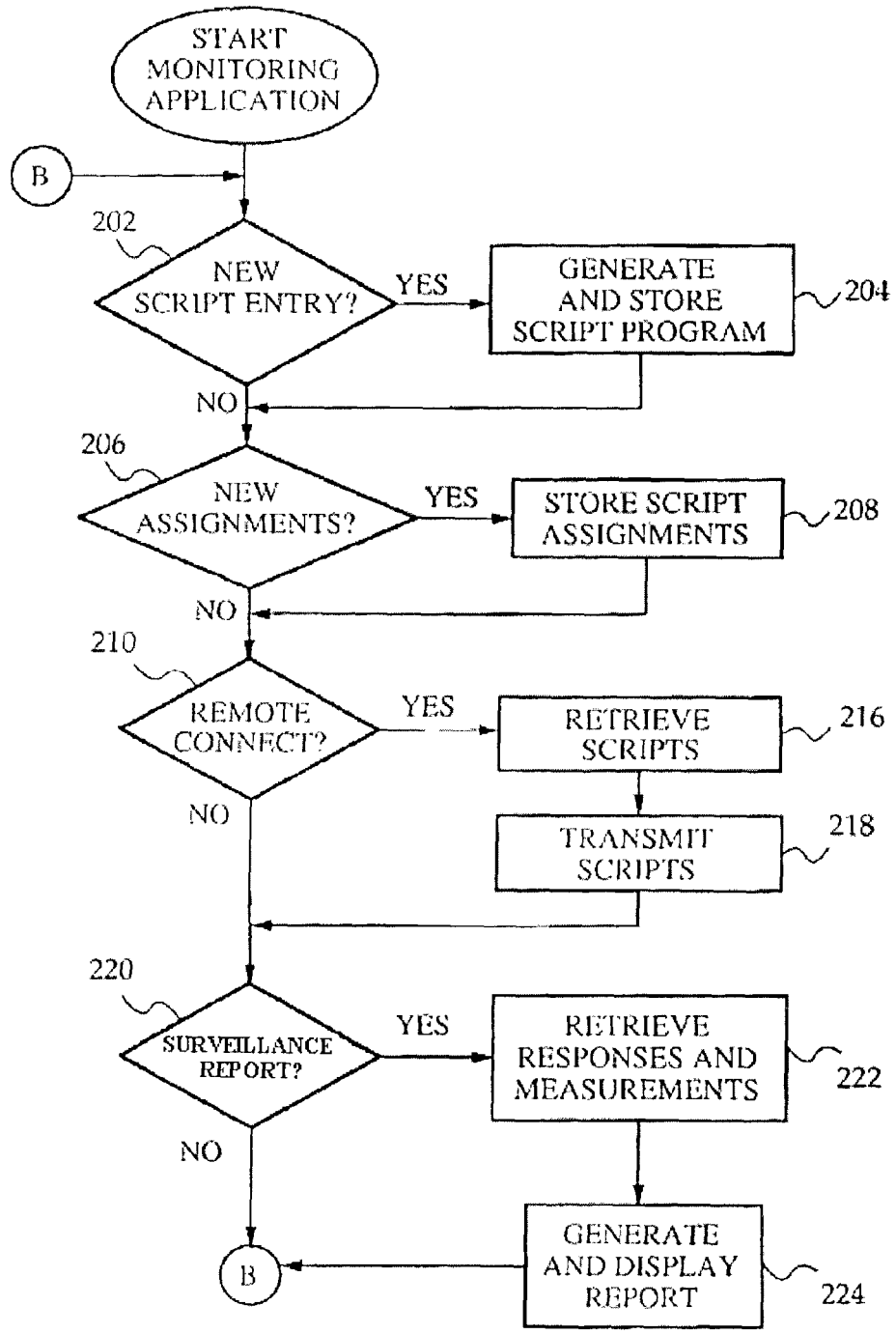
FIG. 13 flow chart illustrating the steps included in a monitoring application executed by the server of FIG. 1 according to an alternative embodiment of the invention.

FIG. 13 shows an alternative embodiment of the embodiments deposited in FIGS. 11A and 11B. The apparatus 26 connects to the server 18 at one time during the day. During this connection period, the apparatus 26 receives from the server 18 all the script programs 40 it expects to need during the following day. As shown in FIG. 13, steps 202-208 are the same as above, with the server 18 generating and storing new script assignments and new script programs if needed. In step 210, the apparatus 26 connects with the server 18. In step 216, the server 18 retrieves script programs 40 from database 38. Script programs 40 can be for operators who are likely to use apparatus 26 the following day, or script programs 40 can be for general conditions, diseases, or occurrences that are expected to take place in the future. For instance in event of a suspect or confirmed epidemic in a neighboring locality, the follow up questions would be automatically be updated into the script for those healthcare facilities serving the same and adjacent populations. In the instance where of the apparatus 26 being placed in the laboratory, the script would be that of the follow-up queries when a test is reported as positive. In step 218, the server 18 transmits the assigned script program 40 to the healthcare facility's apparatus 26 through the communication network 24. Following step 218, the server 18 proceeds to step 220, which is carried out in the same manner as the embodiment illustrated in FIGS. 11A and 11B. If a surveillance report is required, responses and measurements are retrieved per step 222. Thereafter, a display is generated and reported per step 224.

In the embodiment of FIG. 13, the operator's responses to all queries are transmitted from apparatus 26 to server 18 during a single connection period, ideally the same connection period when script programs 40 are downloaded into apparatus 26 for the following day.

Figure 14B:
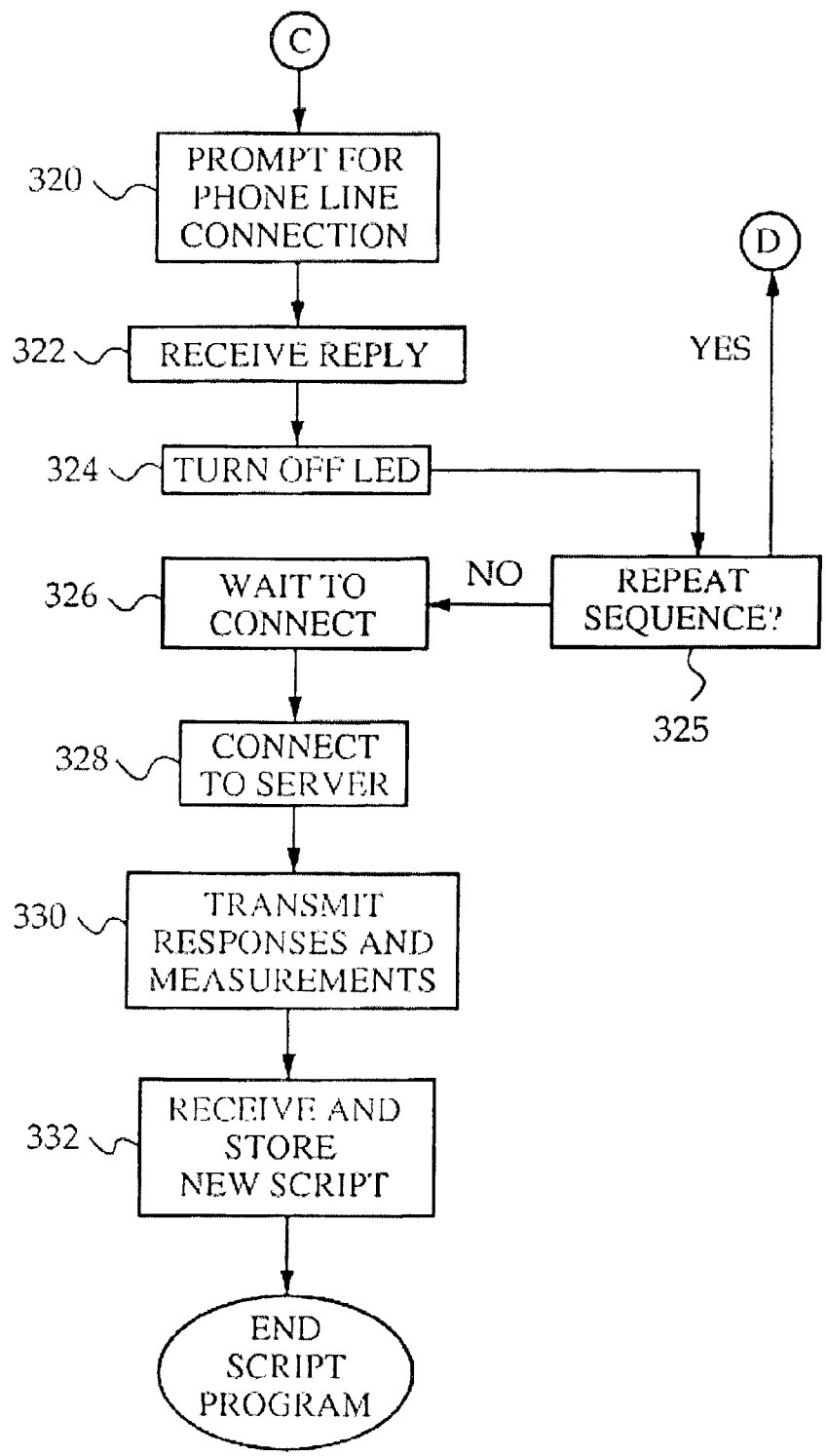
FIG. 14B is a continuation of the flow chart of FIG. 14A.

FIGS. 14A and 14B show the steps of the script program 40 for the embodiment of FIG. 13. Notice all steps are the same, except for the addition of step 325 in FIG. 14B. In step 325, the apparatus 26 has the option of repeating another script program sequence for the same or another operator before connecting to the server 18. Thus, many operators can use the apparatus 26 during the day. The apparatus 26 stores all their responses 42 and measurements 44, and then forwards them to the server 18 at the end of the day, as shown in step 330. The memory 80 in the apparatus 26 used in this embodiment must have sufficient S12E to accommodate the use of multiple operators.

The main advantage of the present invention is that it does not require that every potential data entry point have its own apparatus 26. Instead, the operators can visit the nearest station within the healthcare facility where the apparatus 26 is located and answer queries there. Since the apparatus 26 only requires identification of an operator and data source type in order to connect to the server 18 and download appropriate script programs 40, any operator can use any apparatus 18 as long as they have an operator identification code, data card, or monitoring device.

A second advantage of the monitoring system is that it allows each apparatus 26 to be programmed remotely through script programs 40. Data source survey, connection times, display prompts, selected monitoring devices, healthcare facility customization, and other operational details of each apparatus may be easily changed by transmitting a new script program 40 to the apparatus 26. Moreover, each script program 40 may be easily created and assigned by remotely accessing the server 18 through the Internet. Thus, the invention provides a powerful, convenient, and inexpensive system for remotely querying a large number of operators.

Although the embodiments focus on querying individuals working in healthcare facilities and collecting responses to the queries, the system of the invention is not limited to querying applications. The system may also be used simply to communicate messages to individuals at the above healthcare facilities. FIGS. 18-21 illustrate a third embodiment in which the system is used to perform this automated messaging function. In the third embodiment, each script program contains a set of statements to be communicated to an individual rather than a set of queries to be answered by the individual. Of course, it will be apparent to one skilled in the art that the script programs may optionally include both queries and statements.

Figure 18:
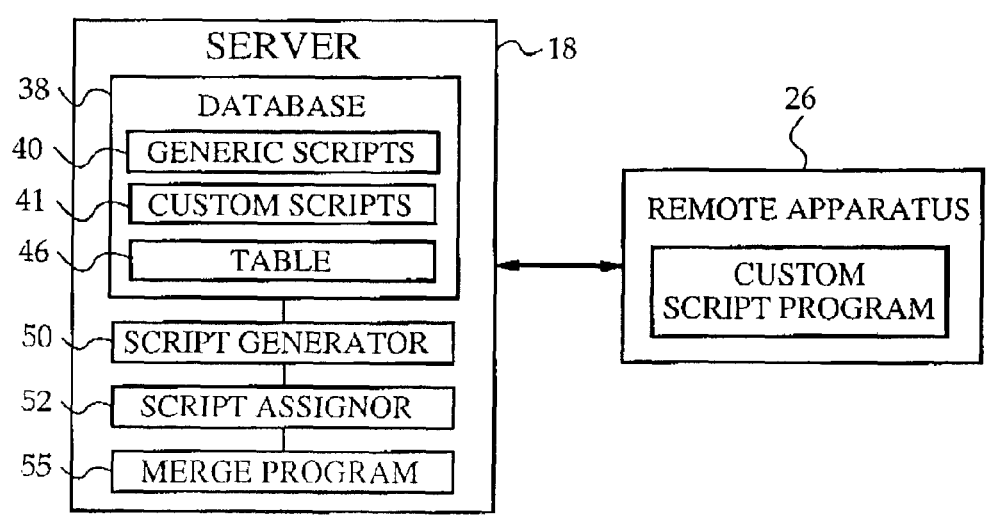
FIG. 18 is a schematic block diagram illustrating the interaction of the server of FIG. 1 with the apparatus of FIG. 3 according to a third embodiment of the invention.

The third embodiment also shows how the queries and statements may be customized to each individual by merging personal data with the script programs, much like a standard mail merge application. FIG. 18 is a schematic block diagram illustrating the components of the server 18 in communication with the apparatus 26. The server 18 includes the database 38 and the script generator program 50, the script assignor program 52, and the merge program 55. The database includes the generic scripts program 40, the custom script program 41, and the table 46. Referring to FIG. 18, personal data relating to each individual is preferably stored in the look-up table 46 of the database 38. By way of example, the data may include each operator's name, the name of the operator's healthcare facility, summarized inputted data, patient's laboratory test results, appointment dates for future consultations, or any other desired data. As in the preferred embodiment, the database 38 also stores generic script programs 40 created by the script generator 50.

The server 18 includes a data merge program 55 for merging the data stored in table 46 with generic script programs 40. The data merge program 55 is designed to retrieve selected data from the table 46 and to insert the data into statements in generic script programs 40, thus creating custom script programs 41. Each custom script program 41 contains statements, which are customized to an individual operator or healthcare facility. For example, the statements may be customized with the operator's and healthcare facility's name, etc. Examples of such customized statements are shown in FIGS. 19 and 20. In FIG. 19 response choices to the query "Note: 273 cases of acute GE presented in the last 24 hrs in your county—OK" are positioned on display 64 such that each response choice is located proximate to a respective one of input buttons 70A, 70B, 70C, and 70D. In the preferred embodiment, each response choice is displayed immediately above respective the input button 70. The operator presses input button 70A, 70B, 70C, or 70D corresponding to his or her response. The microprocessor 76 stores each response in the memory 80. Similarly, FIG. 20 response choices to the query "Jane, please ensure that all cases of acute GE answer the source trace E-questionnaire 61—OK" response choices are positioned on display 64 such that each response choice is located proximate to a respective one of input buttons 70A, 70B, 70C, and 70D. In the preferred embodiment, each response choice is displayed immediately above respective the input button 70. The operator presses input button 70A, 70B, 70C, or 70D corresponding to his or her response. The microprocessor 76 stores each response in the memory 80.

The operation of the third embodiment is similar to the operation of the preferred embodiment except that script programs 40 are used to communicate messages to the individuals rather than to query the individuals. Each message is preferably a set of statements. Referring to FIG. 21, the statements may be entered in the server 18 through the script entry screen 56, just like the queries of the preferred embodiment.

Each statement preferably includes one or more insert commands specifying data from table 46 to be inserted into the statement. The insert commands instruct the data merge program 55 to retrieve the specified data from the database 38 and to insert the data into the statement. For example, the insert commands shown in FIG. 21 instruct the data merge program to insert an individual operator's and healthcare facility's name, geographical location. As in the preferred embodiment, each statement may also include one or more response choices, which are entered in fields 96. The connection time display 100 is visible in the script entry screen 56.

Following entry of the statements and response choices, the CREATE SCRIPT button 102 is pressed. When the create script button 102 is pressed, the script generator 50 generates a generic script program from the information entered in the screen 56. The created script may be cancelled using the CANCEL button 104. The generic script program is similar to script program 40 shown in FIGS. 6A-6B, except that the display commands specify statements to be displayed rather than queries. Further, the statements include insert commands specifying data to be inserted into script program 40. As in the preferred embodiment, multiple script programs are preferably generated, e.g. a generic script program for a microbiological data source, a generic script program for emergency departments, etc. The generic script programs are stored in the database 38.

Following generation of the generic script programs, server 18 receives script assignment information entered through script assignment screen 57. As shown in FIG. 7, script programs 40 are assigned by first selecting one or more of the generic script programs through check boxes 106, selecting individuals, or groups of individuals that fulfill a given set of criteria through check boxes 108, and pressing the assign script button 112. When the assign script button 112 is pressed, the data merge program 55 creates a custom script program for each individual selected in check boxes 108.

Each custom script program is preferably created by using the selected generic script program as a template. For each individual selected, the data merge program 55 retrieves from database 38 the data specified in the insert commands. Next, data merge program 55 inserts the data into the appropriate statements in the generic script program to create a custom script program for the individual. Each custom script program is stored in database 38.

As each custom script program is generated for an individual or healthcare facility that uses the apparatus 26, the script assignor 52 assigns the custom script program to the said individual or healthcare facility. This is preferably accomplished by creating a pointer to the custom script program and storing the pointer with the individual's unique identification code in table 46. When the individual's remote apparatus connects to the server 18, the server 18 receives from the apparatus 26 the individual's unique identification code. The server 18 uses the unique identification code to retrieve from the table 46 the pointer to the custom script program assigned to the individual. Next, the server 18 retrieves the assigned custom script program from the database 38 and transmits the assigned custom script program to the apparatus 26 through the communication network 24.

The apparatus 26 receives and executes the script program 40. The execution of script program 40 is similar to the execution described in the preferred embodiment, except that statements are displayed to the individual rather than queries. FIGS. 17A, 17B, and 17C illustrate three sample statements as they appear on display 64. FIG. 17A is an Analysis Engine Report, FIG. 17B is a response from a triage facility, and FIG. 17C is a Search Engine Report. Each statement includes a response choice, preferably an acknowledgment such as "OK". After reading a statement, the individual presses the button corresponding to the response choice to proceed to the next statement. Alternatively, the script program 40 may specify a period of time that each statement is to be displayed before proceeding to the next statement. The remaining operation of the third embodiment is analogous to the operation of the preferred embodiment described above.

The multi-user capabilities of the present invention allow for the collection and tracking of healthcare facility data. Apparatuses 26 are connected to one or more servers 18. Operator responses 42 and measurements 44 are received by apparatuses 26 in the manner described above. The data is then sent to server or servers 18 where it is collected and organized. Ideally, Public Health Departments will use monitoring system 16 to gather information on the health status, and presenting complaints of patients at emergency departments, laboratory test results, and radiological reports. Analysts and surveillance experts at the Public Health Departments will send queries or script programs 40 to server 18, which will then send queries or script programs 40 to one or more apparatuses 26. After operators have answered the queries or attached their monitoring devices 28, server 18 will send the patient data back to the companies and providers.

Figure 22:
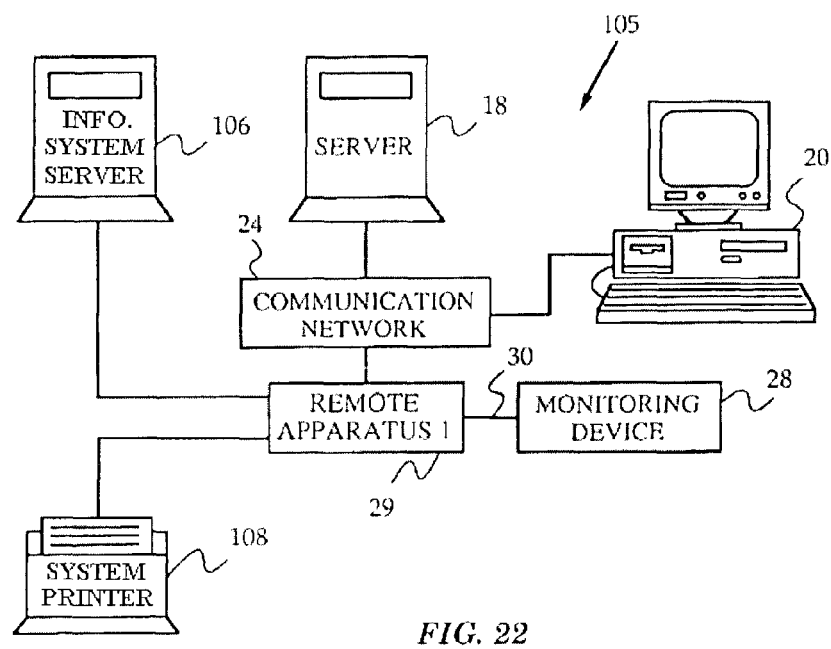
FIG. 22 is a block diagram of a networked system according to the data interception embodiment of the invention.

FIG. 22 shows how the present invention can be used in conjunction with a separate hospital information system, such as a Laboratory or a Radiological information system, the hospital reception (the hospital census), the hospital's billing and coding section or the healthcare facility's general purpose information system. Patient data from the Information System 105 can be intercepted by an apparatus 29 in order to trigger the execution of the script programs 40. In this embodiment, the apparatus 29 is located in series between an information system server 106 of an information system 105 and the information system printer 108. Information system 105 comprises system server 106, system workstation 20, and system printer 108. Patient data sent from system server 106 to system printer 108 must pass through apparatus 29. Apparatus 29 takes the patient data and sends it to server 18 of the system of the present invention. Server 18 uses patient data to determine which script program 40 to send to apparatus 29 for operator to answer. It is obvious that this method can be used to identify the data operator, input setting, and healthcare facility to apparatus 29 and also server 18. The server 18, though the communication network 24 and cable 30, communicates with the formation server 106, the system printer 108, the remote applicators 29, the monitoring device 28, and the system workstation 20.

Alternatively, interception of patient data by the apparatus 29 can be used to trigger printing of information on the system printer 108. In this embodiment, the apparatus 29 is again located in series between information system server 106 of separate information system 105 and system printer 108. When the apparatus 29 receives the patient data, it triggers a stored script program 40, which commands information system printer 108 to print out information for the patient. This information differs in content from the patient data and is printed in addition to it. In addition, the patient data can also be sent to the server 18 to trigger additional script program 40 which displays queries on the display 64 of the apparatus 29 to be answered by the patient.

Alternatively a software program that runs continuously runs in the background, gleaner program may installed on the system workstation 20 and the information system server 106.

The gleaner program will be resident on the system workstation 20 used to input information in the healthcare facility's laboratory information systems including microbiology, histopathology, biochemistry, radiology, the reception of the healthcare facility's Emergency Medical Services Department, the healthcare facility's billing section, and the system server 106 of the above information systems. The gleaner program will integrate with the healthcare facilities' existing information systems that are implemented by a multitude of software application providers without common standard format for storage, transmission, retrieval, archival, computation or implementation of data. The gleaner program is capable of (one or more of) logging all the typed keys, scanning data in the memory of system workstation 20 and information system server 106, including that on the RAM and the hard disk files and folders and storing this data in a temporary file, either in the native format or after applying Natural Language Processing methods.

The user shall have the option of setting the gleaner program to analyze the above data, either singly, or in combination of the following—continuously in real time, or at the completion of a certain period of time, when a certain number of keys have been logged, the size of the temporary file reaches a certain value, when the data entry program is closed, and when the user's terminal is shut down.

When one or more of the above conditions, as determined by the user, are fulfilled, the gleaner program uses Natural Language Processing methodology, and scans the logged temporary file for its dynamically updated registry of words/ word combinations/phrases, called watchwords, that are related to public health, for instance 'vesicular rash' or 'VII Nerve paralysis.' It will be apparent to one skilled in the art of Natural Language Processing that the registry may also include a further set of rules that will allow individualization to the particular type of laboratory or hospital information system (microbiology, histopathology, biochemistry, radiology) that is used by system workstation 20. For instance, registry at the healthcare facility's billing section shall focus on the Health Care Financing Administration's codes used for Medicare/Medicaid Reimbursement, while that at the laboratory shall focus on data that suggest information of importance in the public health surveillance context, including LOINC, HL7 and SNOMED.

On encountering the said watchwords in the temporary file, or when the language processing algorithms elicit a positive match, the gleaner program 20 will either: (1) pop up a window alerting the user to the same, and execute the relevant script program 40 in a manner such as that described for the apparatus 29, or (2) send the information to the apparatus 29 for processing, as has been detailed in the above embodiment. The apparatus 29, may also process the data in the same manner as the input via the monitoring device 28. The registry shall be updated for new data every time there is a fresh connection to the server 18. In order to circumvent the possible data-intensive nature of this method, and to optimize the size of net data transfer, the gleaner program will use process all information at system workstation 20 itself, and will only communicate only that consolidated formatted data which it has been specifically authorized to release. The gleaner program will not log, store or transfer non-demographic patient identifier data (including name, address, telephone number, etc. The gleaner program shall additionally feature the healthcare facility's identifying information and authorization codes for data upload into the system, password protection, both user and administrator in order to provide for security, operator accountability and data integrity.

Since different healthcare facilities and laboratories use software from different developers, without any present common standard format for the storage, transmission, and retrieval of data, to extract all the inputted data from existing information systems, one would need to update all the executable programs individually, often at considerable expense of time, effort and the additional possibility of inserting errors into software code, and disabling the access of older data. The earlier description of sending data from system workstation 20 to the apparatus 29 does not allow the selective transmission of relevant data to the apparatus 29. Moreover, this process is an active one, implying that there would be lesser compliance with the same system. The advantage of this invention would be that the data is scanned while it is being entered, and that only a single 'add-on' script needs to be written per operating system environment, that the program is unlikely to interfere with the functioning of the information system, as it is independent of it, and that it allows the public health surveillance system to tap into a rich source of data.

Figure 23:
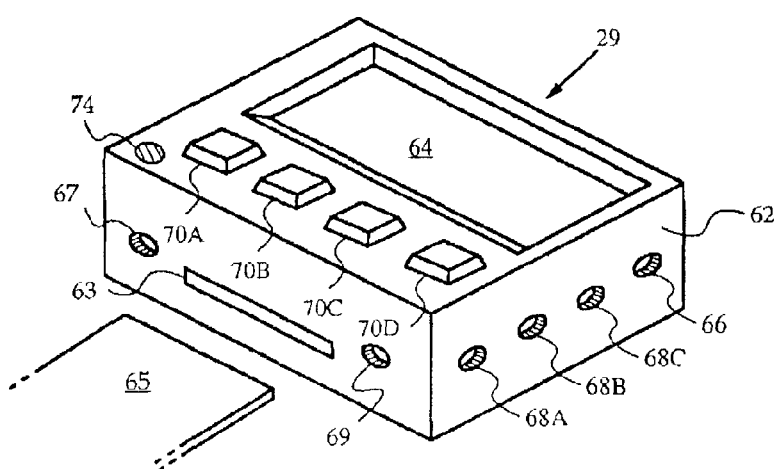
FIG. 23 is a perspective view of a remotely programmable apparatus of the system of FIG. 22.
Figure 24:
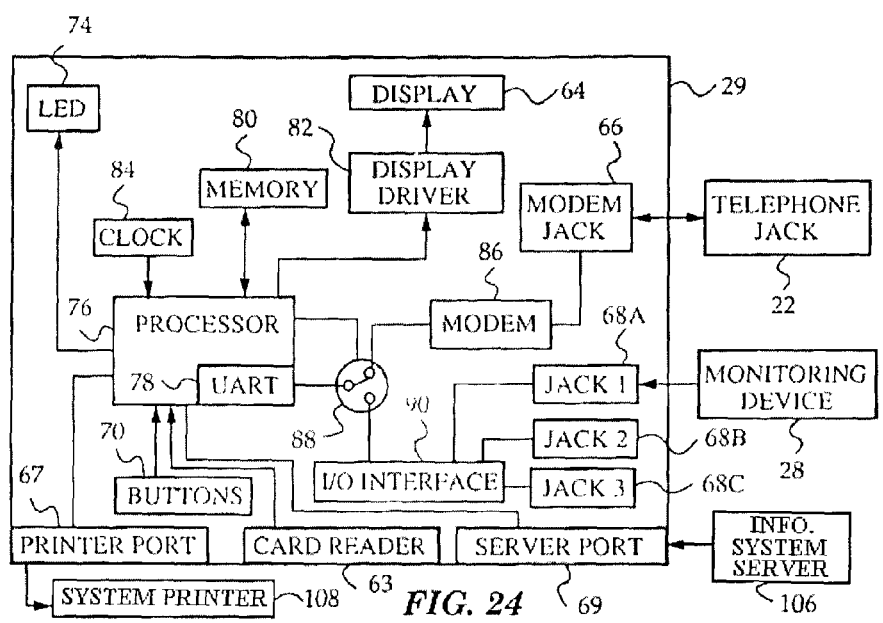
FIG. 24 is a block diagram illustrating the components of the apparatus of FIG. 23.

FIG. 23 shows a block diagram of the apparatus 29 as used in this embodiment, while FIG. 24 shows a schematic block diagram illustrating the components of the apparatus 29 in detail. FIGS. 23 and 24 are similar to FIGS. 3 and 4, except for the addition of a server port 69 in both figures. The server port 69 is used to connect the apparatus 29 to the information system server 106. The server port 69 can receive a standard SCSI cable connection or a telephone cable connection, in which case it operates as a modem. Thus the apparatus 29 can connect to the server 18 through the modem jack 66, the information system server 106 through the server port 69, the monitoring device 28 through device jacks 68A, 68B, and 68C, and system printer 108 through printer port 67.

Figure 15:
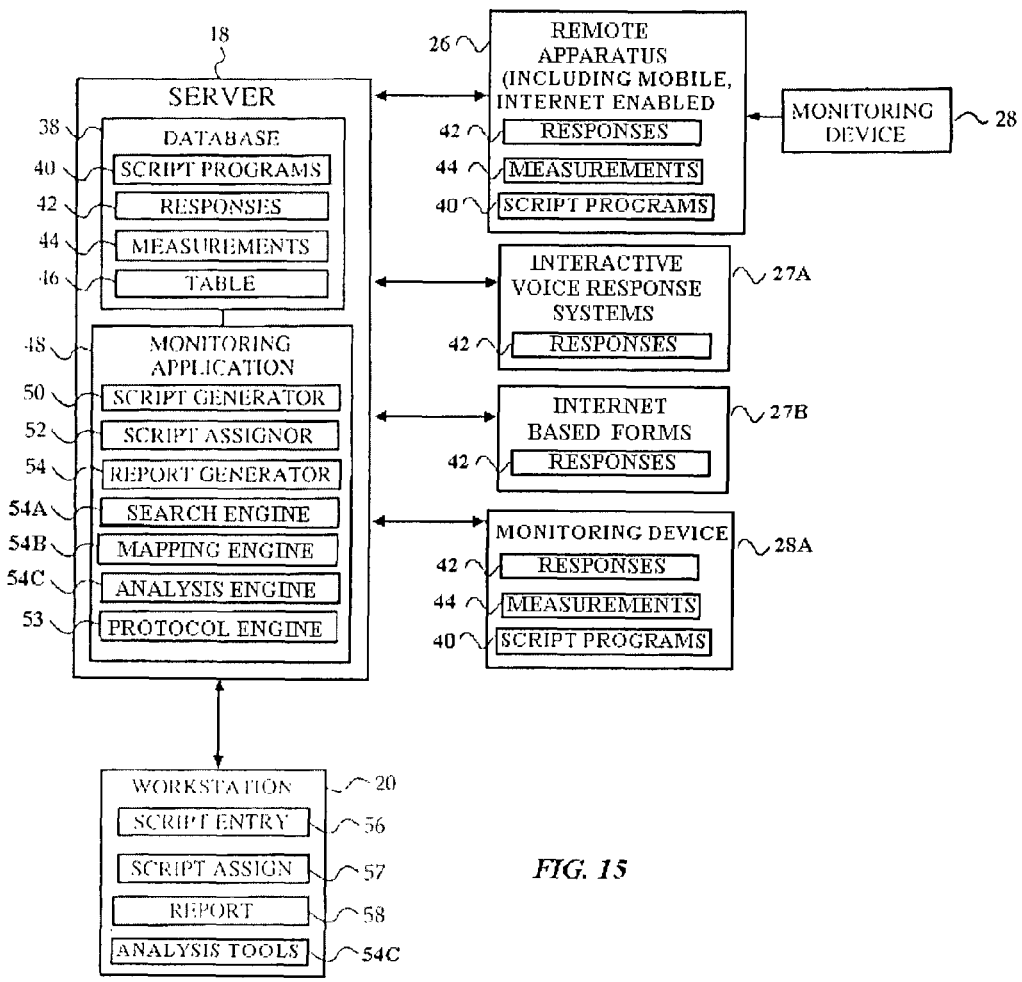
FIG. 15 is a schematic block diagram illustrating the interaction of the server of FIG. 1 with the apparatus of FIG. 3, according to an alternative embodiment of the invention. In addition, it also shows the analytical components of server 18 and includes additional potential data sources for inclusion into the system.

FIG. 15 shows a block diagram of an alternate embodiment of the invention. FIG. 15 is similar to FIG. 2 except for the depiction of additional data sources Interactive Voice Response System 27A (IVRS 27A), Internet Based Forms 27B (IBF 27B), Embedded Remote Apparatus 28A; the addition of protocol engine 53 in server 18, and the detailing of the components of report generator 54, i.e. the search engine 54A, the mapping engine 54B and an analysis engine tools 54C. In this embodiment, the report generator 54 and its components the search engine 54A, the mapping engine 54B and the analysis engine tools 54C enable the system to read the database 38, retrieve archived previous data, compare the previous numerical data with that of the present, perform statistical analyses on a daily, weekly, monthly, or yearly basis, integrate the data acquired from a plurality of healthcare facilities over distant geographical areas, compare the data with that of the previously archived data, and in addition depict this data in a pictorial format, such as a chart, a graph or a map showing the relative geographical location of occurrence of the public health event. The methodology for the data processing, analysis and report generation is described in detail in Tables 2 to 12.

Internet Based Forms 27B allow for the reporting of information by healthcare providers, primarily physicians, nurses managing patients, and other healthcare workers who are otherwise not covered by the reporting system, when they notice a rare or unusual occurrence that in their professional opinion, is highly suspicious and significantly indicative of an impending outbreak, and merits the attention of the system analyst. One such instance would be cutaneous anthrax in a young adult male whose occupation does not place him at risk for acquiring the disease, which is highly suggestive of a person who may have handled the spores. The reporting system also needs to allow for the possibility that not all healthcare providers and personnel will have immediate and ready access to the preferred reporting modality, namely the apparatus 26 and its various embodiments. In such a case, Internet Based Forms 27B with executable script programs and screens similar to that described for apparatus 26 would be used for data entry. A significant addition in Internet Based Forms 27B over the scripts described for the apparatus 26 would be that in the former, the healthcare provider would need to enter his/her identification and contact information, including the ZIP Code, or other geographical identifier information of the area from which the patient presented and preferably provide some means for verification, such as a telephone number (to call back), Social Security Number, etc. In addition, Internet Based Forms 27B would allow the healthcare provider to enter subjective information, such as a short history and findings, and justify why the case in question merits the attention of the analyst and the system. This feature is allowed since there is the real possibility that there are no scripts available for some scenarios of presentation of outbreaks. In this case, Internet Based Forms 27B would allow an alert healthcare provider to enter detailed subjective information, and bring the case to the notice of the analyst. The healthcare provider however would be encouraged to report information using the available scripts and provide responses 42 wherever possible. In addition, when there is a temporary failure of the communication system, or any of its hardware components, significant, non-routine information and responses 42 may be entered without further delay by a healthcare provider, using the same authorization codes as that used by apparatus 26 to identify the healthcare provider.

In a similar manner, the opinion of a medical examiner/coroner in cases of unexplained deaths, if thought to be relevant from the viewpoint of public health may be intimated by the concerned party to the analyst by Internet Based Forms 27B.

An algorithm would allow the automated processing of all reports based on the geographical area and the syndrome complex (chief set of complaints of the patient) and only those localities that are already highly suspicious for possible outbreaks would be brought to the immediate attention of the analyst. This can include instances, where more than one response 42 is received for a particular geographical location, or the response 42 corresponds to an area which already is 'under observation' by the analyst on the basis of responses 42 and measurements 44 received from apparatus 26 and its alternate embodiments, or if a recent detailed analysis has been performed for a similar syndrome complex in the same, or nearby area. The algorithm for performing the above functions may also be incorporated into the protocol engine 53. In all cases, however, the responses would be stored in the database 38 for future reference by the analyst by the analysis engine 54C.

The functioning and data processing capabilities of Interactive Voice Response System 27A is similar to Internet Based Forms 27B, save that the healthcare provider dials a telephone number, and enters responses 42 by pressing numeral buttons on the telephone in response to a recorded voice that plays vocalized scripts, and identification of healthcare provider and geographical location is secured by entering similar codes as that for Internet Based Forms 27B, besides the caller identification function. In addition, the healthcare provider is allowed the option of entering a voice message, which is transcribed, classified and then handled in a manner similar to the detailed subjective information report described for Internet Based forms 27B. Specific techniques for the creation and maintenance of Interactive Voice Response System 27A and Internet Based Forms 27B are well known in the art.

The protocol engine 53, a component of the server 18 serves to automate a multitude of routine functions that would otherwise have to be performed by the analyst at workstation 20. Protocol engine consists of a program that runs scripts similar to the script programs 40. The responses 42 and measurements 44 received at the server 18 is first authenticated and reliably identified by the monitoring application 48 and then transferred to the protocol engine 53. If standard operating procedures and protocols have been defined for any of the responses 42 and measurements 44, the protocol engine 53 automatically responds to the above input following the defined standard operating procedure, and makes a log of the same in the database 38. In most instances, this will be the case. On the contrary, if no standard operating procedures and protocols have been defined for the responses 42 and measurements 44 received from the apparatus 26 and its embodiments, or if this information does not fit into defined parameters, the information entered into the system would be logged directly into the database 38 and processed manually using the script generator 50, the script assignor 52, and the analytical components of the system. For example measurements 44 at the monitoring device 28 triggers a script at the apparatus 26, which calls for measurements 44 to be sent to the server 18 immediately. The protocol engine 53 at the server 18 determines that additional information is required from the clinician who ordered the test. For this, it sends another script program 40 to the clinician, and elicits responses 42 to the script program 40. Based on the clinician's responses 42, the protocol engine 53 determines that all patients henceforth presenting with a certain syndrome need to undergo an additional laboratory investigation, and answer a few extra questions. Hence, protocol engine 53 sends a new script to all triage nurses with the extra queries that all patients with a particular syndrome need to answer. It also sends a new script 40 to all clinicians in the area regarding the findings and advises them to order one or more laboratory and radiological investigations for all patients presenting with a particular group of symptoms. Simultaneously, the analyst is alerted to the situation. The analyst verifies the particulars and determines that all facilities within the locality need to be alerted regarding the particular finding, and a certain extra set of queries need to be put to all the patients, and that patients need to be isolated. The analyst also determines that a detailed analysis is due. To this end, the analyst uses analytical engine 54C, which integrates all the data inputted into the system from a particular healthcare facility into a single screen. The analyst now determines that there is a likely outbreak. The analyst now proceeds to inform the relevant statutory authorities regarding the outbreak, besides alerting all facilities, clinicians and other healthcare providers who are within the purview of the local system.

The advantage of using protocol engine would be that the server 18 responses are faster, leading to a reduced overall information turnaround times, allowing more complete, prompt and reliable analyses. In addition, the manpower requirements for system data analysis and follow-up will be reduced. In addition, there is reduced likelihood of inter-operator variability, with respect to data handling.

The data processing and analysis mechanism, as described below consists of the automated search engine 54A, and the mapping engine 54B that analyze the information received from a plurality of sources, simultaneously, and in parallel. The search engine 54A uses both inbuilt and public health analyst defined criteria and weight age factors to compute a suspicion score as detailed in Table 2 for responses 42 and measurements 44 received at server 18, and ranks these bits of information on the basis of the possibility of its being an event of public health importance.

Mapping engine 54B also uses similar criteria, and computes scores, with the difference that, in this case, the report is in the form of a spot-map showing the geographical distribution and the status of public health at the said location. The map is continuously refreshed, on the receipt of new data.

Any biological event which is found to be possibly significant by either search engine 54A, or by the analyst at the mapping engine 54B, may be followed up by the analyst by checking the relative suspicion levels on the other engine, and if found potentially significant, this event may be probed further into using the analytical engine 54C. The analytical engine 54C is a database query program, with the capability of tapping into the entire database 38 and generating reports, charts, graphs and allied pictorial representations, besides tables and summarized point data. At this juncture, the analyst may also wish to query healthcare providers and patients, and actively monitor select measurements 44 at a plurality of healthcare facilities, laboratories and information systems before forming a definite opinion. This is accomplished by the application of the script generator 50 and the script assignor 52, in the same manner as that which is described in FIG. 2. The responses 42 to such a script and its subsequent representation on the map will help the analyst in confirming or refuting a hypothesis regarding the existence, cause and nature of the biological event.

Search Engine 54A:

The search engine 54A would need to alert the analyst with such a high degree of accuracy that the analyst would not miss out any cases (zero false negatives), would not have a large number of potential biological events to analyze (which would only decrease the efficiency of the analyst, and the potential for missing out true positives) and be alerted so that the true positive event may be detected as early as reasonably possible, with a view to initiate damage control measures.

The criteria, and methods used by the search engine 54A to assign suspicion scores and to rank the individual events, are as that described in Tables 2, 3 and 4.

TABLE 2

CRITERIA USED BY SEARCH ENGINE 54A TO ASSIGN SUSPICION SCORES

| POSITIVE LOGARITHM SCORE | NEGATIVE LOGARITHM SCORING |
|---|---|
| Greater than 1 Standard Deviation (SD) increase from the mean number of cases over the past few days | Decrease in the mean number of cases |
| Significant increase in the number of cases compared to that in the previous years in terms of SD | No significant increase/ actual decrease in the number of cases compared to that in the previous years |
| Simultaneous increase in the number of cases in centers covering same and adjoining areas | Simultaneous decrease/no change in the number of cases in centers covering same area. |
| Sharp focus and limited to a (few) clearly definable geographical unit(s) | Uniform increase that is widespread, and covers geographically distant and unrelated regions |
| Confirmed case in the region in previous 2 weeks of pathogen | Cases in the region in previous 2 weeks of pathogen that clinically simulates pathogen under surveillance (false positive) |
| Attack/Indication of attack in the near past with other Weapon of Mass Destruction | No indication of any such attack. |
| Presence of newly identified risk factors specific to the particular attack. e.g. Postal workers in the recent anthrax outbreak, the Query set is updated to query for occupation, and consider it as a risk factor in further computation | Absence of the risk factors |
| Metropolitan location, high population density | Rural Areas, with low population density. |
| Constant sudden increase in the number of cases over a short interval of time. | A gradual increase that may not be explained in terms of variable incubation periods, or secondary waves |

TABLE 3

METHOD USED BY SEARCH ENGINE 54A TO ASSIGN SUSPICION SCORES FOR ATTRIBUTES OF INDIVIDUAL HEALTHCARE FACILITIES

| COMPUTED DATA | WEIGHTAGE FACTOR | WEIGHTED VALUE |
|---|---|---|
| COMPUTE NUMBER OF STANDARD DEVIATION INCREASE (=POSITIVE) OR DECREASE (=NEGATIVE) FROM THE MEAN OF PREVIOUS 2 INCUBATION PERIODS OF THE DISEASE = N1 | W1 (DEFAULT = 1) | V1 = (N1 * W1) |
| COMPUTE NUMBER OF STANDARD DEVIATION INCREASE (=POSITIVE) OR DECREASE (=NEGATIVE) FROM THE MEAN OF PREVIOUS YEARS = N2 | W2 (DEFAULT = 1) | V2 = (N2 * W2) |
| COMPUTE THE MEAN STANDARD DEVIATION INCREASE (=POSITIVE) OR DECREASE (=NEGATIVE) IN THE NUMBER OF CASES IN ADJOINING AREAS = N3 | W3 (DEFAULT = USER DEFINED) | V3 = (N3 * W3) |
| THE NUMBER OF INVOLVED HEALTHCARE FACILITIES, AND GEOGRAPHICAL UNITS = N4 | W4 (DEFAULT = USER DEFINED) | V4 = (N4 * W4) |
| CONFIRMED TRUE POSITIVE, IN RECENT PAST = (+N5) CONFIRMED FALSE POSITIVE IN RECENT PAST = (−N5) (N5 = USER DEFINED VARIABLE) | W5 (DEFAULT = 1) | V5 = (N5 * W5) |
| ATTACK/INDICATION OF ATTACK WITH WMD FOR THE PARTICULAR AREA/ REGION = (+N6) NO INDICATION OF ANY SUCH ATTACK = (−N6) (N6 = USER DEFINED VARIABLE) | W6 (DEFAULT = 1) | V6 = (N6 * W6) |
| PERCENTAGE OF QUERIED CASES POSITIVE FOR NEWLY IDENTIFIED RISK FACTOR = N7 | W7 (DEFAULT = USER DEFINED) | V7 = (N7 * W7) |
| METROPOLITAN LOCATION, HIGH POPULATION DENSITY = (+N8) RURAL AREAS, LOW POPULATION DENSITY = (−N8) (N8 = USER DEFINED VARIABLE) | W8 (DEFAULT = 1) | V8 = (N8 * W8) |
| CUSTOM VARIABLES N9, N10 ... $N_N$ | CUSTOM FACTORS W9, W10 ... $W_N$ | V9 = (N9 * W9), V10 = (N10 * W10) ... $V_N$ |

TABLE 4

METHOD USED BY SEARCH ENGINE 54A TO ASSIGN SUSPICION RANKING SCORES FOR INDIVIDUAL EVENT

IF $V_N < 0$, THEN V = (1/V).
IF $V_N = 0$, THEN V = 1
e.g. If V5 < 0 (i.e. V5 is a negative value) then the reciprocal of V5 is taken for further calculation of V
If V3 = 0 then V3 is taken as one, so that the particular $V_N$ is effectively not taken into consideration.
WEIGHTED VALUE OF PARTICULAR HEALTHCARE FACILITY, V = V1 * V2 * V3 * V4 * V5 * V6 * V7 * V8 * ... $V_N$

TABLE 4-continued

METHOD USED BY SEARCH ENGINE 54A TO ASSIGN SUSPICION RANKING SCORES FOR INDIVIDUAL EVENT

PERCENTILE VALUE OF THE PARTICULAR HEALTHCARE FACILITY, $P = V/V_{MAX}$
V of that Healthcare facility divided by the maximum V in that particular calculation set
ARRANGE THE TOP 'X' HEALTHCARE FACILITIES IN DESCENDING ORDER OF V
Where X is a user-defined number of say, the TOP 10, 20 or 50 Healthcare facilities.

In summary, the search engine 54A seeks that bit of information that is most 'suspicious' from the Public Health Surveillance point of view by assigning relative scores to each of these bits of information based on the level of suspicion, ranking these occurrences and presenting it to the analyst. The search engine 54B accomplishes this by assigning a preferably logarithmic score of suspicion (positive scores for those bits of information that increase the likelihood of an outbreak, and negative scores for the bits that fit into the 'usual') for all the inputted information into the system. The total score is the product of the individual scores for each subcategory that is evaluated. In the case where logarithmic scores are used, the total score would be the arithmetic sum of all the individual logarithmic scores.

The list created by search engine 54A would be individual to each syndrome complex being monitored but common to all the healthcare facilities being covered by a particular Analysis point, meaning that a particular health department would analyze all the data available from within that particular region, without taking into account that at the other regions, excepting the case where the data has been specifically buffered against the remaining regions.

In addition, this method allows weight age to be given to the number of information inputs from the said region that is received via the Interactive Voice Response Systems 27A and the Internet Based Forms 27B. Localization and identification of the geographical location of the data source and the region of interest may be reliably accomplished, in this case by the usage of U.S. Postal ZIP codes.

It is serially numbered, comprehensive, unambiguous unique system that is already in place. In addition, each serial number represents a manageably small geographical area, besides correlating well with the population of that area. Areas that are in geographical proximity to each other are closely numbered. In addition, it makes the input of 'historical' data simpler, and enables the development of a functional map. Through the use of Natural Language Processing algorithms, it would be possible to extract the location of residence (from the Zip codes) of all the persons affected in previous outbreaks from Electronic Patient Records. This will allow the uptake and usage of historical data into the system, and thus improve the overall accuracy and reliability of the detection process.

The search engine 54A will use the scores computed in the above manner, compute the percentile score for the biological event, and rank each event in the order of decreasing suspicion scores. Advantages of using a search engine 54A include— a. Percentile scores allow the system to alert the analyst to suspicious events that may initially be of such a small scale as to be missed on mapping engine 54B
b. Area-wise cumulative analyses may be done, and ranked, in addition to the primarily localized analyses that mapping engine 54B allows. This enables better visualization, and subsequently, earlier detection of those epidemics that occur diffusely, and are spread over long periods.
c. In allowing the analyst to focus upon a fixed number of biological events at any particular point time, a more complete and reliable analysis is enabled.

The analyst is given the additional option of excluding, or selectively including healthcare facilities/syndrome complexes of a certain geographical area within a particular search, in any combination. This will serve to prevent the duplication of data from the same area, which has the likelihood of obscuring important findings elsewhere. For instance, if there is a single large scale epidemic in a certain region A. Then, the top 50 searches might show only the healthcare facilities of A, and subsequently obscure an evolving epidemic in region B. To prevent this from occurring, the analyst would use the above option to exclude data from this area in a subsequent search. On the contrary, if a regional or a nationwide alert were declared for a particular syndrome complex, the search engine 54A would need to perform a regular focused search on the area, with a much lower threshold for the particular syndrome, in order to detect a brimming epidemic at the earliest. A regular separate search for all the remaining syndrome complexes would be pertinent, however so as to not miss a new and unrelated outbreak in the same population.

For the follow up of a particular epidemic, the mapping engine 54B is far more powerful and appropriate. When an analyst wishes to focus on a particular area, and obtain the values of suspicion for various syndrome complexes in the area, then only that area is included in the search. For instance, when there is a strong possibility of the occurrence of an epidemic in the near future in a particular area, or when the area is on follow-up of previously received suspicious data.

The data generated by analysis at the search engine 45A, the relative scores assigned by the search engine 45A to each of these occurrences, the custom variables used by the analyst and the relative scores assigned to each is archived, for the purpose of both immediate referral and comparison in the short-term as well as for audit of the entire system of analysis in the future.

The actual scores (positive and negative) and the optimal relative weight age to be given to each of the above criteria would be specific to the syndrome complex, disease causing agent, and can vary widely depending on, among other factors, the incubation period of the disease, mode of spread, communicability, virulence, percentage of a symptomatic individuals among all those infected, and the percentage of the healthcare facilities covered by the system within a particular region. This may be accurately determined, and optimized only after field trials of the system.

Mapping Engine 54B:

The mapping disease distribution in real time within any geographical region for the purpose of Public Health Surveillance has its own advantages: It comprehensively depicts available information regarding the occurrence of the disease and its distribution in two-dimensional space. The geographical inter-relationship of two or more areas and that of intervening areas is visualized in a manner that allows easy comparison and allows for further assessment of the situation if need be the case.

The criteria, definitions and methodology used by mapping engine 54B in the creation of the 'functional map' is detailed in Tables 5 through 11.

TABLE 5

ATTRIBUTES OF THE MAP

Sequential and Relative - meaning each point or location on the map may only be described with reference to at least three previously defined points, in two dimensional space. The location of the first three points, defined at the time of map creation is arbitrary, and shall remain fixed with respect to each other at all times.
Dynamic: The locations of the all the points on the map (excluding the first three) are subject to change from their respective prior locations, as and when new data is made available. It also follows that regions of the map may also be magnified, or zoomed out and viewed if considered necessary.
Individualized: Maps are individually created for each syndrome complex. In addition, special maps may also be created for depicting test results, in which case, there is a closer resemblance of the map to conventional geographical maps.
Functional Non-Linear and Non-Scalar: Equidistant regions on the map shall not necessarily be equidistant in geographical location, nor necessarily strictly represent regions of equal relative future chance of experiencing a concurrent epidemic.

TABLE 6

STEPS INVOLVED IN THE CREATION OF A RAW MAP.

Raw Map is a baseline map, individualized to each syndrome complex. It is a reference map which mapping engine 54B uses to construct the main maps. Raw map only contains the definitions of the healthcare and laboratory facilities in terms of actual pixel locations.
1. Map Parameters Defined: On arbitrary scale pixels 1 to 10000 on x-axis (west-east), and 1 to 6000 on y-axis (north-south), which may be increased by any factor, if considered necessary.
2. State Boundaries Defined: continuous lines parallel to the x-axis or y-axis dividing the entire map to approximate the geographical boundaries of the states.
3. County Boundaries Defined: within the state, continuous lines parallel to the x-axis or y-axis are drawn, dividing the entire map in the approximate manner of the natural boundaries of the counties within the states.
4. Within the state boundaries locations with a population > 1 million are first demarcated with respect to their location in the state (North/West/ . . . ) without prejudice to other locations. The same is done for locations with a population > 500,000 after this. Until this point, though the locations of the major metropolitan areas have been described, not a single healthcare facility's location has been described on the map.
5. Cluster Definition: Healthcare facilities are located in clusters in and around large metropolitan areas and the size of these areas on the map shall be proportional not to their geographic size (area) but to the population contained within. Clusters shall be demarcated to be of such area to define locations within the clusters with respect to each other in a lucid manner.
6. Hereafter, for every new Healthcare facility that is added to the purview of the system, the location of the healthcare facility within that specific cluster and relative to other facilities on the map shall be defined using a geographic map if considered necessary. The n-pixel rule: No two reporting stations, no matter how close in actual geographical location shall be placed within 'n' pixels of each other.
7. At regular intervals of time, through the use of concurrence charting of reports being inputted into the system from the respective healthcare facilities, the position of the pixel locations of the healthcare facilities on the raw map shall be dynamically updated. The method by which this is done is described in Table 12.

The initial map created in this manner will have locations with the areas representing them proportional to the size of the population, and approximate geographic location. Pixel locations will define the center point for drawing circles with radius 0 to 7 pixels (8 gradations) and darkness from clear white to jet-black with 6 intervening shades of gray.

Map Views shall be created using the Raw Map definitions for healthcare facility location.

TABLE 7

BASIC MAPPING DEFINITIONS:

Gray Scale: A method by which the quantum of disease in the region is depicted in varying (Eight) shades of gray, from clear white to completely darkly shaded circles with increasing diameters based upon increasing n values. Gray Scale may be manipulated such that the shade of Gray assigned to a particular value of n for the purpose of creating a map view can be adjusted to make it scalar, logarithmic or with unequal gradations (arbitrary), the only precondition being that the darker, and the larger the diameter of the circle, the greater the n value, the greater the potential threat.
Gray Scale value (n): a value individual to each reporting location (meaning healthcare facility), that shall be computed from the parameters described and set hence.
Buffering: Buffering is the method by which the original Gray Scale value (n) shall be so manipulated arithmetically to yield a new n, which negates a confounding factor that would otherwise have rendered the n inaccurate for the purpose of comparison. Buffering and the method for the calculation of the new n, is specific and unique to each of the variables to be buffered. Buffering may also be done in series to negate the effects of multiple confounding variables, for the purpose of computation.
Buffering Definition: defines the variable (such as seasonal variations) that will have to be buffered against, the necessity of buffering against that variable and the arithmetic manipulation that needs to be done on n in order to buffer against that variable.
Map Views: For each buffered variable and its eliminated confounding factor, a map view will be created using the n value that is buffered against that particular variable.

TABLE 8

MAP BUFFERING DEFINITIONS:

Baseline Map View: shall be that Map View created using n - the baseline n value that is a whole number, and is numerically the most recently obtained value of the number of cases per individual disease under the surveillance plan of the System by the healthcare facility. This Map View conveys little meaning, but the values of n are to be further processed for detailed analysis.
Buffering against Healthcare facility's Catchment Area (Population served by facility) x
x = n divided by average n of the previous one year
x will adjust against the larger healthcare facility's greater value of n and the smaller one's lesser value, and thus allow for uniformity of comparison of all facilities. The Map View depicting x will show the areas with greater number of cases as darker areas and fewer cases as lighter areas.
Buffering against Seasonal variations in disease patterns: s
s = x divided by the average x of all the previous years x on that day for which data is available. The Map View depicting s will be necessary to visualize for only those diseases with a known seasonal variation in the number of cases. In the initial phase (after 1 year of using the system) when only 1 or a few x values are available, then the average of the x values of the previous year's week centering on the same day may be used.
Buffering against gradual rise in incidence of disease: g
g = x divided by the average x of the previous d days,
where 'd' is a user defined variable. The Map View depicting g will buffer against the gradual rise in incidence of disease over a span of many days, which is more likely to be a natural cause or a slow rising epidemic. The number of days to buffer against will depend on the incubation period of the disease that is in question. For flu like disease (is it Anthrax) one would like to buffer for 3–6 days but for an epidemic of viral hepatitis it may even be a month or so. Unlike the rest of the map views where one would look for the dark areas to identify areas of potential disease, here one would need compare and 'digitally subtract' this map view from the one made from x values. The areas that were prominently dark with x but light or disappear with g are the ones to watch out for, and evaluate in greater detail.
Buffering against Regional and National Variations:
r = x divided by average x of the entire region (states or group of states)

TABLE 8-continued

MAP BUFFERING DEFINITIONS:

u = x divided by average x of the entire database on that day.
The map view depicting the r and u values will help reject outright the areas whose increase is a part of a gradual increase in the number of cases over the entire region and which is a natural phenomenon, and is less likely to be an epidemic.
Buffering by using image manipulation techniques: Magnification of the image will help clarify areas of doubt and help focus the attention of the analyst on the specific area with an increased number of cases.
Buffering against Clustering: A simultaneous low-grade increase in the number of cases may portend the onset of something more serious. If a small localized area (metropolitan area) shows a uniform mildly dark shade of gray then it is possible that an extreme value in another area is obscuring the real difference in the number of cases. To overcome this, the cluster in question is magnified and a new scale is applied to just this cluster. If this image now shows a central darkening or an oblong darkening with surrounding areas merging into gray, it is likely to be a focus of an epidemic.
Buffering towards Clustering: Iso-color lines shall attempt to connect areas within a region, with equal gray density and form curves on the minimum-squares principle. This will help delineate epidemics with a large focus and that are constantly moving over large regions of the territory.
Buffering against a Control: To be used only for hypothesis testing that is when there is a strong suspicion of definite epidemic activity, as a final confirmation before issuing an alert. This will require the running of a separate program through the entire x values longitudinally for the previous year and require it to compare the increase and decrease in x values with 5–10 other randomly chosen areas and to decide which two or three of these closely resembles the graph of the Test Values (namely the point of a suspected epidemic) using the two tailed t-test for significance separately on each of them. Now the test and controls are compared using the two-tailed t test separately and p values for each of the tests are calculated. A consistently low p value (<0.05) for each of the separately tested controls is very significant, and may be interpreted as an epidemic.
Image Diffusion: Image diffusion or smoothening would be to color pixels intervening between two areas of higher density; in such a manner that one area merges gradually into the other. Diffused images will cover the entire area of the map, and may be more useful when there are a multitude of Healthcare facilities in a relatively small area.

TABLE 9

MAP COMPUTATIONAL DEFINITIONS:

c, Healthcare facility Code. Pre-designated 8-digit number of the type xxxxx-xxx where the initial 5 digits correspond to the allotted ZIP codes of the area, and the last 3 digits refer to the identifier code, the serial number of the Healthcare facilities' joining the System.
$x_c$, The co-ordinate along the x-axis which in which the Healthcare facility with code c lies. The 0 co-ordinate is positioned at the top left corner of the map i.e. the Northwest.
$y_c$, The co-ordinate along the y-axis which in which the Healthcare facility with code c lies. The 0 co-ordinate is positioned at the top left corner of the map i.e. the Northwest.
$n_c$, The final number for each Healthcare facility with code c, to be used by the mapping Engine for generating the individualized Map Views.
k, Coloring variable, computed for any given Healthcare facility by numerically manipulating the range of $n_c$ in any given set of $n_c$ to reflect accurately in the obtained Map View. Value of k shall be a whole number from 1 to 8. k may also be used numerically to draw circles with radii equal to the value in pixels.

TABLE 10

INFORMATION FLOW BY SUBROUTINE AT MAPPING ENGINE 54B.

1. DO SUBROUTINE GET DATASET (will obtain relevant information from database 38, in order to compute factors)
2. COMPUTE NEXT VARIABLE

TABLE 10-continued

INFORMATION FLOW BY SUBROUTINE AT MAPPING ENGINE 54B.

3. DO SUBROUTINE GRAYSCALE
4. DRAW CIRCLE
5. IF CIRCLE DRAWN FOR ALL HEALTHCARE FACILITIES, THEN END ROUTINE, ELSE REPEAT STEP

TABLE 11

ROUTINE AND SUBROUTINE DEFINITIONS (FOR USE BY SEARCH ENGINE 54A AND MAPPING ENGINE 54B)

MAIN ROUTINE:

Default Routine, which all analyses follow.
  a.  GET dataset c, $x_c$, $y_c$.
  b.  COMPUTE $n_c$ specific to the Map View using the specific SUBROUTINE DEFINITION for the Map View to be generated.
  c.  COMPUTE $k_c$ using the SUBROUTINE GRAYSCALE (ARITH/LOG/CUSTOM-ARITH/CUSTOM-LOG/EQUID)
  d.  Draw Circle with center co-ordinates = ($x_c$, $y_c$), radius = $k_c$ shading = Hex
SUBROUTINE CATCHMENT:

Calculation of $n_c$ specific to the Map View obtained after buffering against Healthcare facility's Catchment Area, x
  a.  GET dataset n.
  b.  avg = (sum of all n of a particular c for the last one year)/total number of added variables
  c.  FOR EACH c, COMPUTE $n_c$ = n/avg
  d.  END SUBROUTINE
SUBROUTINE SEASONAL:

Calculation of $n_c$ specific to the Map View obtained after buffering against Seasonal variations in disease patterns, s
  a.  GET dataset n.
  b.  s = (sum of all available n of a particular c for the past few years)/total number of added variables
  c.  FOR EACH c, COMPUTE $n_c$ = n/s
  d.  END SUBROUTINE
SUBROUTINE GRADUAL:

Calculation of $n_c$ specific to the Map View obtained after buffering against gradual rise in incidence of disease, g
  a.  GET dataset n.
  b.  g = (sum of all available n of a particular c for the past 14 days)/total number of added variables
  c.  FOR EACH c, COMPUTE $n_c$ = n/g
  d.  END SUBROUTINE
SUBROUTINE REGIONAL:

Calculation of $n_c$ specific to the Map View obtained after buffering against Regional and National Variations:
  a.  GET dataset n.
  b.  r = (sum of all available n of the entire region to be buffered against - county or group of counties or state or entire country)/total number of added variables
  c.  FOR EACH c, COMPUTE $n_c$ = n/r
  d.  END SUBROUTINE
SUBROUTINE MAGNIFY:

Magnification of the image will help clarify areas of doubt and help focus the attention of the analyst on the specific area with an increased number of cases.
SUBROUTINE ANTICLUSTER:

a.  GET dataset n.
  b.  GET User Definition for cluster.
  c.  FOR EACH c = User Definition, THEN COMPUTE $n_c$ ELSE GOTO NEXT c
  d.  END SUBROUTINE
SUBROUTINE PROCLUSTER:

a.  GET dataset n.
  b.  GET User Definition for cluster.

TABLE 11-continued

ROUTINE AND SUBROUTINE DEFINITIONS
(FOR USE BY SEARCH ENGINE 54A AND MAPPING ENGINE 54B)

c. FOR EACH c = User Definition, THEN COMPUTE $n_c$ ELSE GOTO NEXT c
d. DRAW LINE CONNECTING ($x_c$, $y_c$) of c with equal k
e. END SUBROUTINE
SUBROUTINE IMAGE_RENDER:

a. GET Image Map View
b. RENDER IMAGE
c. END SUBROUTINE
SUBROUTINE CUSTOM:

a. GET dataset n.
b. GET USER_CUSTOM_DEFINITION
c. FOR EACH c, COMPUTE $n_c$ using USER_CUSTOM_DEFINITION
d. END SUBROUTINE
SUBROUTINE GRAYSCALE ARITHMETIC:

Arithmetic scale is the default grayscale subroutine.
a. GET dataset $n_c$
b. Find maximum value of $n_c$ = max
c. COMPUTE $k_c = n_c$/max
d. IF $k_c <$ or = 0.125 THEN k = 1, Color Hex = {FF, FF, FF}, END SUBROUTINE; ELSE GOTO NEXT STEP
e. IF 0.125 < $k_c <$ or = 0.250 THEN k = 2, Color Hex = {CC, CC, CC}, END SUBROUTINE; ELSE GOTO NEXT STEP
f. IF 0.250 < $k_c <$ or = 0.375 THEN k = 3, Color Hex = {C0, C0, C0}, END SUBROUTINE; ELSE GOTO NEXT STEP
g. IF 0.375 < $k_c <$ or = 0.500 THEN k = 4, Color Hex = {99, 99, 99}, END SUBROUTINE; ELSE GOTO NEXT STEP
h. IF 0.500 < $k_c <$ or = 0.625 THEN k = 5, Color Hex = {80, 80, 80}, END SUBROUTINE; ELSE GOTO NEXT STEP
i. IF 0.625 < $k_c <$ or = 0.750 THEN k = 6, Color Hex = {66, 66, 66}, END SUBROUTINE; ELSE GOTO NEXT STEP
j. IF 0.750 < $k_c <$ or = 0.875 THEN k = 7, Color Hex = {33, 33, 33}, END SUBROUTINE; ELSE GOTO NEXT STEP
k. k = 8, Color Hex = {00, 00, 00}, END SUBROUTINE
SUBROUTINE GRAYSCALE LOGARITHMIC:

Logarithmic Scale
a. GET dataset $n_c$
b. Find maximum value of $n_c$ = max
c. COMPUTE $k_c = \log_{max}(n_c)$ [logarithm of ($n_c$) to the base (max)]
d. IF $k_c <$ or = 0.125 THEN k = 1, Color Hex = {FF, FF, FF}, END SUBROUTINE; ELSE GOTO NEXT STEP
e. IF 0.125 < $k_c <$ or = 0.250 THEN k = 2, Color Hex = {CC, CC, CC}, END SUBROUTINE; ELSE GOTO NEXT STEP
f. IF 0.250 < $k_c <$ or = 0.375 THEN k = 3, Color Hex = {C0, C0, C0}, END SUBROUTINE; ELSE GOTO NEXT STEP
g. IF 0.375 < $k_c <$ or = 0.500 THEN k = 4, Color Hex = {99, 99, 99}, END SUBROUTINE; ELSE GOTO NEXT STEP
h. IF 0.500 < $k_c <$ or = 0.625 THEN k = 5, Color Hex = {80, 80, 80}, END SUBROUTINE; ELSE GOTO NEXT STEP
i. IF 0.625 < $k_c <$ or = 0.750 THEN k = 6, Color Hex = {66, 66, 66}, END SUBROUTINE; ELSE GOTO NEXT STEP
j. IF 0.750 < $k_c <$ or = 0.875 THEN k = 7, Color Hex = {33, 33, 33}, END SUBROUTINE; ELSE GOTO NEXT STEP
k. k = 8, Color Hex = {00, 00, 00}, END SUBROUTINE
SUBROUTINE GRAYSCALE CUSTOM-ARITHMETIC:

Arithmetic Scale with user defined gradation.
a. GET dataset $n_c$
b. GET User specified variables var1, var2, var3, var4, var5, var6, var7 such that 0 < var1 < var2 < var3 < var4 < var5 < var6 < var7 < 1
c. Find maximum value of $n_c$ = max
d. COMPUTE $k_c = n_c$/max
e. IF $k_c <$ or = var1 THEN k = 1, Color Hex = {FF, FF, FF}, END SUBROUTINE; ELSE GOTO NEXT STEP
f. IF var1 < $k_c <$ or = var2 THEN k = 2, Color Hex = {CC, CC, CC}, END SUBROUTINE; ELSE GOTO NEXT STEP
g. IF var2 < $k_c <$ or = var3 THEN k = 3, Color Hex = {C0, C0, C0}, END SUBROUTINE; ELSE GOTO NEXT STEP
h. IF var3 < $k_c <$ or = var4 THEN k = 4, Color Hex = {99, 99, 99}, END SUBROUTINE; ELSE GOTO NEXT STEP
i. IF var4 < $k_c <$ or = var5 THEN k = 5, Color Hex = {80, 80, 80}, END SUBROUTINE; ELSE GOTO NEXT STEP
j. IF var5 < $k_c <$ or = var6 THEN k = 6, Color Hex = {66, 66, 66}, END SUBROUTINE; ELSE GOTO NEXT STEP
k. IF var6 < $k_c <$ or = var7 THEN k = 7, Color Hex = {33, 33, 33}, END SUBROUTINE; ELSE GOTO NEXT STEP
l. k = 8, Color Hex = {00, 00, 00}, END SUBROUTINE
SUBROUTINE GRAYSCALE CUSTOM-LOGARITHMIC:

Logarithmic Scale with user defined gradation.
a. GET dataset $n_c$
b. Find maximum value of $n_c$ = max
c. COMPUTE $k_c = \log_{max}(n_c)$ [logarithm of ($n_c$) to the base (max)]
d. GET User specified variables var1, var2, var3, var4, var5, var6, var7 such that 0 < var1 < var2 < var3 < var4 < var5 < var6 < var7 < 1
e. IF $k_c <$ or = var1 THEN k = 1, Color Hex = {FF, FF, FF}, END SUBROUTINE; ELSE GOTO NEXT STEP
f. IF var1 < $k_c <$ or = var2 THEN k = 2, Color Hex = {CC, CC, CC}, END SUBROUTINE; ELSE GOTO NEXT STEP
g. IF var2 < $k_c <$ or = var3 THEN k = 3, Color Hex = {C0, C0, C0}, END SUBROUTINE; ELSE GOTO NEXT STEP
h. IF var3 < $k_c <$ or = var4 THEN k = 4, Color Hex = {99, 99, 99}, END SUBROUTINE; ELSE GOTO NEXT STEP
i. IF var4 < $k_c <$ or = var5 THEN k = 5, Color Hex = {80, 80, 80}, END SUBROUTINE; ELSE GOTO NEXT STEP
j. IF var5 < $k_c <$ or = var6 THEN k = 6, Color Hex = {66, 66, 66}, END SUBROUTINE; ELSE GOTO NEXT STEP
k. IF var6 < $k_c <$ or = var7 THEN k = 7, Color Hex = {33, 33, 33}, END SUBROUTINE; ELSE GOTO NEXT STEP
l. k = 8, Color Hex = {00, 00, 00}, END SUBROUTINE
SUBROUTINE GRAYSCALE EQUIDISTANT:

Equidistant Scale will have an equal number of Healthcare facilities in each gradation.
a. GET dataset $n_c$
b. Arrange dataset in increasing order
c. Total number of variables in dataset = v
d. $e_c$ = 1 for the variable with lowest $n_c$, e = e + 1 for increasing $n_c$ till e = v
e. COMPUTE $k_c = r_c$/v
f. IF $k_c <$ or = 0.125 THEN k = 1, Color Hex = {FF, FF, FF}, END SUBROUTINE; ELSE GOTO NEXT STEP
g. IF 0.125 < $k_c <$ or = 0.250 THEN k = 2, Color Hex = {CC, CC, CC}, END SUBROUTINE; ELSE GOTO NEXT STEP
h. IF 0.250 < $k_c <$ or = 0.375 THEN k = 3, Color Hex {C0, C0, C0}, END SUBROUTINE; ELSE GOTO NEXT STEP
i. IF 0.375 < $k_c <$ or = 0.500 THEN k = 4, Color Hex = {99, 99, 99}, END SUBROUTINE; ELSE GOTO NEXT STEP
j. IF 0.500 < $k_c <$ or = 0.625 THEN k = 5, Color Hex = {80, 80, 80}, END SUBROUTINE; ELSE GOTO NEXT STEP
k. IF 0.625 < $k_c <$ or = 0.750 THEN k = 6, Color Hex = {66, 66, 66}, END SUBROUTINE; ELSE GOTO NEXT STEP
l. IF 0.750 < $k_c <$ or = 0.875 THEN k = 7, Color Hex = {33, 33, 33}, END SUBROUTINE; ELSE GOTO NEXT STEP
m. k = 8, Color Hex = {00, 00, 00}, END SUBROUTINE Besides this, the map is linked to database 38 that stores information of the healthcare facilities, and of the local area region, so that additional functions may be created linking the incidence of cases with the population of the area, previous data on the number of cases, incidence of disease in the area, etc For instance, the analyst may want to find the change in the rate of incidence of the disease with respect to the previous years, which will require that the population data for the said years be available.

The mapping Engine 54B allows the accurate depiction of isolated events that cannot be adequately visualized in the search engine 54A. For instance, a few isolated cases of an extremely rare syndrome complex may be missed entirely on the search engine 54A, while the gray scaling attributes of the mapping engine 54B and essentially lousy depiction of data can reduce the sensitivity of detection. For this reason, a combination of the two approaches is proposed, with one complementing the other, in order to increase the sensitivity of the system.

Current Mapping systems in the realm of Public Health Surveillance depict disease distribution geographically without making allowance for the pattern of actual distribution of humans within the same geographical region, or other factors that do have an important bearing on the numbers and location of presentation of cases, and sub-distribution within the region of the physically unwell. For instance, these mapping systems would only show the physical location of the region of incidence of disease in space, without taking into account 1. The effects of inter-migration of the population within the region, and from one region to another
2. The number of people living within the same region,
3. The age, gender and other pertinent demographic characteristics relevant to a particular disease, within the same
4. The healthcare delivery systems available within the region, and the facility that the member of a sub-group is most likely to present to with his/her health condition, acute, sub-acute or chronic.
5. Other factors (natural) that may simultaneously have a bearing on the incidence of disease in two physically disparate populations, such as a common water source, a common vector that causes the spread of disease, etc.

Since, the incidence, and the actual pattern of occurrence of human disease in any geographical entity, such as a country, or even an entire continent parallels not only the distribution of humans within that area, but also the abovementioned factors, a mapping system based purely on the former may not serve its purpose optimally. Regions that are far separated geographically may, in fact be closely related 'functionally', meaning the true manner of disease spread.

TABLE 12

SHOWS THE METHODS INVOLVED IN THE CREATION OF A FUNCTIONAL RAW MAP

ACQUIRE RAW MAP PIXEL LOCATIONS FOR ALL HEALTHCARE FACILITIES/REPORTING LOCATIONS ON THE MAP.
TAKE ATLEAST 3 REFERENCE POINTS 1, 2 AND 3 ON THE MAP. WHERE POINTS 1, 2 AND 3 ARE USER DEFINED ARBITRARY LOCATIONS ON THE MAP FOR EXAMPLE: LOCATION IDENTIFIERS FOR REFERENCE POINT 1 = (X1, Y1), POINT 2 = (X2, Y2) AND SO ON.
ACQUIRE DATABASE 38 RECORDS FOR ALL SIMILAR BIOLOGICAL EVENT TYPES REPORTED BY HEALTHCARE FACILITIES/REPORTING LOCATIONS IN A GIVEN PERIOD OF TIME.
LET P(Z) = NUMBER OF TIMES THE SAME EVENT HAS OCCURRED AT ANY POINT Z
E.G. P(1) = NUMBER OF TIMES THE EVENT HAS OCCURRED AT REFERENCE POINT 1. P(7) = NUMBER OF TIMES THE EVENT HAS OCCURRED AT FACILITY 7
LET Q(Z1, Z2) = NUMBER OF TIMES THE EVENT HAS OCCURRED WITHIN AN INTERVAL OF TIME AT BOTH FACILITY Z1 AND Z2.
E.G. Q(2, 25) = NUMBER OF TIMES THE EVENT HAS OCCURRED WITHIN AN INTERVAL OF TIME AT BOTH REFERENCE POINT 2 AND FACILITY 25.
* 'INTERVAL OF TIME' AS DEFINED ABOVE MAY VARY WIDELY DEPENDING ON THE INCUBATION PERIODS, AND OTHER CHARACTERISTICS OF THE DISEASES UNDER SURVEILLANCE. IT MAY AS LOW AS 2 HOURS IN SOME SYNDROME GROUPS (SUCH AS VIRAL HEMORRHAGIC FEVERS), AND AS LONG AS EVEN A WEEK OR MONTH IN CASE OF OTHER SYNDROME GROUPS (E.G. SYNDROME GROUPS OF BRUCELLA-LIKE ILLNESS)
SIMILARLY, LET Q(Z1, Z2, Z3 . . . ZN) = NUMBER OF TIMES THE EVENT HAS OCCURRED WITHIN AN INTERVAL OF TIME AT BOTH REFERENCE POINT 2 AND FACILITY 25.
CONCURRENCE SCORE, C(Z1, Z2),
READ AS CONCURRENCE OF Z2 WITH REFERENCE TO Z1
THE PROBABILITY OF THE BIOLOGICAL EVENT'S OCCURRING IN Z2 WITHIN THE SAME 'INTERVAL OF TIME', ONCE IT HAS BEEN REPORTED AT Z1 IS COMPUTED BY THE FORMULA,
C(Z1, Z2) = [Q(Z1, Z2)]/[P(Z2)]

TABLE 12-continued

SHOWS THE METHODS INVOLVED IN THE CREATION OF A FUNCTIONAL RAW MAP

METHOD TO COMPUTE THE NEW MAPPING CO-ORDINATES BETWEEN TWO NON-STANDARD POINTS Z1 AND Z2, GIVEN OLD MAP CO-ORDINATES OF POINT Z1 = (oldXZ1, oldYZ1), AND THAT OF POINT 2 = (oldXZ2, oldYZ2), WHERE ALL ABOVE VARIABLES oldXZ1, oldYZ1, oldXZ2, oldYZ2 ARE WHOLE NUMBERS:
[newXZ2 − newXZ1] = [oldXZ2 − oldXZ1] * [1 − {C(Z1, Z2)}]
[newYZ2 − newYZ1] = [oldYZ2 − oldYZ1] * [1 − {C(Z1, Z2)}]
IF POINT 1 IS USED AS A STANDARD REFERENCE POINT AS DESCRIBED IN TABLE 6, AND NEW CO-ORDINATES ARE TO BE CALCULATED FOR POINT Z2, THE ABOVE FORMULA IS EXPRESSED AS:
newXZ2 = oldX1 + [oldXZ2 − oldX1] * (1 − {C(1, Z2)}]
newYZ2 = oldY1 + [oldYZ2 − oldY1] * (1 − {C(1, Z2)}]
IF NEITHER POINT Z1 NOR POINT Z2 IS A STANDARD REFERENCE POINT, BUT NEW CO-ORDINATES ARE TO BE COMPUTED FOR SPECIFIC POINT 2 WITH RESPECT TO POINT 1, newXZ1 AND newYZ1 IS FIRST COMPUTED USING STANDARD REFERENCE POINT r, WITH STANDARD CO-ORDINATES (Xr, Yr)
newXZ1 = oldXZ1 + [oldXZ1 − Xr] * [1 − {C(1, r)}]
newYZ1 = oldYZ1 + [oldYZ1 − Yr] * [1 − {C(1, r)}]
AND THEN THE FOLLOWING FORMULA IS APPLIED-
newXZ2 = newXZ1 + [oldXZ2 − oldXZ1] * [1 − {C(1, 2)}]
newYZ2 = newYZ1 + [oldYZ2 − oldYZ1] * [1 − {C(1, 2)}]
EACH TIME THE ABOVE FORMULA IS APPLIED TO COMPUTE FIGURES, THE TOTAL SIZE OF THE MAP AND THE DISTANCE BETWEEN ANY TWO POINTS CAN ONLY DECREASE, ALTHOUGH DIFFERENTLY FOR DIFFERENT SETS OF POINTS, SINCE newX AND newY EQUALS oldX AND oldY MULTIPLIED BY A NUMBER THAT IS LESS THAN ONE.
THIS CAN CAUSE CROWDING AND THE LOSS OF DETAIL WHEN APPLIED REPEATEDLY. TO PREVENT THIS, CORRECTION WILL NEED TO BE APPLIED TO 'SPREAD OUT' THE COMPLETE MAP TO COVER THE WHOLE ORIGINAL MAP SIZE. THIS CORRECTION FACTOR WILL BE EQUALLY APPLIED TO ALL POINTS ON THE MAP, AND IS AN ARBITRARY NUMBER CHOSEN BETWEEN 1 AND 3.
X = newX * CORRECTION FACTOR
Y = newY * CORRECTION FACTOR
COMPUTATION AND ASSIGNING VARIABLES USING MULTIPLE REFERENCE POINTS: USING MULTIPLE REPRESENTATIVE POINTS FOR REFERENCE, WHILE INCREASING THE COMPLEXITY OF THE RAW MAP CREATION SYSTEM, AND THE COMPUTATIONS REQUIRED TO OBTAIN THE FINAL RAW MAP CO-ORDINATES, WILL GREATLY ENHANCE THE ACCURACY OF THE MAP.
IN THIS CASE, SEPARATE COMPUTATIONS ARE MADE FOR THE TWO OR MORE REFERENCE POINTS, AND MULTIPLE VALUES OF X AND Y CO-ORDINATES ARE OBTAINED FOR EACH POINT, CORRESPONDING TO EACH OF THE TWO OR MORE REFERENCE POINTS IN THE SYSTEM, AND THE FINAL X AND Y CO-ORDINATES FOR USE SHALL BE COMPUTED USING THE 'MINIMUM SQUARES METHOD'.
IN THIS MANNER, THE FUNCTIONAL RAW MAP IS CREATED FOR EACH SYNDROME GROUP.
IN ADDITION TO HEALTHCARE AND LABORATORY POINTS, MAPS SIMILAR TO THAT DESCRIBED ABOVE MAY ALSO BE CREATED FOR GROUPS OF HEALTHCARE AND LABORATORY FACILITIES, BY REGION, SUCH AS PARTS OF OR COMPLETE COUNTIES, GROUPS OF COUNTIES AND STATES, AFTER SUMMARIZING THE ABOVE DATA.

In addition to the above, correlation coefficients may be used in select cases to search for missing cases, after one facility has reported illness, and in creating priority lists in sentinel surveillance in case where there is the likelihood that large numbers of people are exposed to disease causing agents. Areas with a high correlation coefficient are followed up first followed by areas and healthcare facilities that have lower correlation coefficients to the reference points.

Table 12 describes the approach and methodology for the creation of a functional map, and a means to allow for constant automated update, thus creating a model that closely resembles the real life scenario and the manner of presentation of disease in the community, based on past data. It is obvious that functional maps for different syndromes may vary markedly in their appearances, and are NOT interchangeable.

In the instance when there is a focal outbreak of disease, a functional raw map, such as the one detailed above may be created using the region of outbreak of disease as a reference point. This will depict the functional relationship of the health status of the sub-communities within a region in a more accurate manner, and enable more reliable and earlier detection times. In the instance where no outbreak of disease has occurred, it may be more appropriate to use the standard reference points to create the raw functional map, for this involves the least amount of computational power. If there is sufficient indication that more accurate depictions are needed, this may be replaced by another functional raw map. In the instance where there is a diffuse widespread increase in the number of cases, it would be more appropriate to include multiple reference points, with averaging done of the values, using the minimum squares method, as is well known to those well versed in the art. It may be further noted that, the various routines and subroutines and mapping definitions described in Tables 8 to 11 shall be applied on the raw map as described in functional raw map as described in Table 6 and functional raw map on Table 12.

Analytical Engine 54C:

The analytical engine 54C is a program with the capability to tap into the entire database 38, including the archived data quickly, efficiently, reliably, and in real time, produce numerical datasets dynamically in response to parameters entered by the analyst, and create graphical representations of the said datasets on command. The database 38 is organized in a manner that will facilitate analysis of two or more datasets (including the number of reported cases) on a longitudinal, cross-sectional, or a combination of both approaches, of one or more regions, in part, or in whole. Functions analogous to that described for the search engine 54A the and mapping engine 54B would be built into the System for ease of comparison of two or more datasets, and for the computation of statistical functions, including mean, standard deviation, variance, etc. In addition, the analytical engine 54C will feature macros that allow the Analyst to create, and store custom-formulae for the comparison of two or more datasets and obtain graphical representations of these datasets, including graphs, charts, and line diagrams.

Sample analyses that may be performed at the level of analytical engine 54C include—
1. Daily number of reported cases in the region over the period comprising two mean incubation periods of the disease
2. Daily number of reported cases compared with that of the previous years number of cases on the same days of the year (to adjust for seasonal variation in the number of cases).
3. Increase in the number of cases in the other healthcare facilities serving the region, expressed as a percentage, vis-à-vis the healthcare facility in question
4. Increase in the number of cases in the healthcare facilities serving adjoining regions, expressed as a percentage
5. Increase in the number of cases in the region compared with the increase in the number of cases in the regions showing a high rate of correlation with respect to disease occurrence.
6. Comparison of the number of reported cases with 'projected' numbers derived from mathematical models based on disease characteristics.

The analytical engine 54C shall be used when the figures and automated reports 58 generated by the search engine 54A and the mapping engine 54B are ambiguous, contradictory, inexplicable in view of available data, inconclusive or simply indicate that a detailed analysis is merited. The specialized database query, and report generation capabilities of the analytical engine 54C enable a more thorough and detailed examination of all available data. In addition, responses 42 and measurements 44 in response to a dynamically generated script may be directly uploaded from the database 38 into the analytical engine 54C and depicted using the same functions, so as to provide an early indication to the public health analyst of the occurrence of the outbreak.

The analytical engine 54C has the additional capability of allowing the analyst to integrate and view all the responses 42 and measurements 44 received from a healthcare facility at the same time, and correlate the laboratory data with the healthcare provider's and patient's responses and form an opinion regarding the relative significance of each bit of information, and to differentiate the trivial and the incidental from the significant in the context of public health surveillance.

The advantage of the analytical engine 54C, is that the reports allow an overview of multiple interrelated sources of data at a single sitting. The multiple interrelated sources of data that are chosen for representation may be that which is built into the system, but it would also be possible for the operator to customize the final report including only those components within it that are most significant.

FIG. 17A is a sample analytical engine report created from the components of the embodiment in FIG. 15.

FIG. 17B is a continuation of FIG. 17A.

FIG. 17C is a continuation of FIG. 17B.

Figure 16A:
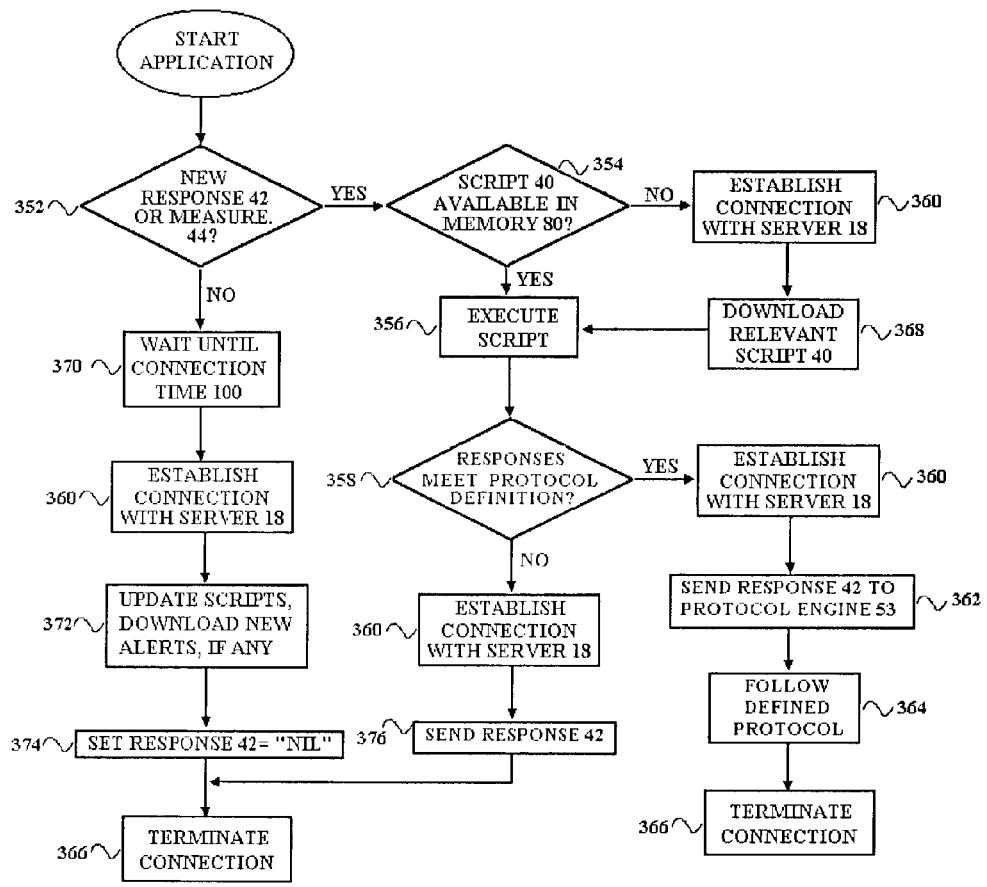
FIG. 16A is a flow chart illustrating the steps included in a monitoring application to enable automated script assignation, according to an alternative embodiment of the invention.

FIG. 16A is a flowchart showing the steps involved in data handling at the level of the apparatus 26, the monitoring device 28 and the monitoring device 28A. In step 352, the script program running on the apparatus 26 is activated by new responses 42 and/or measurements 44. In step 354, the monitoring application checks to see if the corresponding script program 40 is available in the memory 80. If the script program 40 is available in memory 80, it begins to execute the script directly (step 356). If, on the contrary, the script program 40 is not available, the apparatus 26 performs step 360 (establishes connection with the server 18 via the communication network 24) followed by step 368 (downloads the script program 40 after sending data to the monitoring application 53 at the server 18). Following this, the apparatus 26 or 28A starts executing the script program 40 (step 356) At this point of time, the monitoring application checks to see if the responses of the healthcare provider meet available protocol definitions (step 358). If this were the case, it again performs step 360 (establishing connection to the server 18) sends responses 42 to the protocol engine 53 (step 362) and follows the defined protocol/standard operating procedure (step 364) and terminates the connection (step 366). On the contrary, if at step 358, responses 42 and measurements 44 have no corresponding associated protocols/standard operating procedures, step 360 (establish connection with server 18) is followed by step 376 (responses are sent to be stored in database 38) followed by termination of the connection.

In case no responses 42 or measurements 44 are received by apparatus 26 or 28A at step 352, monitoring application waits until connection time 100 (step 370), which is preferably every 24 hours, establishes connection to server 18 (step 360), which is followed by the updating and downloading of new script programs 40 (step 372). The script programs 40 can be an alert, a directive, or a new form to be filled, or a questionnaire. Following this, the apparatus 26 or 28A sends the response 42 to the server 18 in the form of a short text message such as "NIL", meaning that no new responses 42 or measurements 44 were encountered (step 374). The advantage of doing this is that, at regular intervals of time, the functioning of the hardware components of the system, such as apparatus 26, apparatus 28A, device 28, connecting cables 30 and communication network 24 is performed. Therefore, connection is terminated (step 366).

Figure 16B:
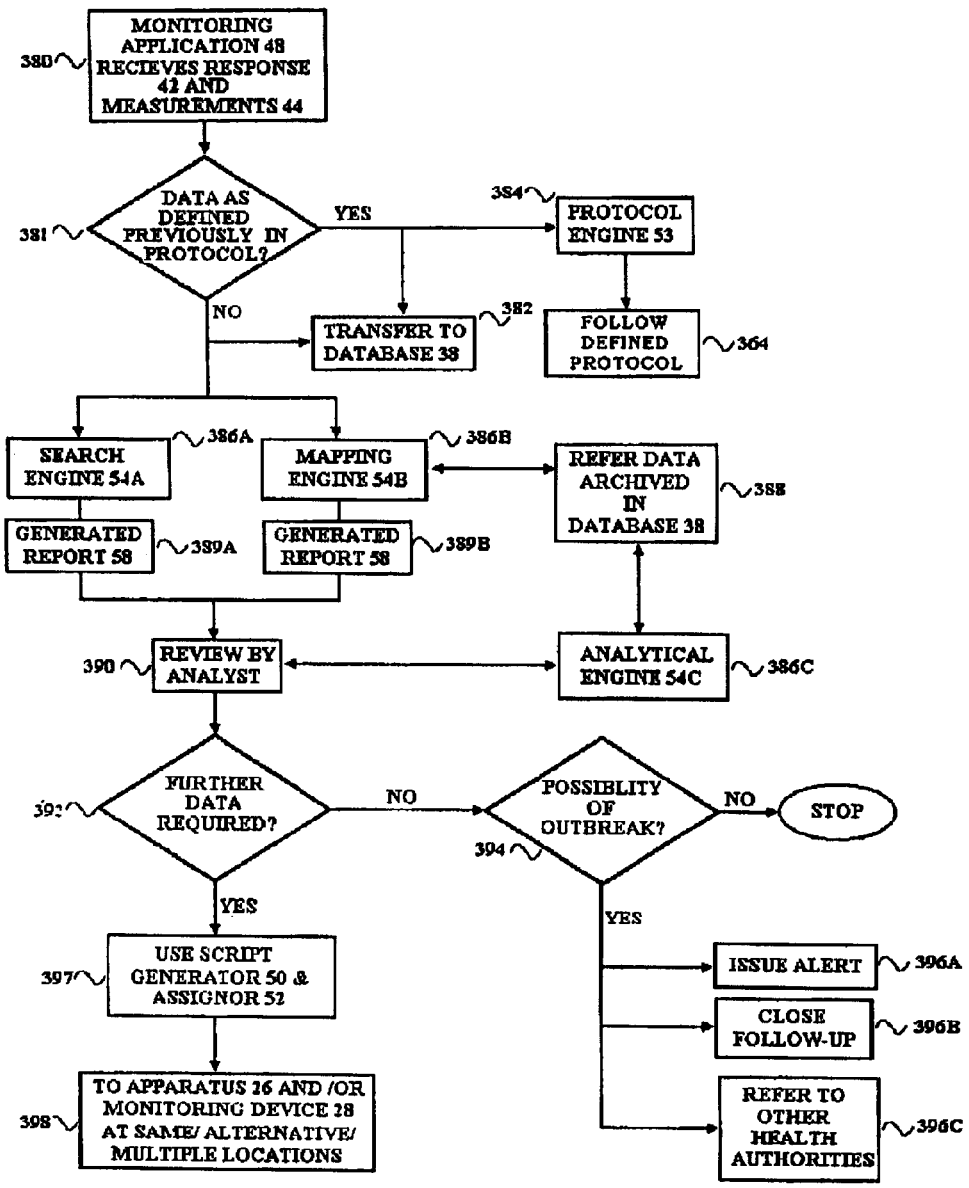
FIG. 16B is a flow chart illustrating the process of data flow and analysis at the workstation and system server of the system of FIG. 15.

FIG. 16B is a flowchart showing the steps involved in data handling at the level of server 18 and the workstation 20. In step 380, the monitoring application 48 receives responses 42 and measurements 44 from apparatus 26, apparatus 28A, monitoring device 28, Interactive Voice Response System 27A and Internet Based Forms 27B. In step 381, the monitoring application 48 checks whether the received responses 42 and measurements 44 are defined in the standard operating procedure code/protocol. If this is the case, it performs steps 382 (transfer of data to the database 38) and step 384 (transfer of data to the protocol engine 53). Step 384 is followed by step 364, where the responses 42 and measurements 44 trigger the script program 40 in the protocol engine, and the standard operating procedure codes are followed. However if, in step 381, the monitoring application 48 determines that the received responses 42 and measurements 44 are not defined in the standard operating procedure code/protocol, step 382 (transfer of data to database 38), step 386A and step 386B are followed. In step 386A, the search engine 54A receives the data, and performs data analysis using methods described in Tables 2, 3, 4, 8 and 11. In addition, the search engine 54A may reference the database 38, and use the information contained therein if the data analysis methods so require (step 388). Step 386B is similar to step 386A in all respects except that, the mapping engine 54B performs data analysis using methods described in Tables 5 through 12. Steps 386A and 386B are followed by steps 389A and 389B respectively, which allow for report generation, in the form of the report 58. In step 390, these reports are preferably reviewed together by the analyst, and if the situation so demands, step 386C is followed, which involves the use of analytical engine 54C to further delve into the data. At this juncture the analyst will form an opinion (step 392) whether the available figures and generated reports are sufficient to reliably exclude a biological event from the public health viewpoint. If further data is not found to be required, the analyst forms an opinion about the possibility of the biological event's being an outbreak (step 394). If the biological event is unlikely to be an outbreak, then the analyst stops further analysis. If it is likely to be an outbreak, or if there is a possibility of its being so, the analyst may either: issue an alert to any or all the reporting locations of the system, using script generator 50 and script assignor 52 (step 396A); or continue to closely monitor and follow up the biological event, using the data analysis tools, protocol engine 53, script generator 50 and script assignor 52 (step 396B); or refer the case, along with relevant data and reports to a statutory body, or other healthcare departments, or other established bodies that may be in a better situation to handle the scenario (step 396C).

If, however in step 392, the analyst determines that further data is required, the analyst may use the script generator 50 and script assignor 52 to create, and assign new script programs 40 to the apparatus 26, 28A, monitoring device 28, IVRS 27A, and Internet Based Forms 27B either singly, or in any combination (step 397). In addition to this new standard operating procedures and protocols may also be incorporated by the analyst into protocol engine 53 in real time, with a view to automate the process, and increase the efficiency of data collection in this scenario, such that all further data inputs would be processed by protocol engine 53, at least in the initial stages. One additional component that may be incorporated into protocol engine 53 is that the analyst be alerted on workstation 20 each time data that fits protocol engine 53 criteria is received by server 18.

In step 398, script programs 40 are sent to apparatus 26, 28A, monitoring device 28, IVRS 27A, and Internet Based Forms 27B, with a view to acquire further data. The data received from these sources is analyzed using the same methodology as that described earlier.

While the preferred embodiment of the invention has been illustrated and described, as noted above, many changes can be made without departing from the spirit and scope of the invention. Accordingly, the scope of the invention is not limited by the disclosure of the preferred embodiment.

The embodiments of the invention in which an exclusive property or privilege is claimed are defined as follows:

1. A health surveillance and monitoring system, the system comprising:
   a server connected to a network and having (i) a database and (ii) a monitoring application;
   a workstation separate from the server, connected to the network and configured to enter one or more queries into the server; and
   a plurality of remotely programmable apparatuses each (1) connected to the network, (2) separate from both the workstation and the server and (3) configured to (i) receive the queries from the server via the network, (ii) obtain one or more responses to the queries respectively from an individual, and (iii) transmit the responses to the server via the network, wherein (A) the server is configured to store the responses in the database and (B) the monitoring application comprises a plurality of programs configured to (i) retrieve the responses from the database, (ii) process the responses and (iii) present one or more reports used to determine a probability of an occurrence of a health condition based on the responses as processed.

2. The system of claim 1, wherein the server comprises a world wide web server.

3. The system of claim 1, wherein the workstation comprises a personal computer.

4. The system of claim 1, wherein (i) at least one of the remotely programmable apparatuses is connectable to a monitoring device, (ii) the monitoring device is configured to (a) produce a plurality of health-related information from the individual an (b) transmit the health-related information to the at least one of the remotely programmable apparatus, (iii) the at least one of the remotely programmable apparatuses is further configured to transmit the health-related information to the server and (iv) the server is further configured to store the health-related information in the database.

5. The system of claim 4, wherein the monitoring device is connectable to an instrument configured to measure the health-related information.

6. The system of claim 4, wherein the monitoring device comprises at least one of a glucose meter, a sphygmomanometer, an automated PCR Device, a toxin sampler, a chemical sampler, a radiation detector, and a thermometer.

7. The system of claim 4, wherein the probability of the occurrence of the health condition is determined by the programs operating on all of (i) the responses stored in the database and (ii) the health-related information stored in the database.

8. The system of claim 1, wherein each of the remotely programmable apparatuses comprises a communications device having a user interface configured to (i) communicate the queries and (ii) receive the responses, the user interface including (a) a display to present the queries as alphanumeric data and (b) a plurality of user input buttons to receive the responses.

9. The system of claim 8, wherein each of the remotely programmable apparatuses further includes a microprocessor configured to (i) execute the queries and (ii) store an identity of the individual responding to the alphanumeric data presented on the display.

10. A health surveillance and monitoring system, the system comprising:
   a server connected to a network and having (i) a database and (ii) a monitoring application;
   a workstation separate from the server, connected to the network and configured to enter one or more queries into the server; and
   a plurality of remotely programmable apparatuses each (1) connected to the network, (2) separate from both the workstation and the server and (3) configured to (i) receive the queries from the server via the network, (ii) obtain responses to the queries from an individual, and (iii) transmit the responses to the server via the network, wherein (A) the server is configured to store the responses in the database and (B) the monitoring application comprises (i) an analysis engine configured to (a) retrieve the responses from the database and (b) process the responses and (ii) a report generator configured to present one or more reports used to determine a probability of an occurrence of a health condition based on the responses as processed.

11. The system of claim 10, wherein the reports comprise a suspicion index that is ascertained by assigning suspicion scores, the suspicion scores determined by comparing current logarithms of positive and negative disease occurrences with past logarithms of positive and negative disease occurrences.

12. The system of claim 10, wherein (i) at least one of the remotely programmable apparatuses is connectable to a monitoring device, (ii) the monitoring device is configured to (a) produce a plurality of health-related information from the individual and (b) transmit the health-related information to the at least one remotely programmable apparatuses, (iii) the at least one remotely programmable apparatuses is further configured to transmit the health-related information to the server and (iv) the server is configured to store the health-related information in the database.

13. The system of claim 12, wherein the monitoring device is connectable to an instrument configured to measure the health-related information.

14. The system of claim 12, wherein the monitoring device comprises at least one of a glucose meter, a sphygmomanometer, an automated PCR Device, a toxin sampler, a chemical sampler, a radiation detector, and a thermometer.

15. The system of claim 12, wherein the probability of the occurrence of the health condition is determined by an analysis of (i) the responses and (ii) the health-related information from the database.

16. The system of claim 10, wherein each of the remotely programmable apparatuses comprises is a communications device having a user interface to (i) communicate the queries and (ii) receive the responses, the user interface including (a) a display to present the queries as alphanumeric data and (b) a plurality of user input buttons to receive the responses.

17. The system of claim 16, wherein each of the remotely programmable apparatuses further includes a microprocessor configured to (i) execute the queries and (ii) store an identity of the individual responding to the alphanumeric data presented on the display.

18. A health surveillance and monitoring system, the system comprising:
   a server connected to a network and having (i) a database and (ii) a monitoring application;
   a workstation separate from the server, connected to the network and configured to enter one or more queries into the server; and
   a plurality of remotely programmable apparatuses each (1) connected to the network, (2) separate from both the workstation and the server and (3) configured to (i) receive the queries from the server via the network, (ii) obtain one or more responses to the queries from an individual, and (iii) transmit the responses to the server via the network, wherein (A) the server is configured to store the responses in the database and (B) the monitoring application is configured to (i) retrieve and process the responses and (ii) present one or more reports used to determine a probability of an occurrence of a health condition in the form of both a suspicion index and a geographical display.

19. The system of claim 18, wherein the suspicion index is determined by assigning suspicion scores, the suspicion scores determined by comparing current logarithms of positive and negative disease occurrences with past logarithms of positive and negative disease occurrences.

20. The system of claim 18, wherein (i) at least one of the remotely programmable apparatuses is connectable to a monitoring device, (ii) the monitoring device is configured to (a) produce a plurality of health-related information from the individual and (b) transmit the health-related information to the at least one remotely programmable apparatus, (iii) the at least one remotely programmable apparatus is further configured to transmit the health-related information to the server and (iv) the server is further configured to store the health-related information in the database.

21. The system of claim 20, wherein the monitoring device is connectable to an instrument configured to measure the health-related information.

22. The system of claim 20, wherein the monitoring device comprises at least one of a glucose meter, a sphygmomanometer, an automated PCR Device, a toxin sampler, a chemical sampler, a radiation detector, and a thermometer.

23. The system of claim 20, wherein the probability of the occurrence of the health condition is determined by the monitoring application operating on all of (i) the responses and (ii) the health-related information.

24. The system of claim 18, wherein the geographical display is generated using data associated with a prior occurrence of a bio-weapon deployment.

25. The system of claim 18, wherein each of the remotely programmable apparatuses comprises a communications device having a user interface to communicate the queries and receive the responses, the user interface including (i) a display to present the queries as alphanumeric data and (ii) a plurality of user input buttons to receive the responses to the alphanumeric data as displayed.

26. The system of claim 25, wherein each of the remotely programmable apparatuses further includes a microprocessor configured to (i) execute the queries and (ii) store an identity of the individual responding to the alphanumeric data presented on the display.

27. A health surveillance and monitoring system, the system comprising:
   a server connected to a network and having (i) a database, (ii) an analysis engine and (iii) a script generator program;

a workstation separate from the server, connected to the network and configured to enter a first query set into the server; and a plurality of remotely programmable apparatuses each (1) connected to the network, (2) separate from both the workstation and the server and (3) configured to (i) receive the first query set queries from the server via the network, (ii) obtain one or more first responses to the first query set from an individual, and (iii) transmit the first responses to the first query set to the server via the network, wherein (A) the server is configured to store the first responses in the database, (B) the script generator program is configured to create a second query set by processing the first responses to the first query set, (C) the server is further configured to send the second query set to the remotely programmable apparatuses, (D) each of the remotely programmable apparatuses (i) obtains one or more second responses to the second query set from the individual and (ii) transmits the second responses to the second query set to the server, (E) the server stores the second responses in the database and (F) the analysis engine is configured to (i) process both the first responses and the second responses stored in the database and (ii) present one or more reports used to determine a probability of an occurrence of a health condition based on the responses as processed.

28. The system of claim 27, wherein the server comprises a world wide web server.

29. The system of claim 27, wherein the workstation comprises a personal computer.

30. The system of claim 27, wherein (i) at least one of the remotely programmable apparatuses is connectable to a monitoring device, (ii) the monitoring device is configured to (a) produce a plurality of health-related information from the individual and (b) transmit the health-related information to the at least one remotely programmable apparatuses, (iii) the at least one remotely programmable apparatuses is further configured to transmit the health-related information to the server and (iv) the server is further configured to store the health-related information in the database.

31. The system of claim 30, wherein the monitoring device is connectable to an instrument configured to measure the health-related information.

32. The system of claim 30, wherein the monitoring device includes at least one of a glucose meter, a sphygmomanometer, an automated PCR Device, a toxin sampler, a chemical sampler, a radiation detector, and a thermometer.

33. The system of claim 30, wherein the probability of the occurrence of the health condition is determined by the analysis engine operating on the responses to (i) the first query set, (ii) the second responses to the second query sets and (iii) the health-related information from the database.

34. The system of claim 27, wherein each of the remotely programmable apparatuses comprises a communications device having a user interface to communication the first query set and receive the first responses, the user interface including (i) a display to present the first query set as alphanumeric data and (ii) a plurality of user input buttons to receive the first responses.

35. The system of claim 34, wherein each of the remotely programmable apparatuses further includes a microprocessor configured to (i) execute the first query set and (ii) store an identity of the individual responding to the alphanumeric data as presented on the display.

* * * * *